(12) United States Patent
Bazan et al.

(10) Patent No.: US 8,343,382 B2
(45) Date of Patent: Jan. 1, 2013

(54) BAND GAP CONTROL IN CONJUGATED OLIGOMERS AND POLYMERS VIA LEWIS ACIDS

(75) Inventors: Guillermo C. Bazan, Goleta, CA (US); Gregory C. Welch, Santa Barbara, CA (US); Robert Coffin, Winston-Salem, NC (US); Jeff Peet, Lowell, MA (US)

(73) Assignee: The Regents of the University of California, Oakland, CA (US)

( * ) Notice: Subject to any disclaimer, the term of this patent is extended or adjusted under 35 U.S.C. 154(b) by 74 days.

(21) Appl. No.: 12/800,904

(22) Filed: May 24, 2010

(65) Prior Publication Data

US 2011/0028656 A1    Feb. 3, 2011

Related U.S. Application Data

(60) Provisional application No. 61/180,566, filed on May 22, 2009.

(51) Int. Cl.
*H01B 1/00* (2006.01)
*H01L 29/08* (2006.01)
*H01L 27/14* (2006.01)
*C08G 75/00* (2006.01)
*C07D 513/02* (2006.01)

(52) U.S. Cl. .......... 252/500; 257/40; 257/431; 528/377; 546/114

(58) Field of Classification Search .................. 252/500; 257/40, 431; 528/377; 546/114
See application file for complete search history.

(56) References Cited

U.S. PATENT DOCUMENTS
7,772,485 B2 * 8/2010 Gaudiana et al. ............. 136/252

FOREIGN PATENT DOCUMENTS
WO    WO 2010000755 A1 * 1/2010

OTHER PUBLICATIONS

Roncali, J. *Macromol. Rapid Commun.* 2007, 28, 1761.
Gratzel, M. *J. Photochem. Photobiol. C Photochem. Rev.* 2003, 4, 145.
Scharber, M.C.; Wuhlbacher, D.; Koppe, M.; Denk, P.; Waldauf C.; Heeger, A.J.; Brabec, C.L. *Adv. Mat.* 2006, 18, 789.
Dennler, G.; Scharber, M. C.; Brabec, C. J. *Adv. Mater* 2009, 21,1.
Hou, J.; Chen, H. Y.; Zhang, S.; Li, G.; Yang, Y. *J. Am. Chem. Soc.* 2008, 130, 16144.
Peet, J.; Kim, Y.; Coates, N. E.; Ma, W. L.; Moses, D.; Heeger, A. J.; Bazan, G. C. *Nat. Mat.* 2007, 6, 497.
Kim, J. Y.; Lee, K.; Coates, N. E.; Moses D.; Nguyen, T. Q.; Dante, M.; Heeger, A. J. *Science* 2007, 317, 222.

(Continued)

*Primary Examiner* — Mark Kopec
*Assistant Examiner* — Jaison Thomas
(74) *Attorney, Agent, or Firm* — Berliner & Associates

(57) ABSTRACT

A method for altering the electronic and optical properties of a chemical compound having a band gap and a framework that includes π-delocalized electrons. The method includes complexing a Lewis acid to a basic site within the framework to form a Lewis acid adduct having a band gap that differs from the band gap of the chemical compound. The $\lambda_{max}$ of the Lewis acid adduct can be shifted to a longer wavelength in comparison to the $\lambda_{max}$ of the chemical compound. In various versions, the chemical compound can be a conjugated oligomer, a conjugated polymer, or a small molecule comprising a conjugated π-electron system. Electronic devices that include Lewis acid adducts are also provided.

9 Claims, 43 Drawing Sheets

OTHER PUBLICATIONS

Anant, P.; Lucas, N. T.; Jacob, J. *Org. Lett.* 2008, 10, 5533.
Kato, S.; Matsumoto, T.; Shigeiwa, M.; Gorohmaru, H.; Maeda, S.; Ishi-i, T.; Mataka, S. *Chem. Eur. J.* 2006, 12, 2303.
Focante, F.; Mercandelli, P.; Sironi, A.; Resconi, L. *Coord. Chem. Rev.* 2006, 250, 170.
Fraleoni-Morgera, A.; Giorgini, L.; Zanirato, P. *Dyes and Pigments* 2008, 76, 394-399.
Cazenobe, I.; Ledoux, I.; Zyss, J.; Thornton, A.; Bruce, D. W.; Kakkar, A. K.; Lesley, G. M. J.; Woodward, A.; Taylor, N. J.; Marder, T. B. *Chem. Mater.* 1998, 10, 1355.
Lopez-Garriga, J. J.; Babcock, G. T.; Harrison, J. F. *J. Am. Chem. Soc.* 1986, 108, 7131.
Son, H. J.; Han, W. S.; Chun, J. Y.; Kwon, S. N.; Ko, J.; Kang, S. O. *Organometallics* 2008, 27, 2464.
Lee, I. S.; Kwak, Y. W.; Kim, D. H.; Cho, Y.; Ohshita J. *J. Orgmet. Chem.* 2008, 693, 3233.
Lee, I. S.; Kim S. J.; Kwak, Y. W.; Choi, M. C.; Park, J. W.; Ha, C. K. *J. Indus. Engn. Chem.* 2008, 14, 344.
Piers, W. E. *Adv. Orgmet. Chem.* 2005, 52, 1.
Massey, A. G.; Park, A. J.; Stone, F. G. A. *Proc. Chem. Soc.* 1963, 208.
Pearson, R. G. *J. Am. Chem. Soc.*, 1963, 85, 3533.
Focante, F.; Camurati, I.; Resconi, L.; Guidotti, S.; Beringhelli, T.; D'Alfonso, G.; Donghi, D.; Maggioni, D.; Mercandelli, P.; Sironi, A. *Inorg. Chem.*, 2006, 45, 1683.
Jacobsen, H.; Berke, H.; Döring, S.; Kehr, G.; Erker, G.; Fröhlich, R.; Meyer, O. *Organometallics* 1999, 18, 1724.
Apblett, A.; Chivers, T.; Richardson, J. F. *Can. J. Chem.* 1986, 64, 849.
Bazan G. C. *J. Org. Chem.* 2007, 72, 8651.
Pilgram, K.; Zupan, M.; Skiles, R. J. Heterocyclic Chem istry 1970, 7, 629-633.
Lu, G.; Usta, H.; Risko, C.; Wang, L.; Facchetti, A.; Ratner, M. A.; Marks, T. J. *J. Am. Chem. Soc.* 2008, 130, 7670-7685.
Zhu, Z. et al., *Macromolecules*, 40, 1981-1986 (2007).
Coffin, R.; Peet, J.; Rogers, J.; Bazan, G. *Nat. Chem.* 2009, 1, 657.
Coppo, P.; Cupertino, D. C.; Yeates, S. G.; Turner, M. L. *Macromolecules* 2003, 36, 2705.
Blouin, N.; Michaud, A.; Gendron, D.; Wakim, S.; Blair, E.; Neagu-Plesu, R.; Belletete, M.; Durocher, G.; Tao, Y.; Leclerc, M.; *J. Am. Chem. Soc.* 2008, 130, 2, 732.
Spek, A. L. *Journal of Applied Crystallography* 2003, 36, 7-13.
Becke, A. D. *J. Chem. Phys.* 1993, 98, 1372.
Becke, A. D. *J. Chem. Phys.* 1993, 98, 5648.
Lee, C.; Yang, W.; Parr, R. G. *Phys. Rev. B* 1988, 37, 785.
Bram, P. et al., J. Mater. Chem., 2009, 19, 5343-5350.

* cited by examiner

BAND GAP CONTROL IN CONJUGATED OLIGOMERS AND POLYMERS VIA LEWIS ACIDS

CROSS-REFERENCE TO RELATED APPLICATIONS

This application claims the benefit of Provisional Patent Application No. 61/180,566, filed on May 22, 2009, which is incorporated by reference herein.

STATEMENT REGARDING FEDERALLY SPONSORED RESEARCH OR DEVELOPMENT

This invention was made with Government support under Grant No. 0606414 from the National Science Foundation, and Grant No. 8-448777-23057-3 from the Office of Naval Research. The Government has certain rights in this invention.

BACKGROUND

1. Field of the Invention

The invention relates to chemical compounds having π-delocalized electrons, including chromophores, conjugated oligomers, and conjugated polymers.

2. Background

Organic π-conjugated oligomeric or polymeric materials are frequently utilized as organic semi-conductors as they combine solution processing and good charge transport properties with the ability of their electronic structure to be fine tuned to efficiently absorb and emit photons across the solar spectrum. As a result, such materials are used as the active component in several types of electronic and optoelectronic devices, including organic field effect transistors (OFET's), organic light emitting diodes (OLED's), and organic photovoltaic devices (OPV's).

In the area of solar energy conversion, some bulk heterojunction "plastic" solar cells are fabricated with conjugated polymers having backbones comprising alternating donor/acceptor (D/A) comonomer units. This structural motif leads to excited states with charge transfer characteristics and to energy transitions on the order of 1.4 eV. (Refs: 1-10).

Organic materials with very narrow bandgaps (<1.4 eV) that absorb well into the near infrared (NIR) region of the solar spectrum have begun to attract interest as they have potential to be incorporated into NIR photodetectors, NIR photovoltaic and electrochromic devices. The most common method to extend absorption into the NIR region has simply involved increasing the electron acceptor or donor character of D-A type materials to lower the LUMO energy or raise the HOMO energy, respectively. While this strategy has worked to yield many novel NIR absorbing materials, the synthesis has often been multi-step and costly and thus new methods to alter the bandgap of organic materials are desired.

BRIEF SUMMARY

The ability to modulate the electronic properties of a conjugated molecule, such as a benzo-2,1,3-thiadazole (BT) electron acceptor unit, via interactions with Lewis acids that bind a basic site in the molecule, such as nitrogen, is now shown. Through the selective binding of a Lewis acid to, for example, an accessible nitrogen atom on the acceptor unit, electron density can be removed from the system resulting in a narrowing of the optical band gap. This approach of modulating the electronic properties of conjugated molecules by interaction with Lewis acids makes it possible to access a range of chromophores starting with a single, well-defined small molecule compound. Control of the optical band-gap can be achieved by varying the strength of the Lewis acid.

In one aspect, a method for altering the electronic properties of a chemical compound is provided. The chemical compound has a band gap and a framework that includes π-delocalized electrons. The method includes complexing a Lewis acid to a basic site within the framework to form a Lewis acid-base adduct having a band gap that differs from the band gap of the chemical compound.

In other aspects, Lewis acid adducts, and devices that include such compounds, are provided. Also provided are novel π-conjugated oligomeric and polymeric materials, which can be complexed with a Lewis acid as described herein to alter band gap energies.

BRIEF DESCRIPTION OF THE DRAWINGS

For a more complete understanding of the present invention, reference is now made to the following descriptions taken in conjunction with the accompanying drawing.

DETAILED DESCRIPTION

Figure 1:
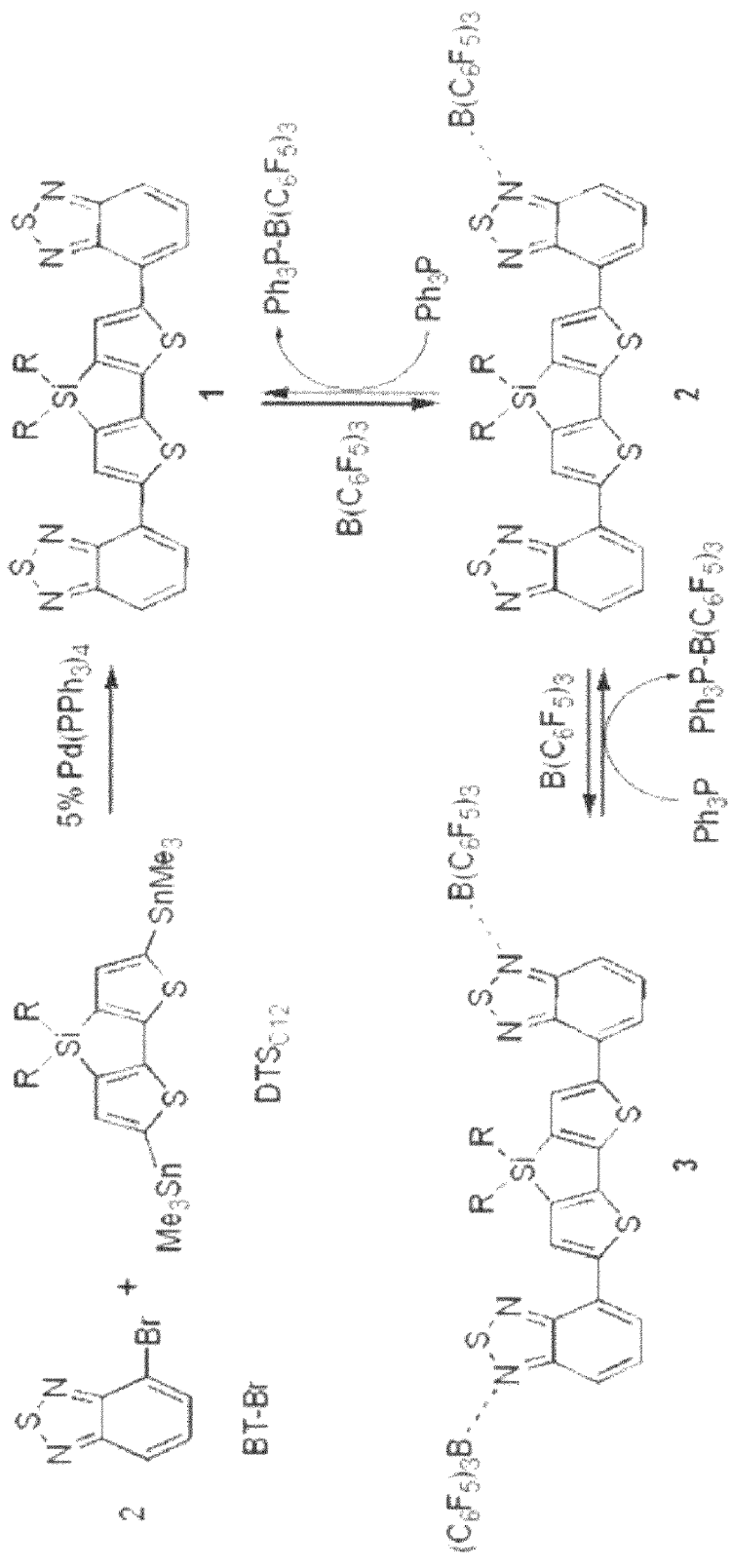
FIG. 1 is a diagram of Scheme 1, showing a synthetic route to 1 and the Lewis acid adducts 2 and 3 ($R=C_{12}H_{25}$).

A method is provided for altering the electronic and/or optical properties of a chemical compound having a band gap and a framework that comprises π-delocalized electrons. The method comprises complexing a Lewis acid to a basic site within the initial molecular framework to form a Lewis acid adduct having a band gap that differs from the band gap of the chemical compound. The band gap of the Lewis acid adduct can be decreased in comparison to the band gap of the chemical compound. As a result of complexation with the Lewis acid, the $\lambda_{max}$ of the Lewis acid adduct can be shifted to a longer wavelength in comparison to the $\lambda_{max}$ of the chemical compound.

In various embodiments, the chemical compound can be a conjugated oligomer, or a conjugated polymer comprising a conjugated π-electron system. The chemical compound of any embodiment can comprise an acceptor/donor (AD) structure, which can be an $A(DA)_n DA$ structure (where n=0-100), $D(AD)_n AD$ structure (where n=0-100), $(DD)_n A_m (DD)_n$ structure (where n=1-10, m=1-10), $(AA)_n D_m (AA)_n$ structure (where n=1-10, m=1-10), or any variation thereof. The acceptor unit comprises a conjugated π-electron system with a lone pair of electrons that has a greater electron affinity than the donor unit. The donor unit comprises a conjugated π-electron system that has a lesser electron affinity than the acceptor unit. In any embodiment, the chemical compound can be a chromophore.

Examples of acceptor units include, but are not limited to benzo[2,1,3]thiadiazole, benzo[2,1,3]oxadiazole, [1,2,5]thiadiazolo[3,4-c]pyridine, [1,2,5]oxadiazolo[3,4-c]pyridine, pyrido[3,4-b]pyrazine, quinoxaline or benzopyrazine, benzylidenemalononitrile, dicyanovinylthiophene, floureneone, benzaldhyde, acetophenone, benzonitrile, benzo[c][1,2,5]thiadiazole-4-carbonitrile, benzo[c][1,2,5]oxadiazole-4-carbonitrile, benzo[c][1,2,5]thiadiazol-4-amine, benzo[c][1,2,5]oxadiazol-4-amine, benzo[c][1,2,5]thiadiazol-4-phosphine, benzo[c][1,2,5]oxadiazol-4-phosphine, thieno[3,4-b]pyrazine, 2-(9H-fluoren-9-ylidene)malononitrile, thienothiophene, diketopyrrolopyrrole, borole or any aromatic heterocyclic ring system with a pendent or incorporated imine, nitrile, carbonyl, amine, phosphine, phosphinimine, pyridine, or ether moiety.

Examples of donor units include, but are not limited to thiophene, pyrrole, 9,9-RR'-9H-fluorene, 9-R-9H-carbazole, 3,3'-RR'silylene-2,2'-bithiophene, 3,3'RR'-cyclopenta[2,1-b:3,4-b']-dithiophene, benzodithiophene, pyridinedithiophene, where R and R' are each independently alkyl or aryl with $C_n$=1 to 30, or any C, Si, N, P, S, Se heteroatom containing aromatic ring system.

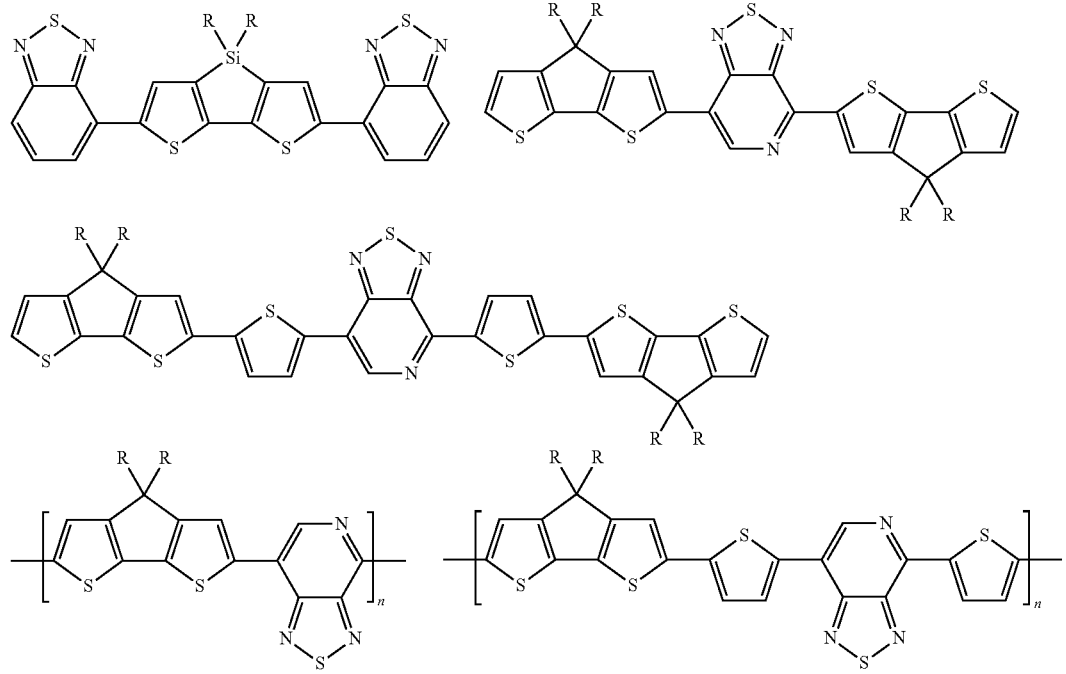

Examples of Lewis acids include, but are not limited to, $BR_3$, $AlR_3$, $GaR_3$, $R_2BXBR_2$, $R_2AlXAlR_2$ where R=F, Cl, Br, alkyl with $C_n$ (n=1 to 30), aryl with $C_n$ (n=5 to 30), perfluoroalkyl with $C_n$ (n=1 to 30), perfluoroaryl with $C_n$ (n=5 to 30), or any combination thereof and X=alkyl with $C_n$ (n=1 to 30), aryl with $C_n$ (n=5 to 30), perfluoroalkyl with $C_n$ (n=1 to 30), perfluoroaryl with $C_n$ (n=5 to 30), or any combination thereof.

The basic site within the chemical compound framework acts as a two-electron donor and can be, but is not limited to, N, P, O, or S.

A method of preparing a series of Lewis adducts having a range of band gaps and $\lambda_{max}$ values is also provided. The method comprises providing a chemical compound having a band gap and a framework that comprises π-delocalized electrons, and a group of Lewis acids of differing Lewis acidic strengths; and for each Lewis acid, complexing the Lewis acid to a basic site within the chemical compound framework to form a Lewis acid adduct having a band gap that differs from the band gap of the chemical compound. The group of Lewis acids thus form a series of Lewis acid adducts having a range of band gaps and $\lambda_{max}$ values. In the method, the chemical compound, Lewis acid, and basic site within the chemical compound framework can be any of those described herein. When the group of Lewis acids is arranged by increasing strength, the series of Lewis acid adducts prepared from the group can be arranged according to increasing $\lambda_{max}$ values.

In other embodiments, any Lewis acid adduct prepared by the methods disclosed herein is provided.

An electronic device comprising any one or more of the conjugated compounds, including any species or Lewis acid adduct, prepared by the methods disclosed herein is also provided. Examples of devices include, but are not limited to, optoelectronic devices, optoelectronic semiconductor chips, semiconductor thin-films, photovoltaics, semiconducting solar cells, and dye-sensitized solar cells.

Additional embodiments include an organic material comprising one or any combination of the following:

or any Lewis acid adduct thereof. In any of these embodiments, each R is independently a $C_{1-30}$ alkyl or $C_{5-30}$ aryl group. In addition, each n is $\geq 1$, and in certain embodiments n=1-100.

Also provided are the particular conjugated compounds described herein, including 1, 2, and 3 (Scheme 1), and G1, G2, P1, P2 and P3, or any Lewis acid adduct thereof.

The present invention may be better understood by referring to the accompanying examples, which are intended for illustration purposes only and should not in any sense be construed as limiting the scope of the invention.

Example 1

Our studies focused on 1 (Scheme 1), which has an A/D/A structure and was synthesized via microwave assisted Stille cross-coupling reaction between BT-Br and $DTS_{C12}$, as outlined in Scheme 1 of FIG. 1 (11). Precipitation with methanol and purification via chromatography gave the desired product as a red solid in 85% yield. Species 1 was characterized by multinuclear NMR spectroscopy, high-resolution mass spectrometry, and elemental analysis (12).

Figure 2:
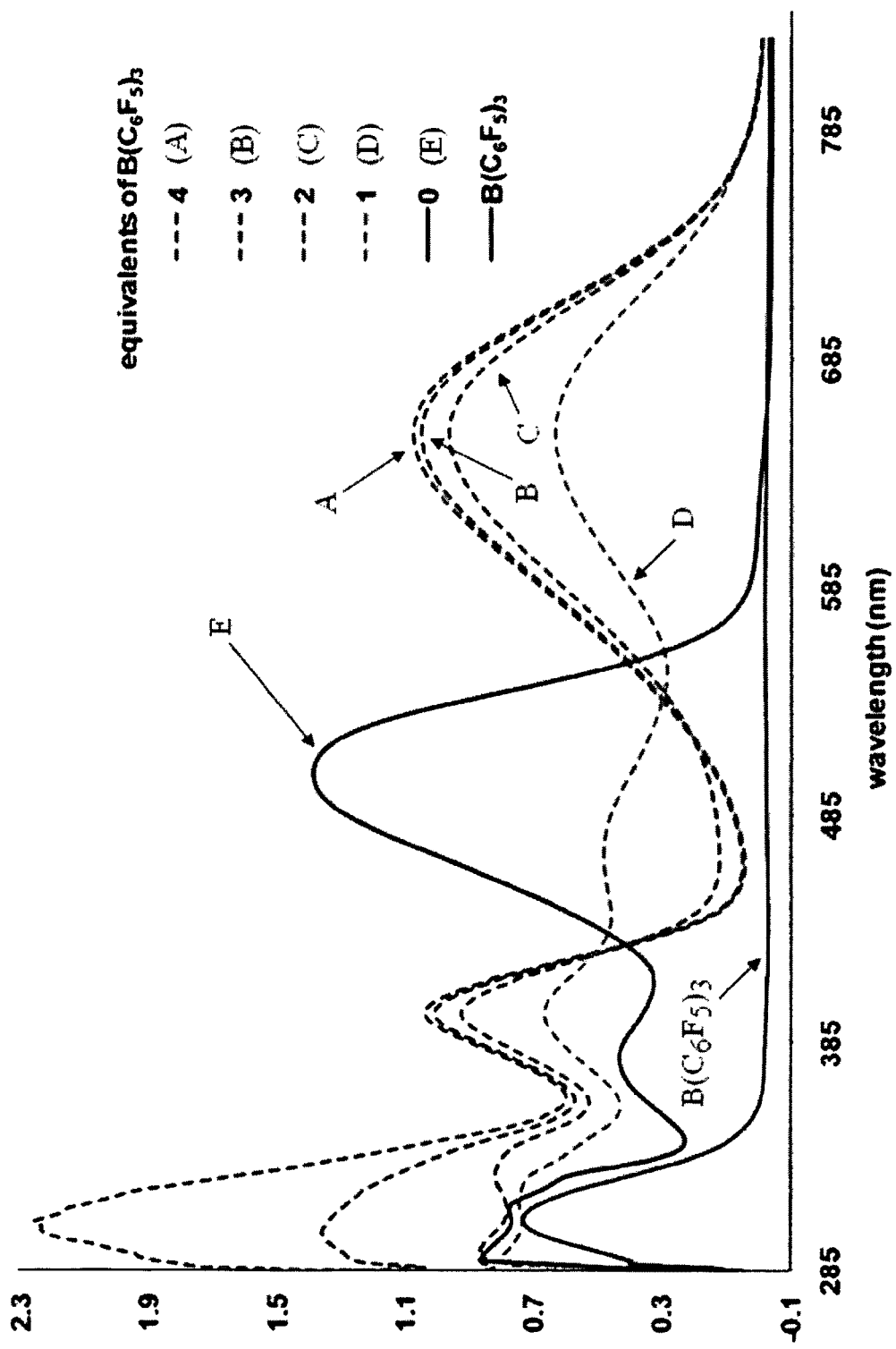
FIG. 2 is a plot showing the absorption spectra of 1 plus varying equivalents of $B(C_6F_5)_3$ in 1,2-dichlorobenzene at 25° C. ([1]=$3.78 \times 10^{-4}$ M).

The absorbance spectrum of 1 in 1,2-dichlorobenzene exhibits an absorption maximum ($\lambda_{max}$) at 503 nm with an onset ($\lambda_{onset}$) at 577 nm, as shown in FIG. 2. A striking color change from red to green to blue can be observed by visual inspection upon addition of 2 equivalents of the Lewis acid $B(C_6F_5)_3$ (13). Analysis by UV-visible spectroscopy reveals the disappearance of the primary band for 1 and the appearance of a new transition with $\lambda_{max}$=647 nm. Addition of greater than 2 equivalents of $B(C_6F_5)_3$ results in minimal intensity change at 647 nm, and the emergence of a band at $\lambda_{max}$=305 nm, due to unbound B(C$_6$F$_5$)$_3$. Stepwise addition of 0-2 equivalents of B(C$_6$F$_5$)$_3$ in 0.1 molar increments reveals the existence of two separate isosbestic points at approximately 537 nm and 557 nm, which indicate the presence of more than two absorbing species in solution (12). These data are consistent with the stepwise formation of mono- and bis-Lewis acid adducts. Based on the well known propensity of boranes to bind harder nitrogen bases over the softer sulfur counterparts, the structures of the adducts are proposed to be 2 and 3, respectively, as in Scheme 1 (14).

Deep blue 3 can be isolated as a solid in greater than 90% yield after addition of 2 equivalents of B(C$_6$F$_5$)$_3$ to 1, followed by solvent. Absorption characteristics are identical to those in FIG. 2 for the addition of 2 equivalents B(C$_6$F$_5$)$_3$. The $^1$H NMR spectrum of 3 in CD$_2$Cl$_2$ at 25° C. shows 4 CH resonances from 7.4 to 8.4 ppm; each B(C$_6$F$_5$)$_3$ is thus bound at opposite ends of the molecule. $^{11}$B and $^{19}$F NMR spectra show no evidence of free B(C$_6$F$_5$)$_3$ and upon cooling to −30° C. the $^{19}$F NMR spectrum exhibits 15 independent signals. There is thus restricted rotation about the B—N and B—C$_6$F$_5$ bonds (12, 15). Addition of excess PPh$_3$ to 3 gives rise in an immediate color change from blue to the red characteristic of 1 and the formation of Ph$_3$P—B(C$_6$F$_5$)$_3$, as determined by $^{31}$P NMR spectroscopy (16). These observations indicate that displacement of the Lewis acid is possible by using a stronger base. Significantly, there is no change in the conjugated framework of 1.

Complex 2 could not be independently isolated. The $^1$H NMR spectrum of a 1:1 ratio of B(C$_6$F$_5$)$_3$:1 in CD$_2$Cl$_2$ exhibits broad signals, which indicate exchange of borane between nitrogen atoms. Upon cooling to −30° C., exchange is slowed and an equilibrium mixture of 1, 2, and 3 was observed in a 1:2:1 ratio (12). The binding of B(C$_6$F$_5$)$_3$ is therefore surmised to be statistical, i.e. binding of B(C$_6$F$_5$)$_3$ to one end of 1 does not greatly influence the basicity at the unbound nitrogen at the other extreme of the chromophore.

Figure 3:
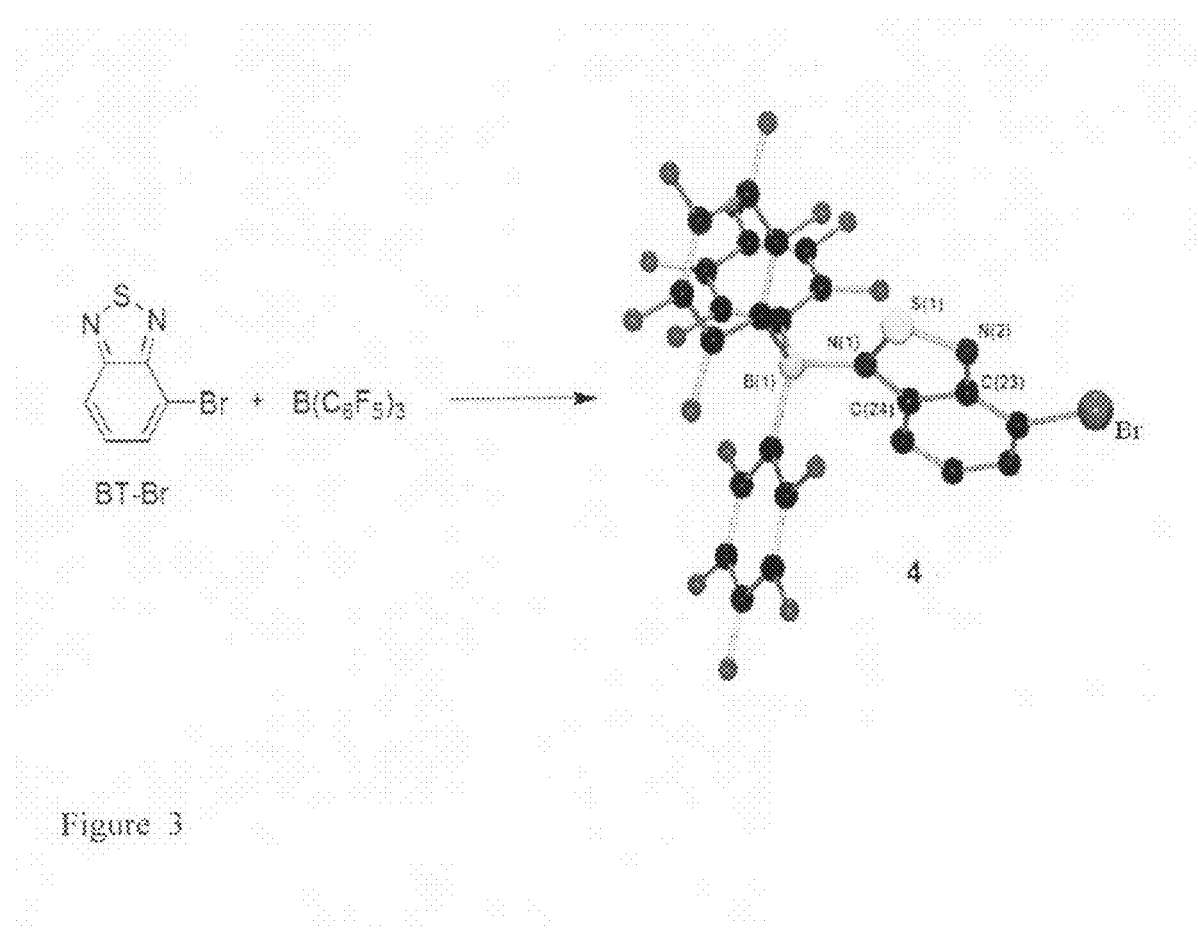
FIG. 3 is a depiction of the molecular structure of species 4, obtained by a single crystal X-ray diffraction study. Species 4 is a Lewis adduct between $B(C_6F_5)_3$ and BT-Br. The two nitrogens, boron, sulfur and bromine atoms are labeled. Hydrogen atoms on carbon are omitted for clarity. Selected metrical parameters {distances (Å), angles (°)} are: B(1)-N(1) 1.556(17), N(1)-S(1) 1.620(16), N(2)-S(1) 1.500(16), N(1)-C(24) 1.294 (16), N(2)-C(23) 1.312(15).

While good quality single crystals of 2 or 3 were not obtained, it was possible to do so with the adduct containing B(C$_6$F$_5$)$_3$ and BT-Br, i.e. species 4. The solid-state structure of 4 determined by X-ray diffraction studies is summarized in FIG. 3 (12). As shown, B(C$_6$F$_5$)$_3$ binds to nitrogen instead of sulfur (17). Furthermore, it chooses to do so at the 1-position of the BT unit, opposite the Br atom, presumably due to steric constraints. A similar regiochemistry is expected in 2 and 3 (Scheme 1). Addition of excess borane to 4 or 3 in solution did not result in a second or third B—N bond formation, respectively, from 25 to −50° C., as determined by $^1$H and $^{19}$F NMR spectroscopy (12). This lack of subsequent reactivity is likely due to the combination of steric constraints and the depletion of electronic density within the BT fragment upon binding the first equivalent of B(C$_6$F$_5$)$_3$.

The absorption spectra of 1 and 3 in the solid-state were compared to their characteristics in solution. The spectrum of 1 in the solid shows minimal change in $\lambda_{max}$ vs. solution, although the appearance a shoulder at 544 nm is indicative of multichromophore interactions (12). No such differences are observed for 3, consistent with the bound B(C$_6$F$_5$)$_3$ increasing the distance between optically active fragments to the point where significant through-space interactions do not take place (18).

Figure 4:
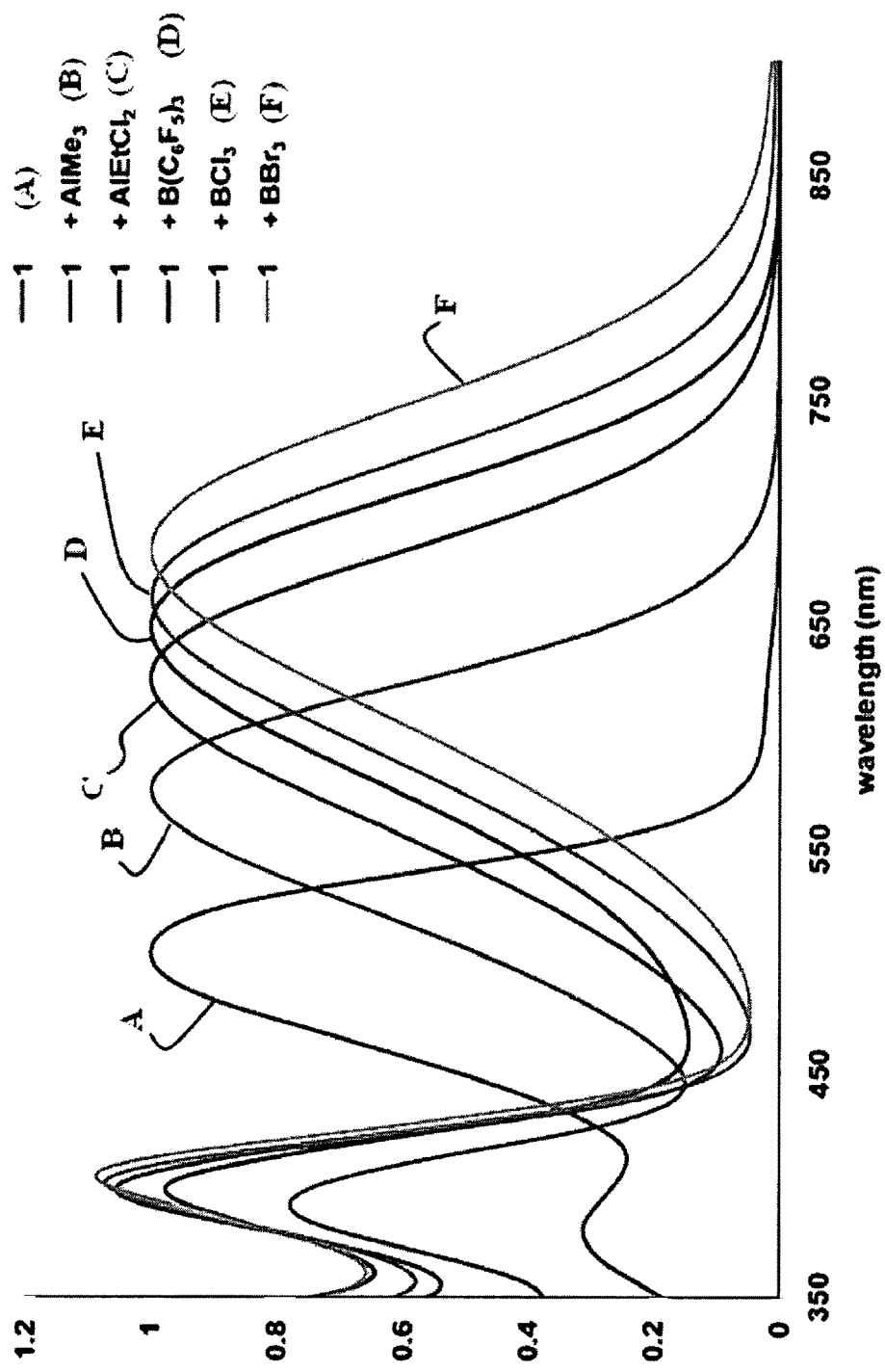
FIG. 4 is a plot showing the normalized absorption spectra of 1 in 1,2-dichlorobenzene in the presence of 2 equivalents of various Lewis acids.

To explore the generality of the band gap modification, a range of Lewis acids (AlMe$_3$, AlEtCl$_2$, BCl$_3$, and BBr$_3$) were added to 1 in 1,2-dichlorobenzene and the UV-vis spectra of the resulting mixtures recorded. As can be seen in FIG. 4, a series of red-shifted complexes that cover most of the visible region can be obtained. Addition of the relatively weak acid AlMe$_3$ results in the formation of a violet solution, a 70 nm red shift in $\lambda_{max}$ and a 109 nm red shift in $\lambda_{onset}$. The effect of the strongest Lewis acid, acid BBr$_3$ is much more pronounced, yielding a blue-green colored complex. In this case $\lambda_{max}$ and $\lambda_{onset}$ are red shifted relative to 1 by 178 and 257 nm, respectively (12). Indeed, the optical absorption of the BBr$_3$ analog of 3 approaches that of known polymers containing DTS and BT repeat units (5). The general trend shows that the largest red-shift is obtained with the strongest Lewis acid.

In conclusion, the synthesis, structural characterization and optical properties of 1, 2, and 3 demonstrate a strategy for tuning the optical properties of an A/D/A chromophore with charge transfer excited state characteristics. The basic strategy involves Lewis acid complexation to a basic site within the π-delocalized framework. Our current thinking is that this complexation increases the electron affinity of the BT acceptor group, thereby stabilizing the charge transfer characteristics of the excited state. From a practical perspective it is interesting to note that a progressive shift to lower energy transitions can be achieved as the strength of the Lewis acid is increased. It is anticipated that the approach will be general for small molecules, oligomers and even D/A conjugated copolymers in which acceptor fragments provide sterically unencumbered lone pairs of electrons. It is also anticipated that changes in the absolute energies of the highest occupied and lowest unoccupied molecular orbital levels can be achieved by this method.

Example 2

Supporting Information for Example 1

General Data: Preparations were carried out on a bench top or under an atmosphere of dry, O$_2$-free N$_2$ employing both Schlenk line techniques and an Vacuum Atmospheres inert atmosphere glove box. Solvents (pentane, toluene, THF) were dried over sodium/benzophenone, distilled under vacuum, and stored over molecular sieves (4 Å). Solvents (methylene chloride, chloroform, 1,2-dichlorobenzene) were dried over calcium hydride, distilled under vacuum, and stored over molecular sieves (4 Å). Molecular sieves (4 Å) were purchased from Aldrich Chemical Company and dried at 140° C. under vacuum for 24 hours prior to use. Deuterated solvents were dried over CaH$_2$ (CD$_2$Cl$_2$, CDCl$_3$) or sodium/benzophenone (C$_6$D$_6$) and vacuum distilled prior to use. All reactants and reagents are commerically available and used as received unless otherwise noted. 4-bromo-benzo[2,1,3]thiadiazole (19) 3,3'-dibromo-2,2'-bithiophene (20) were prepared by literature methods. B(C$_6$F$_5$)$_3$ was purified by treatment with neat Et$_3$SiH, extraction with boiling toluene, and sublimation at 120° C. under vacuum. It is imperative that all Lewis acids be handled using strict anhydrous conditions.

NMR: $^1$H, $^{13}$C, $^{11}$B, and $^{19}$F nuclear magnetic resonance (NMR) spectroscopy spectra were recorded on a Bruker Avance-500 MHz spectrometer at 25° C. unless otherwise noted. $^1$H and $^{13}$C NMR spectra are referenced to SiMe$_4$ using the residual solvent peak impurity of the given solvent. $^{11}$B and $^{19}$F NMR experiments were referenced to BF$_3$(OEt$_2$), and CFCl$_3$, respectively. Chemical shifts are reported in ppm and coupling constants in Hz as absolute values. DEPT, $^1$H-$^1$H, and $^1$H/$^{13}$C correlation experiments were completed for assignment of the carbon atoms.

UV-vis: UV-visible spectroscopy was recorded with a Beckman Coulter DU 800 series or Perkin Elmer Lambda 750 spectrophotometer at room temperature. All solution UV-vis experiments were run under a N$_2$ atmosphere in teflon capped 1 mm quartz cuvettes using 1,2 dichlorobenzene as the solvent. All solutions were prepared by adding an appropriate amount of 0.01 M Lewis acid solution in 1,2-dichlorobenzene to a 0.1 mL aliquot of a 0.01 M dichlorobenzene solution of 1 and diluting to 2.65 mL to give a solution with a final concentration of 0.000378 M wrt 1. All solid UV-vis experiments were run under a N$_2$ atmosphere. Films were prepared by spin casting the appropriate solution (20 mg/mL in chloroform wrt 1) onto a 15 mm×15 mm×2 mm quartz substrate at 700 rpm under an atmosphere of N$_2$.

CHN: Combustion analyses were performed by the MSI analytical lab at the University of California, Santa Barbara.

X-ray Data Collection, Reduction, Solution and Refinement: Single crystals were coated in paratone-N oil under $N_2$ and mounted onto a thin-walled capillary with epoxy resin. The data were collected using the SMART software package (21) on a Siemens SMART System CCD diffractometer using a graphite monochromator with MoKα radiation (λ=0.71073 Å). A hemisphere of data was collected in 1950 frames with 10 second exposure times unless otherwise noted. Data reductions were performed using the SAINT software package (22) and absorption corrections were applied using SADABS (22). The structures were solved by direct methods using XS and refined by full-matrix least-squares on $F^2$ using XL as implemented in the SHELXTL suite of programs (23). All non-H atoms were refined anisotropically. Carbon-bound hydrogen atoms were placed in calculated positions using an appropriate riding model and coupled isotropic temperature factors. Disordered $CH_2Cl_2$ solvent molecules were removed using the 'squeeze' command in PLATON (24).

Synthesis of Dichlorodi-n-dodecylsilane

To a dry tarred 500 mL Schlenk bomb flask was condensed 29.0 g (0.286 mol) of dichlorosilane at −78° C. To this was added 100 g (0.594 mol) of 1-dodecene under an argon flow. This mixture was allowed to warm to 0° C., then 100 mg (0.193 mmol) of hexachloroplatinic acid hexahydrate dissolved in 2 mL of isopropanol was added via syringe. The mixture was allowed to slowly warm to room temperature where it was allowed to stir for 40 hours. After this time the solution was cannula transferred into a dry 250 mL 3-necked round bottom flask equipped with a fractional distillation apparatus. The mixture was distilled at 220° C. at 0.1 mmHg. Yield: 78.1 g (62.5%). $^1$H NMR (400 MHz, $C_6D_6$): δ=1.6-1.4 (m, 4H), 1.4-1.1 (m, 36H), 1.0-0.8 (m, 10H). $^{13}$C NMR (100 MHz, $C_6D_6$): δ=33.19, 32.72, 30.51, 30.30, 30.21, 29.89, 23.51, 23.16, 20.92, 14.77. HRMS (EI) m/z, calcd for $C_{24}H_{50}Cl_2Si$ ($M^+$): 436.3059; found: 436.3058.

Synthesis of 3,3'-Di-n-dodecylsilylene-2,2'-bithiophene

To a 1 L 3-necked round bottom containing 30 mL (48.0 mmol) of 1.6 M in 400 mL of THF at −78° C. was added dropwise over 15 minutes 7.42 g (22.9 mmol) of 3,3'-dibromo-2,2'-bithiophene dissolved in 50 mL of THF. Immediately following this addition 10.0 g (22.8 mmol) of dichlorodi-n-dodecylsilane in 50 mL was added dropwise over 30 minutes. After the addition the reaction was quickly warmed to room temperature by placing in a water bath. The mixture was stirred for 1 hour at this temperature then 200 mL of concentrated ammonium chloride was added to the reaction mixture. The mixture was poured into an addition funnel and 200 mL of hexanes as added. The organic layer was collected and the aqueous layer was further extracted with 3×100 mL of hexanes. The combined organic layers were dried over anhydrous $MgSO_4$. The solvent was removed by rotovap and the crude material was purified via flash chromatography using hexanes as the eluent yielding 7.5 g (61.5%) of a pale yellow oil. $^1$H NMR (400 MHz, $CDCl_3$): δ=7.20 (d, 2H, $^3J_{HH}$=4.8 Hz), 7.06 (d, 2H, $^3J_{HH}$=4.8 Hz), 1.43-1.32 (m, 4H), 1.32-1.15 (m, 36H), 0.96-0.83 (m, 10H). $^{13}$C NMR (100 MHz, $CDCl_3$): δ=149.42, 141.77, 129.81, 125.11, 33.39, 32.17, 29.90, 29.77, 29.61, 29.44, 24.44, 22.94, 14.35, 12.11. HRMS (EI) m/z, calcd for $C_{32}H_{54}S_2Si$ ($M^+$): 530.3436; found: 530.3437.

Synthesis of 5,5'-Bis(trimethylstannyl)-3,3'-Di-n-dodecylsilylene-2,2'-bithiophene ($DTS_{C12}$)

To a solution of 2.20 g (4.14 mmol) of 2 in 50 mL of THF was added 5.7 mL (9.1 mmol) of 1.6 M n-butyllithium in hexane at −78° C. This was allowed to warm to room temperature and stirred at this temperature for 1 hour leading to the formation of a thick suspension. This was then subsequently cooled to −78° C., where a solution of 2.00 g (10.3 mmol) of trimethyltin chloride in 25 mL of THF was added dropwise. This was allowed to warm to room temperature and stirred overnight. The mixture was poured into a separation funnel containing 200 mL de-ionized (DI) water. To this was added 300 mL of hexane and the organic layer was separated. The organic layer was further washed with 5×100 mL DI water. The organic layer was dried over anhydrous $MgSO_4$ and decolorized with activated charcoal. The mixture was filtered and the solvent was removed via rotovap. The molecule was further dried by pulling vacuum on a high vac line for 48 hours yielding 3.4 g (95.7%) of a pale green oil. Attempts to further purify via chromatography with silica or alumina led to significant decomposition. $^1$H NMR (400 MHz, $CDCl_3$): δ=7.09 (m, 2H), 1.50-1.35 (m, 4H), 1.35-1.17 (m, 36H), 0.92-0.83 (m, 10H), 0.39 (m, 18H). $^{13}$C NMR (125 MHz, $C_6D_6$): δ=155.22, 143.32, 137.89, 137.85, 33.48, 32.16, 29.93, 29.89, 29.84, 29.79, 29.60, 29.46, 24.52, 22.93, 14.35, 12.23, −7.88. $^{119}$Sn NMR (184 MHz, $CDCl_3$): δ=−27.84 ($^1J_{SnC}$=184 Hz). HRMS (EI) m/z, calcd for $C_{38}H_{70}S_2Si^{116}Sn_2$ ($M^+$): 850.2723; found: 850.2710.

Synthesis of 5,5'-Bis(benzo[2,1,3]thiadiazole)-3,3'-Di-n-dodecylsilylene-2,2'-bithiophene (1)

A 5 mL microwave tube was charged with 4-bromo-benzo[2,1,3]thiadiazole (0.186 g, 0.87 mmol), 5,5'Bis(trimethylstannyl)-3,3'-Di-n-dodecylsilylene-2,2'-bithiophene ($DTS_{C12}$) (0.371 g, 0.43 mmol), $Pd(PPh_3)_4$ (0.010 g, 0.009 mmol), toluene (3 mL), and sealed with a teflon cap. The reaction mixture was heated to 120° C. for 3 minutes, 140° C. for 3 minutes, and 170° C. for 24 minutes, using a Biotage microwave reactor. Upon cooling, all volatiles were removed in vacuo to give the crude product as a red solid. The crude product was subjected to flash chromatography on a silica gel column using hexane as the eluent. After removal of the solvent the product was precipitated using methanol (50 mL) and the red solid collected by filtration. Recovered yield: 295 mg (85%). $^1$H NMR ($CD_2Cl_2$): δ 8.20 (s, 2H, thiophene-CH), 7.87 (d, $^3J_{H-H}$=8 Hz, 2H, benzothiadiazole-p-CH), 7.83 (d, $^3J_{H-H}$=8 Hz, 2H, benzothiadiazole-o-CH), 7.61 (dd, $^3J_{H-H}$=7 Hz, $^3J_{H-H}$=7 Hz, 2H, benzothiadiazole-m-CH), 1.51 (m, 4H, $CH_2$), 1.35 (m, 4H, $CH_2$), 1.25-1.19 (m, 32H, $CH_2$), 1.07 (m, 4H, $SiCH_2$), 0.85 (t, 6H, $^3J_{H-H}$=7 Hz, $CH_3$). $^{13}$C{$^1$H} NMR ($CD_2Cl_2$): 156.20, 152.70, 151.11, 144.36, 141.39, (s, quaternary), 131.29 (s, thiophene-CH), 130.25 (s, benzothiadiazole-m-CH), 128.29 (s, quaternary), 125.17 (s, benzothiadiazole-o-CH), 120.01 (s, benzothiadiazole-p-CH), 33.71 (s, $CH_2$), 32.45 (s, $CH_2$), 30.25 (s, $CH_2$), 30.22 (s, $CH_2$), 30.18 (s, $CH_2$), 30.13 (s, $CH_2$), 29.89 (s, $CH_2$), 29.79 (s, $CH_2$), 24.79 (s, $CH_2$), 23.23 (s, $CH_2$), 14.42 (s, $CH_3$), 12.45 (s, $SiCH_2$). Anal. Calcd. for $C_{44}H_{58}N_4S_4Si$: C, 66.12; H, 7.31; N, 7.01. Found: C, 66.0; H, 7.06; N, 6.93%. UV-vis: $λ_{max}$=503 nm.

Characterization of (2)

To a clear solution of $B(C_6F_5)_3$ (0.020 g, 0.039 mmol) in $CH_2Cl_2$ (5 mL) was added a red solution of 1 (0.031 g, 0.039 mmol) in $CH_2Cl_2$ (5 mL). The resulting deep green solution was allowed to stir for 30 minutes at room temperature. The solvent was removed in vacuo to give a dark green solid. Recovered yield: 45 mg (88%). Solution NMR showed the existence of 1, 2, and 3 in a 1:2:1 ratio at −30° C. Spectral resonances attributed to species 2 are reported below: $^1$H NMR ($CD_2Cl_2$): δ 8.20 (s, 2H, thiophene-CH), 7.93 (br s, 2H, BT-CH), 7.93 (br s, 1H, BT-CH), 7.81 (br s, 1H, BT-CH), 7.66 (br s, 1H, BT-CH), 7.53 (br s, 1H, BT-CH), 1.50 (br, 4H, $CH_2$), 1.35 (br, 4H, $CH_2$), 1.25 (br, 32H, $CH_2$), 1.09 (m, 4H, $SiCH_2$), 0.86 (m, 6H, $CH_3$). $^1$H NMR ($CD_2Cl_2$, −30° C.): δ 8.16 (s, 1H, thiophene-CH), 8.15 (s, 1H, thiophene-CH), 7.88

(m, 1H, BT-CH), 7.84 (m, 1H, BT-CH), 7.79 (m, 1H, BT-CH), 7.77 (m, 1H, BT-CH), 7.61 (dd, 1H, $^3J_{H-H}$=9 Hz, $^3J_{H-H}$=7 Hz BT-CH), 7.46 (d, 1H, $^3J_{H-H}$=9 Hz, BT-CH), 1.39 (m, 4H, CH$_2$), 1.26 (m, 4H, CH$_2$), 1.10 (m, 32H, CH$_2$), 0.98 (m, 4H, SiCH$_2$), 0.77 (t, 6H, $^3J_{H-H}$=9 Hz, CH$_3$). $^{11}$B {$^1$H} NMR (CD$_2$Cl$_2$): δ –6.0 (bs). $^{13}$C{$^1$H} NMR (CD$_2$Cl$_2$, –30° C.): partial (quaternary carbons unidentified): δ 136.80 (s, BT-CH), 132.72 (s, thiophene-CH), 130.63 (s, BT-CH), 130.00 (s, BT-CH), 125.24 (s, BT-CH), 125.01 (s, BT-CH), 119.45 (s, BT-CH), 113.74 (s, BT-CH), 147.50 (dm, $^1J_{C-F}$=250 Hz, CF), 138.15 (dm, $^1J_{C-F}$=245 Hz, CF), 136.94 (dm, $^1J_{C-F}$=245 Hz, CF), 116.60 (br, quaternary, BC), 33.56 (s, CH$_2$), 32.20 (s, CH$_2$), 30.15-29.92 (m, 4×CH$_2$), 29.65 (s, CH$_2$), 29.55 (s, CH$_2$), 24.43 (m, CH$_2$), 22.95 (s, CH$_2$), 14.30 (s, CH$_3$), 11.76 (m, SiCH$_2$). $^{19}$F NMR (CD$_2$Cl$_2$): δ –125.2 (s, 1F, ortho-C$_6$F$_5$), –130.3 (br, 1F, ortho-C$_6$F$_5$), –131.0 (s, 1F, ortho-C$_6$F$_5$), –132.0 (br, 1F, ortho-C$_6$F$_5$), –134.0 (br, 1F, ortho-C$_6$F$_5$), –137.5 (br, 1F, ortho-C$_6$F$_5$), –154.5 (s, 1F, para-C$_6$F$_5$), –156.1 (br, 1F, para-C$_6$F$_5$), –157.7 (br, 1F, para-C$_6$F$_5$), –161.5 (br, 1F, meta-C$_6$F$_5$), –162.1 (br, 1F, meta-C$_6$F$_5$), –162.7 (br, 3F, meta-C$_6$F$_5$). $^{19}$F NMR (CD$_2$Cl$_2$, –50° C.): δ –125.12 (m, 1F, $^3J_{F-F}$=22 Hz, ortho-C$_6$F$_5$), –130.54 (m, 1F, $^3J_{F-F}$=24 Hz, ortho-C$_6$F$_5$), –131.39 (m, 2F, $^3J_{F-F}$=24 Hz, ortho-C$_6$F$_5$), –134.00 (m, 1F, =20 Hz, ortho-C$_6$F$_5$), –137.41 (m, 1F, $^3J_{F-F}$=22 Hz, ortho-C$_6$F$_5$), –154.26 (m, 1F, $^3J_{F-F}$=20 Hz, para-C$_6$F$_5$), –155.72 (m, 1F, $^3J_{F-F}$=24 Hz, para-C$_6$F$_5$), –157.57 (m, 1F, $^3J_{F-F}$=24 Hz, para-C$_6$F$_5$), –161.37 (m, 1F, $^3J_{F-F}$=20 Hz, meta-C$_6$F$_5$), –162.14 (m, 1F, $^3J_{F-F}$=22 Hz, meta-C$_6$F$_5$), –163.01 (m, 1F, $^3J_{F-F}$=22 Hz, meta-C$_6$F$_5$), –163.56 (m, 1F, $^3J_{F-F}$=22 Hz, meta-C$_6$F$_5$), –163.94 (m, 1F, $^3J_{F-F}$=24 Hz, meta-C$_6$F$_5$), –164.25 (m, 1F, $^3J_{F-F}$=24 Hz, meta-C$_6$F$_5$).

Synthesis of (3)

To a clear solution of B(C$_6$F$_5$)$_3$ (0.040 g, 0.078 mmol) in CH$_2$Cl$_2$ (5 mL) was added a red solution of 1 (0.031 mg, 0.039 mmol) in CH$_2$Cl$_2$ (5 mL). The resulting deep blue solution was allowed to stir for 30 minutes at room temperature. The solvent was removed in vacuo to give the product as a blue solid. Recovered yield: 58 mg (82%). Upon addition of excess B(C$_6$F$_5$)$_3$ (4 equivalents total) to 3, no change in the $^1$H or $^{19}$F spectrum was observed from 25 to –50° C. $^1$H NMR (CD$_2$Cl$_2$, 500 MHz, 300K): δ 8.19 (s, 2H, thiophene-CH), 7.97 (d, $^3J_{H-H}$=10 Hz, 2H, benzothiadiazole-p-CH), 7.83 (dd, $^3J_{H-H}$=10 Hz, $^3J_{H-H}$=10 Hz, 2H, benzothiadiazole-m-CH), 7.55 (d, $^3J_{H-H}$=10 Hz, 2H, benzothiadiazole-o-CH), 1.46 (m, 4H, CH$_2$), 1.33 (m, 4H, CH$_2$), 1.25 (m, 4H, CH$_2$), 1.23-1.19 (m, 28H, CH$_2$), 1.08 (m, 4H, SiCH$_2$), 0.82 (t, 6H, $^3J_{H-H}$=7 Hz, CH$_3$). $^{11}$B {$^1$H} NMR (CD$_2$Cl$_2$, 160 MHz, 300K): δ –6.3 (bs). $^{13}$C{$^1$H} NMR (CD$_2$Cl$_2$, 125 MHz, 300K): 152.75, 152.39, 150.56 (s, quaternary), 149.50 (dm, $^1J_{C-F}$=245 Hz, CF), 146.15 (s, quaternary), 141.98 (dm, $^1J_{C-F}$=250 Hz, CF), 139.62, (s, quaternary), 137.60 (dm, $^1J_{C-F}$=250 Hz, CF), 136.86 (s, benzothiadiazole-m-CH), 133.22 (s, thiophene-CH), 130.78 (s, quaternary), 126.25 (s, benzothiadiazole-p-CH), 117.45 (br, quaternary, BC), 114.88 (s, benzothiadiazole-o-CH), 33.71 (s, CH$_2$), 32.48 (s, CH$_2$), 30.29 (s, CH$_2$), 30.26 (s, CH$_2$), 30.24 (s, CH$_2$), 30.12 (s, CH$_2$), 29.88 (s, CH$_2$), 29.76 (s, CH$_2$), 24.72 (s, CH$_2$), 23.24 (s, CH$_2$), 14.40 (s, CH$_3$), 12.28 (s, SiCH$_2$). $^{19}$F NMR (CD$_2$Cl$_2$, 470 MHz, 300K): δ –125.2 (s, 1F, ortho-C$_6$F$_5$), –130.5 (br, 1F, ortho-C$_6$F$_5$), –131.5 (s, 1F, ortho-C$_6$F$_5$), –134.0 (br, 1F, ortho-C$_6$F$_5$), –137.5 (br, 2F, ortho-C$_6$F$_5$), –154.2 (s, 1F, para-C$_6$F$_5$), –155.7 (br, 1F, para-C$_6$F$_5$), –157.5 (br, 1F, para-C$_6$F$_5$), –161.4 (br, 2F, meta-C$_6$F$_5$), –162.2 (br, 4F, meta-C$_6$F$_5$), –163.3 (br, 3F, meta-C$_6$F$_5$). $^{19}$F NMR (CD$_2$Cl$_2$, 470 MHz, 243K): δ –125.17 (m, 1F, $^3J_{F-F}$=24 Hz, ortho-C$_6$F$_5$), –130.53 (m, 1F, $^3J_{F-F}$=24 Hz, ortho-C$_6$F$_5$), –131.46 (m, 2F, $^3J_{F-F}$=28 Hz, ortho-C$_6$F$_5$), –134.04 (m, 1F, $^3J_{F-F}$=19 Hz, ortho-C$_6$F$_5$), –137.50 (m, 1F, $^3J_{F-F}$=19 Hz, ortho-C$_6$F$_5$), –154.27 (m, 1F, $^3J_{F-F}$=19 Hz, para-C$_6$F$_5$), –155.69 (m, 1F, $^3J_{F-F}$=24 Hz, para-C$_6$F$_5$), –157.54 (m, 1F, $^3J_{F-F}$=24 Hz, para-C$_6$F$_5$), –161.40 (m, 1F, $^3J_{F-F}$=19 Hz, meta-C$_6$F$_5$), –162.18 (m, 1F, $^3J_{F-F}$=24 Hz, meta-C$_6$F$_5$), –163.00 (m, 1F, $^3J_{F-F}$=19 Hz, meta-C$_6$F$_5$), –163.58 (m, 1F, $^3J_{F-F}$=19 Hz, meta-C$_6$F$_5$), –163.89 (m, 1F, $^3J_{F-F}$=24 Hz, meta-C$_6$F$_5$), –164.30 (m, 1F, $^3J_{F-F}$=24 Hz, meta-C$_6$F$_5$). UV-vis: $\lambda_{max}$=647 nm.

Recovery of (1)

Solutions of 2 or 3 were collected into a flask and excess PPh$_3$ was added. All volatiles were removed in vacuo. The resulting solids were slurred in hexanes and the filtered. The precipitate was discarded and the filtrate loaded onto silica and eluted with hexanes. The hexane fractions absorbing at 365 nm were collected and reduced to give crude 1. Precipitation in methanol and collection by filtration gave pure 1.

Synthesis of (4)

To a clear solution of B(C$_6$F$_5$)$_3$ (0.050 g, 0.098 mmol) in CH$_2$Cl$_2$ (5 mL) was added a colorless solution of 4-bromobenzo[2,1,3]thiadiazole (0.021 mg, 0.098 mmol) in CH$_2$Cl$_2$ (5 mL). The resulting yellow solution was allowed to stir for 30 minutes at room temperature. The solvent was removed in vacuo and the resulting solid washed with pentanes (2×10 mL) and dried under vacuum for 1 hour. The product was collected as a faint yellow solid. Recovered yield, 60 mg (85%). Crystal's suitable for X-ray diffraction were grown via slow diffusion of pentane into a concentrated solution of 4 in CH$_2$Cl$_2$. Upon addition of excess B(C$_6$F$_5$)$_3$ (3 equivalents total) to 4, no change in the $^1$H or $^{19}$F spectrum was observed from 25 to –50° C. $^1$H NMR (CD$_2$Cl$_2$): δ 8.02 (d, $^3J_{H-H}$=8 Hz, 1H, benzothiadiazole-p-CH), 7.71 (dd, $^3J_{H-H}$=8 Hz, $^3J_{H-H}$=8 Hz, 1H, benzothiadiazole-m-CH), 7.50 (d, $^3J_{H-H}$=8 Hz, 1H, benzothiadiazole-o-CH). {$^1$H} NMR (CD$_2$Cl$_2$): δ –5.5 (bs). $^{13}$C{$^1$H} NMR (CD$_2$Cl$_2$, –50° C.) partial: 152.79, (s, quaternary), 149.22 (s, quaternary), 148.90 (dm, $^1J_{C-F}$=250 Hz, CF), 148.22 (dm, $^1J_{C-F}$=250 Hz, CF), 146.55 (dm, $^1J_{C-F}$=245 Hz, CF), 141.73 (dm, $^1J_{C-F}$=245 Hz, CF), 140.85 (dm, $^1J_{C-F}$=250 Hz, CF), 138.99 (dm, $^1J_{C-F}$=240 Hz, CF), 137.05 (dm, $^1J_{C-F}$=245 Hz, CF), 136.74 (s, benzothiadiazole-m-CH), 134.01 (s, benzothiadiazole-p-CH), 131.90 (dm, $^1J_{C-F}$=250 Hz, CF), 117.22 (quaternary), 116.05 (s, benzothiadiazole-o-CH). $^{19}$F NMR (CD$_2$Cl$_2$): δ –125.2 (br, 1F, ortho-C$_6$F$_5$), –131.0 (br, 3F, ortho-C$_6$F$_5$), –135.2 (br, 1F, ortho-C$_6$F$_5$), –137.2 (br, 1F, ortho-C$_6$F$_5$), –154.5 (s, 1F, para-C$_6$F$_5$), –156.5 (br, 2F, para-C$_6$F$_5$), –161.6 (br, 2F, meta-C$_6$F$_5$), 163.8 (br, 4F, meta-C$_6$F$_5$). $^{19}$F NMR (CD$_2$Cl$_2$, –50° C.): δ –125.17 (m, 1F, $^3J_{F-F}$=22 Hz, ortho-C$_6$F$_5$), –130.58 (m, 1F, $^3J_{F-F}$=21 Hz, ortho-C$_6$F$_5$), –131.42 (m, 2F, $^3J_{F-F}$=24 Hz, ortho-C$_6$F$_5$), –134.13 (m, 1F, $^3J_{F-F}$=24 Hz, ortho-C$_6$F$_5$), –137.58 (m, 1F, $^3J_{F-F}$=24 Hz, ortho-C$_6$F$_5$), –153.99 (m, 1F, $^3J_{F-F}$=20 Hz, para-C$_6$F$_5$), –155.31 (m, 1F, $^3J_{F-F}$=20 Hz, para-C$_6$F$_5$), –157.27 (m, 1F, $^3J_{F-F}$=22 Hz, para-C$_6$F$_5$), –161.28 (m, 1F, $^3J_{F-F}$=20 Hz, meta-C$_6$F$_5$), –162.91 (m, 1F, $^3J_{F-F}$=20 Hz, meta-C$_6$F$_5$), –162.74 (m, 1F, $^3J_{F-F}$=20 Hz, meta-C$_6$F$_5$), –163.33 (m, 1F, $^3J_{F-F}$=20 Hz, meta-C$_6$F$_5$), –163.77 (m, 1F, $^3J_{F-F}$=22 Hz, meta-C$_6$F$_5$), –164.03 (m, 1F, $^3J_{F-F}$=22 Hz, meta-C$_6$F$_5$). UV-vis: $\lambda_{max}$=355 nm. X-Ray: C$_{24}$H$_3$B$_1$Br$_1$F$_{15}$N$_2$S$_1$. Space Group=P-1. Cell: a=10.82(15) Å, b=11.82(18) Å, c=12.36(18) Å, α=63.7(3)°, β=75.1(3)°, γ=84.1(4)°, V=1369(35) Å$^3$. R=0.0432%, R$_w$=0.1132%. GOF=1.027.

Results

Figure 5:
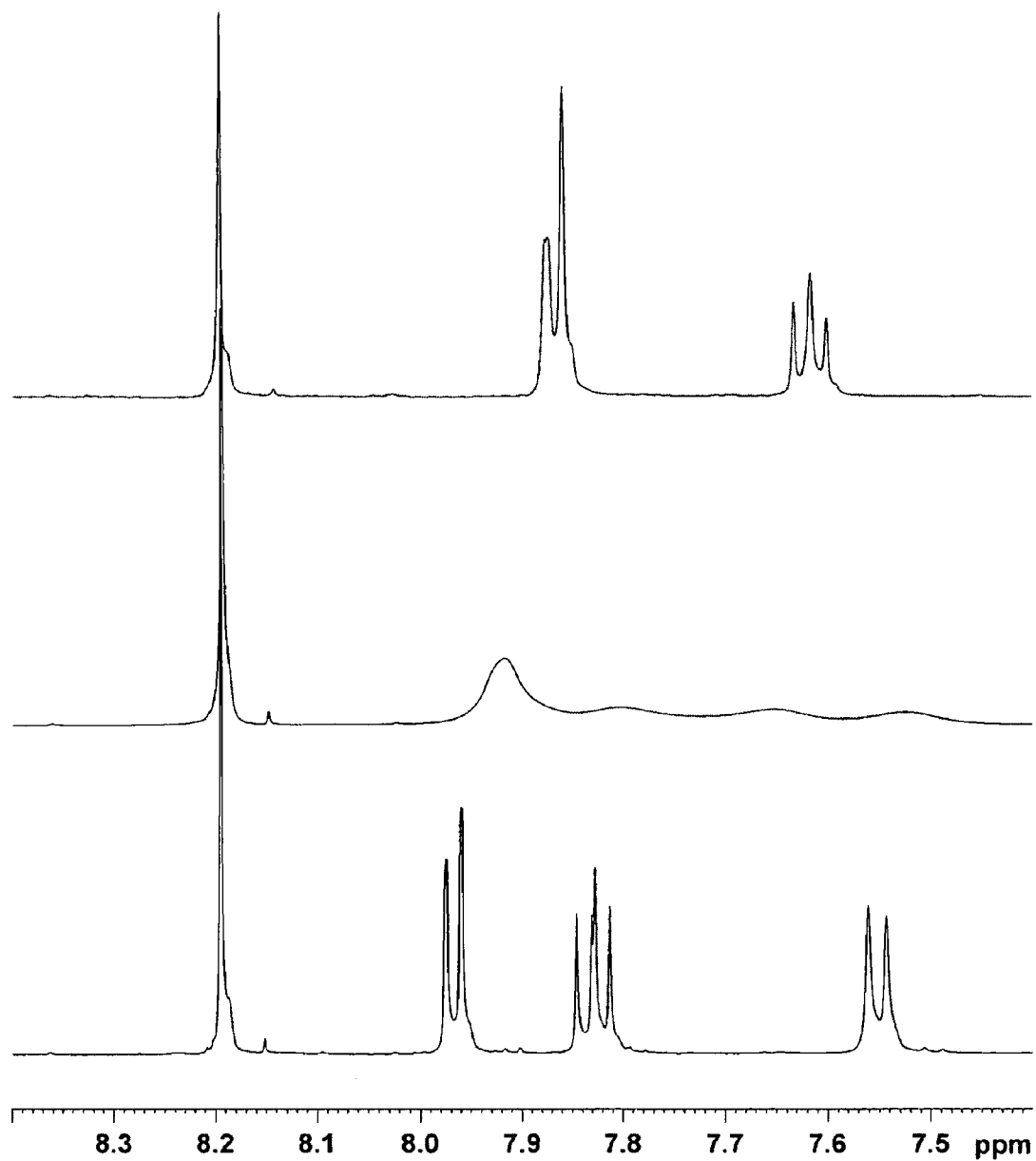
FIG. 5 is a plot showing $^1$H NMR spectra of the aromatic region of 1 (top), 1+$B(C_6F_5)_3$ (middle) and 3 (bottom) in $CD_2Cl_2$ at 30° C.

FIG. 5 shows $^1$H NMR spectra of the aromatic region of 1, 1+B(C$_6$F$_5$)$_3$ and 3 in CD$_2$Cl$_2$ at 30° C.

Figure 6:
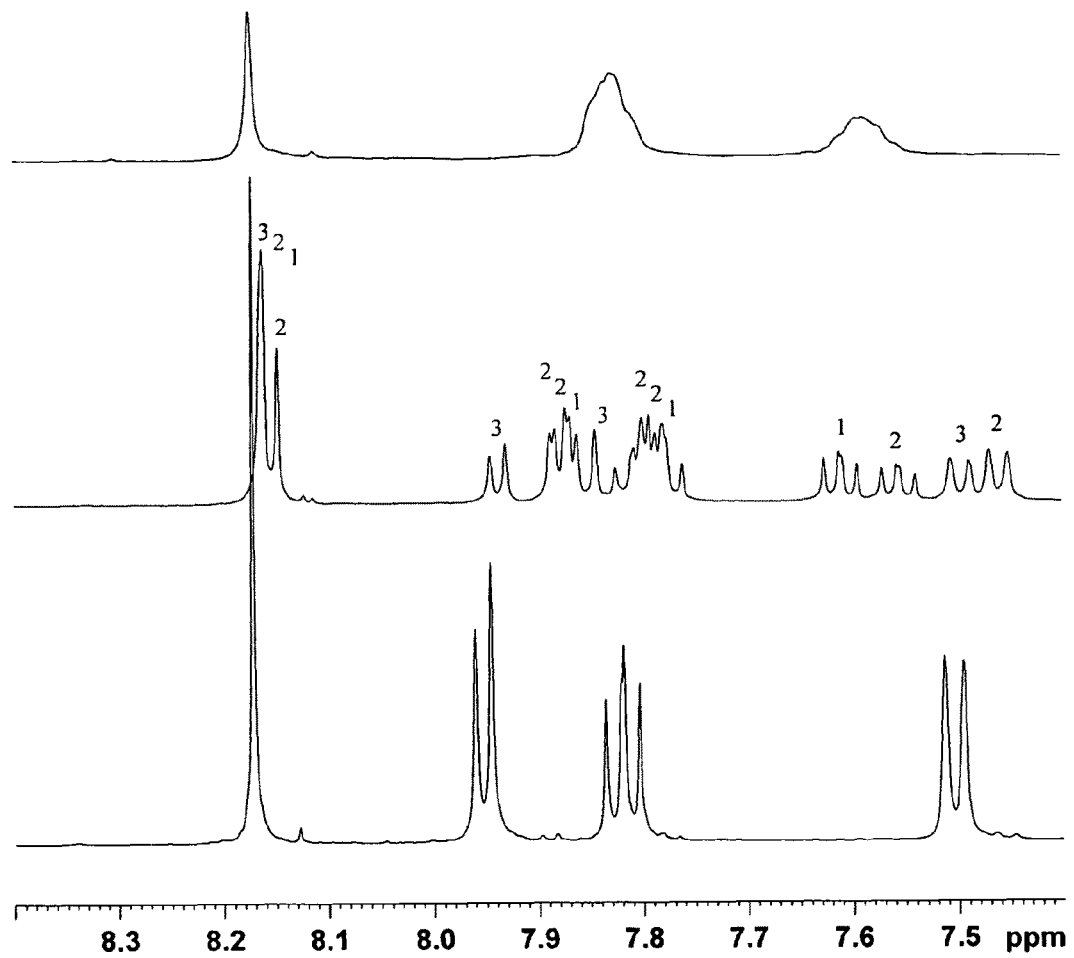
FIG. 6 is a plot of $^1$H NMR spectra of the aromatic region of 1 (top), 1+1$B(C_6F_5)_3$ (middle) and 3 (bottom) in $CD_2Cl_2$ at 30° C. Resonances for compounds 1, 2 and 3 are marked in the middle spectrum.

FIG. 6 shows $^1$H NMR spectra of the aromatic region of 1, 1+1B(C$_6$F$_5$)$_3$ and 3 in CD$_2$Cl$_2$ at 30° C. Resonances for compounds 1, 2 and 3 are also shown.

Figure 7:
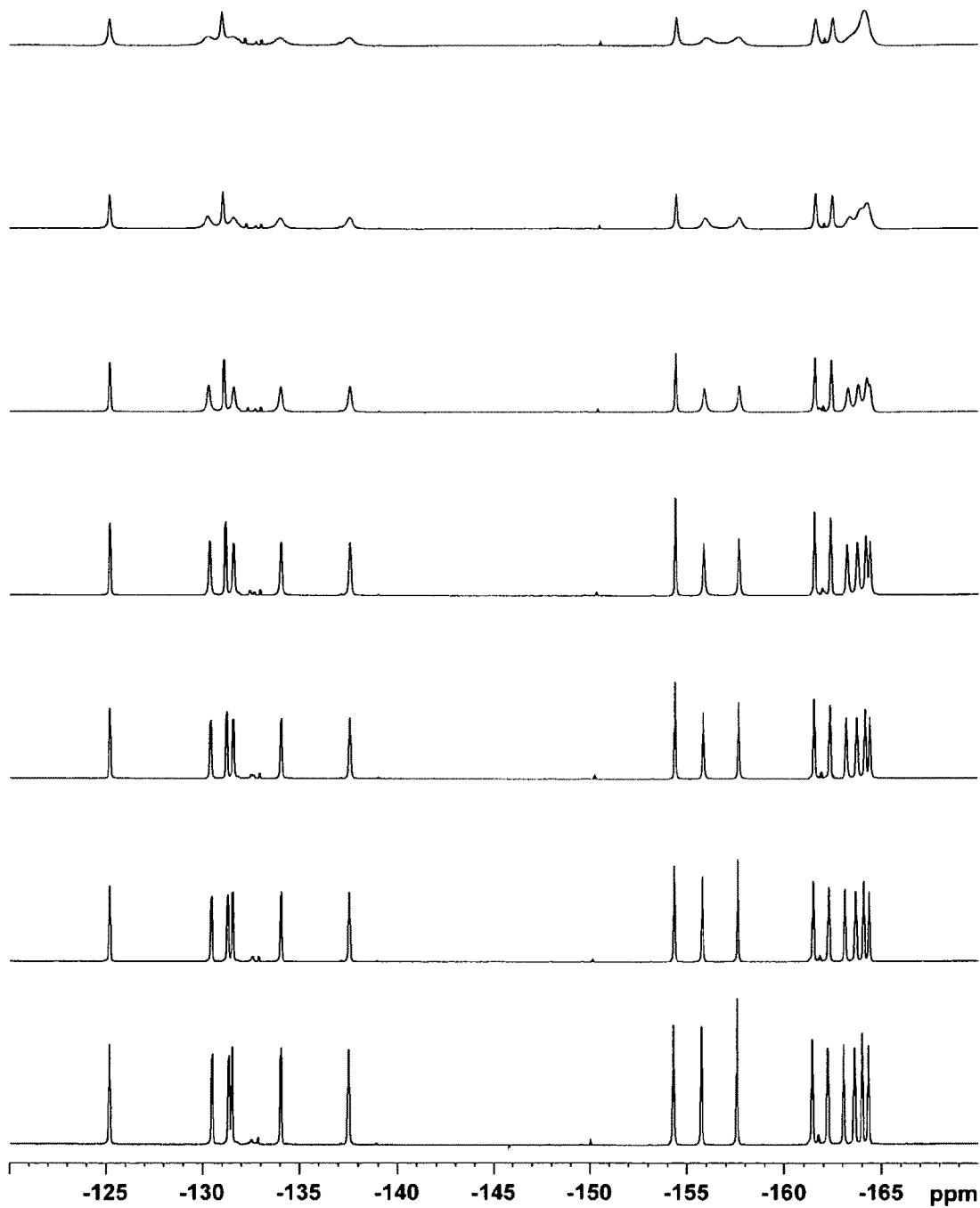
FIG. 7 is a plot of variable temperature $^{19}$F NMR spectra of 3. The top trace represents 30° C., and the bottom trace represents −30° C. The temperature decreases in 10° C. increments. Spectra below 0° C. show 15 in-equivalent F atoms.

FIG. 7 shows variable temperature $^{19}$F NMR spectra of 3. Spectra below 0° C. show 15 in-equivalent F atoms.

Table 1 shows UV-vis absorption data of 1 plus 2 equivalents of Lewis acid.

TABLE 1

UV-vis absorption data of 1 plus 2 equivalents of Lewis acid.
Molar absorptivity (ε) in L mol$^{-1}$cm$^{-1}$.

| Compound | log ε | $\lambda_{max}$ | $\Delta\lambda_{max}$ | $\lambda_{onset}$ | $\Delta\lambda_{onset}$ | Eg (opt) eV |
|---|---|---|---|---|---|---|
| 1 | 4.57 | 503 | — | 577 | — | 2.15 |
| 1(AlMe$_3$) | 4.44 | 573 | 70 | 686 | 109 | 1.81 |
| 1(AlCl$_2$Et) | 4.39 | 625 | 122 | 751 | 174 | 1.65 |
| 1(B(C$_6$F$_5$)$_3$) | 4.40 | 647 | 144 | 777 | 200 | 1.60 |
| 1(BCl$_3$) | 4.40 | 660 | 157 | 811 | 234 | 1.53 |
| 1(BBr$_3$) | 4.43 | 681 | 178 | 824 | 247 | 1.50 |

Figure 8:
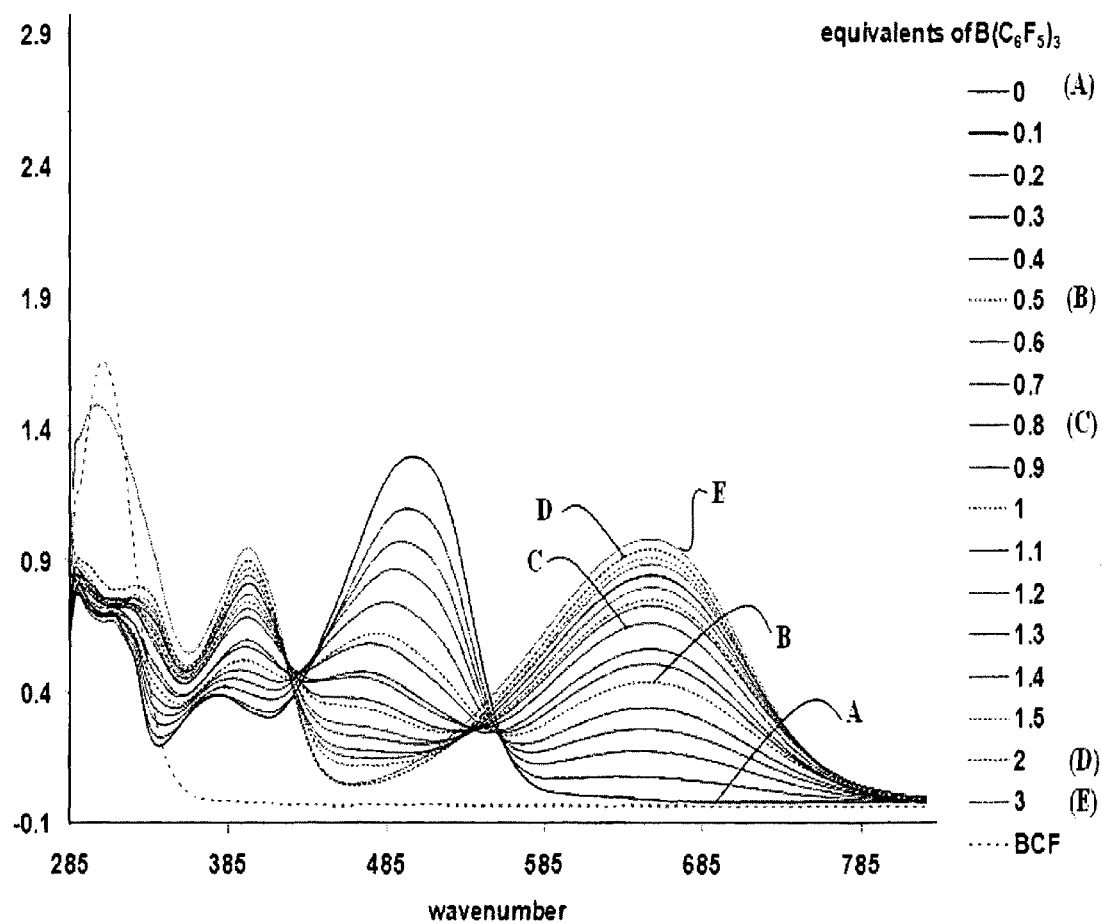
FIG. 8 is a plot of UV-visible absorption spectrum of 1+0-3 equivalents of $B(C_6F_5)_3$ in 1,2-dichlorobenzene solution at 25° C. under $N_2$. The concentration of 1 is 0.000378 M.

FIG. 8 shows UV-visible absorption spectrum of 1+0-3 equivalents of B(C$_6$F$_5$)$_3$ in 1,2-dichlorobenzene solution at 25° C. under N$_2$.

Figure 9A:
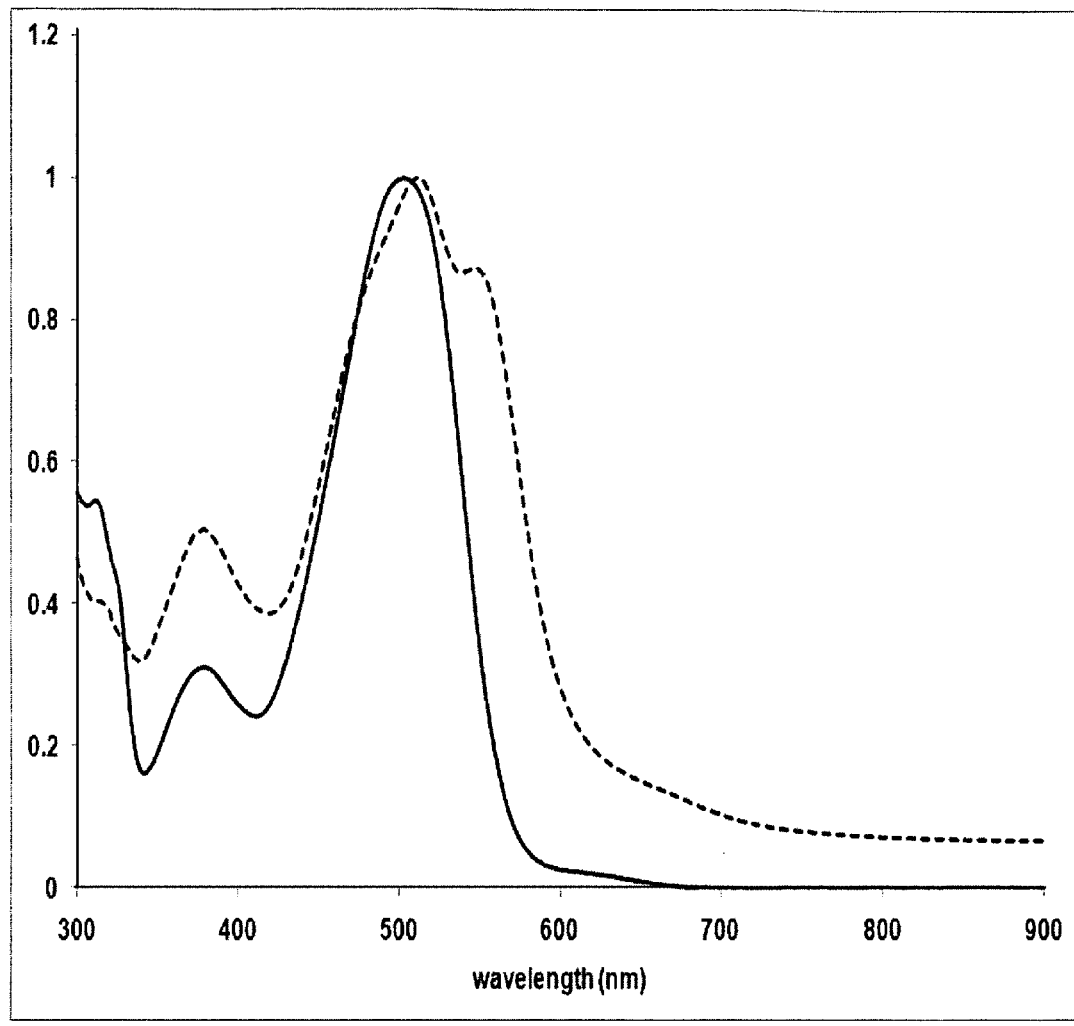
FIGS. 9A and 9B are plots of normalized UV-vis absorption of 1 (9A), and 3 (9B) as red and blue solutions (solid line) and films (dashed line), respectively. Films are cast from 20 mg mL$^{-1}$ solutions at 700 rpm. Solutions are in 1 mm cuvettes with a concentration of 0.000378 M with respect to 1. Spectra are recorded at 25° C. under an atmosphere of $N_2$.
Figure 9B:
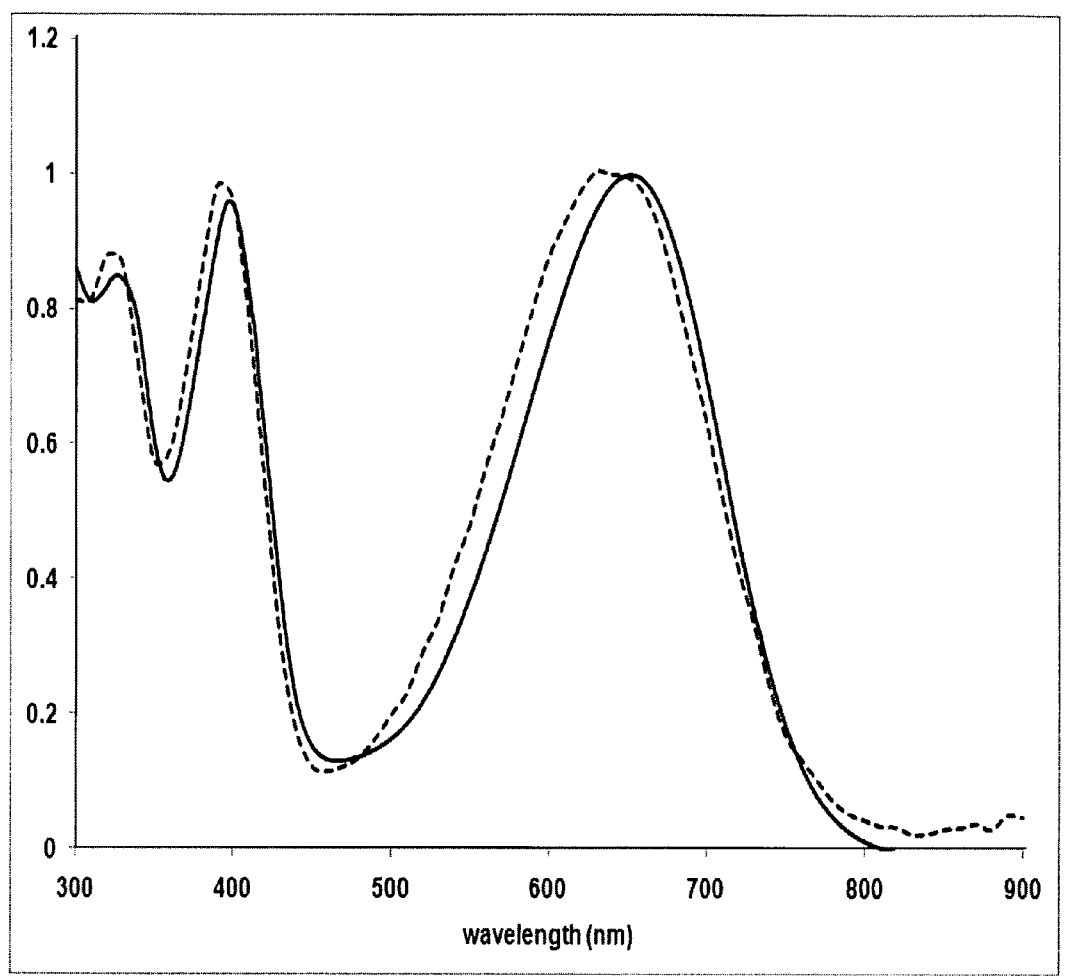

FIG. 9 shows normalized UV-vis absorption of 1, and 3 as red and blue solutions and films. Spectra were recorded at 25° C. under an atmosphere of N$_2$.

Example 3

Synthesis and Characterization of Conjugated Oligomers and Polymers

In the synthesis of novel oligomers based upon the pyridathiadiazole acceptor unit, a microwave Stille-cross coupling procedure was employed (Scheme 2).

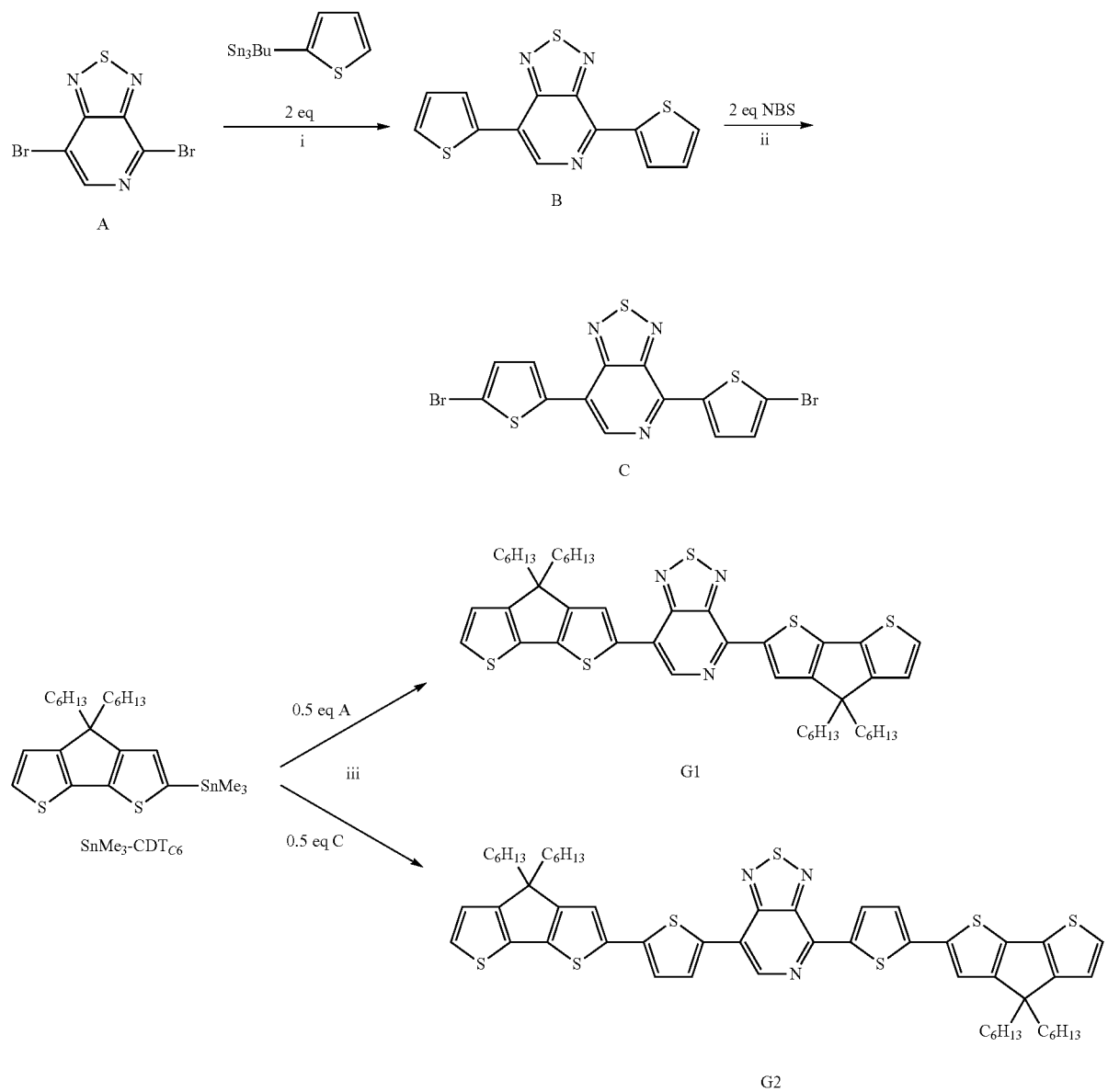

Conditions according to Scheme 2 are: i) microwave irradiation, 170° C. for 36 minutes, 5 mol% Pd(PPh$_3$)$_4$, toluene (3mL); ii) CHCl$_3$/DMF (2:1), 25° C. for 72 hours; iii) microwave irradiation, 170° C. for 36 minutes, 5 mol%,, toluene (3 mL).

The cyclopentadithiophene unit was functionalized with hexyl chains to ensure good solubility of the desired oligomers. The mono-stannyl precursor ($Me_3Sn\text{-}CDT_{C6}$) was prepared by treating 4,4-Bis(hexyl)cyclopentadithiophene with 1.1 equivalents of $^tBuLi$ in THF at −78° C., followed by quenching with $Me_3SnCl$ to give the product as a yellow oil in 98% yield. It should be mentioned that stannyl derivatives of this variety are difficult to purify as they are oily residues that readily decompose on silica to give starting material. Therefore it is important to be very accurate when measuring reagents.

Figure 17A:
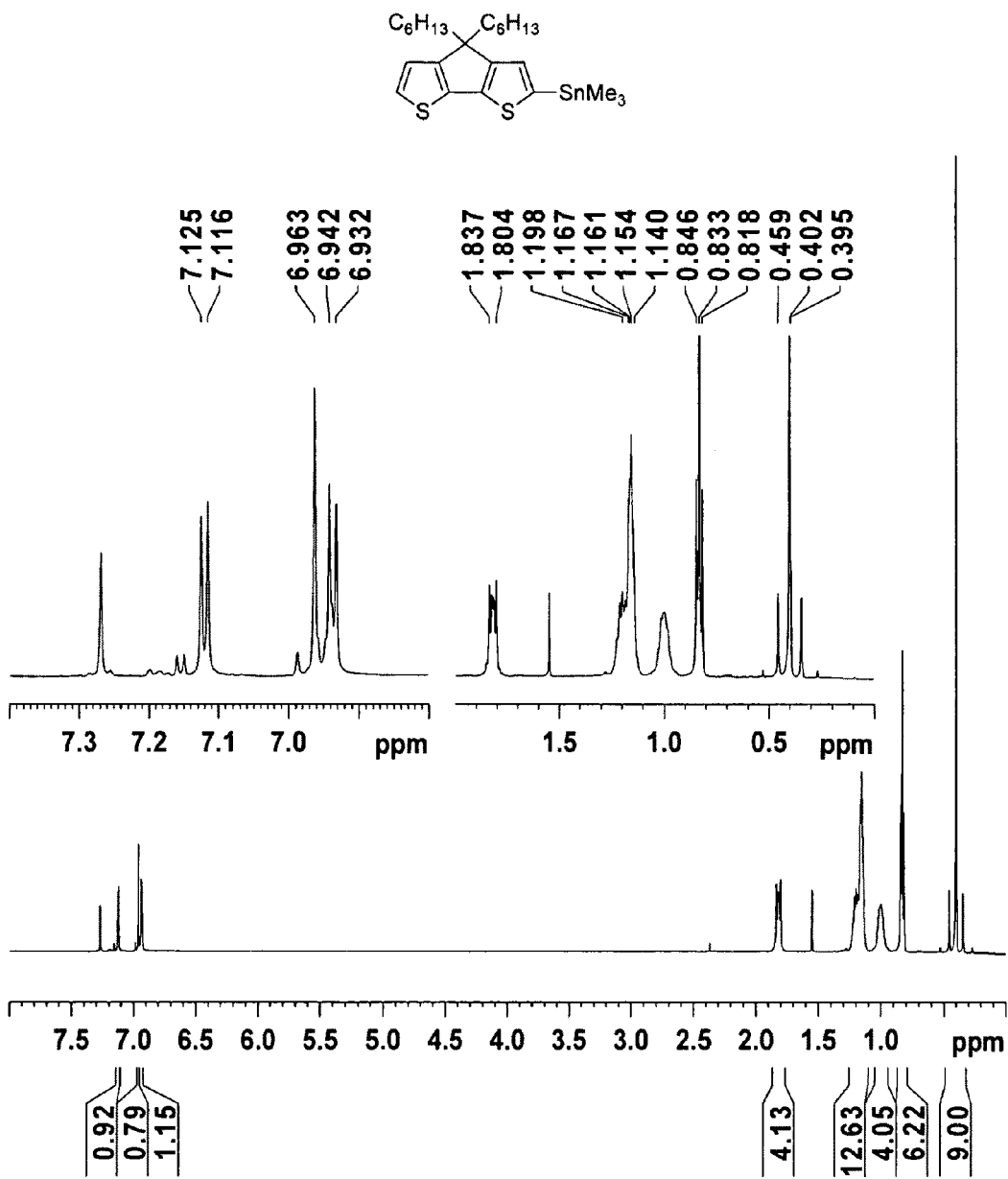
FIGS. 17A and 17B are $^1H$ and $^{13}C$ NMR spectra of $Me_3Sn$-$CDT_{C6}$ in $CDCl_3$ at 300K, where resonance at 1.5 ppm in $^1H$ spectrum is attributed to water from the solvent.
Figure 17B:
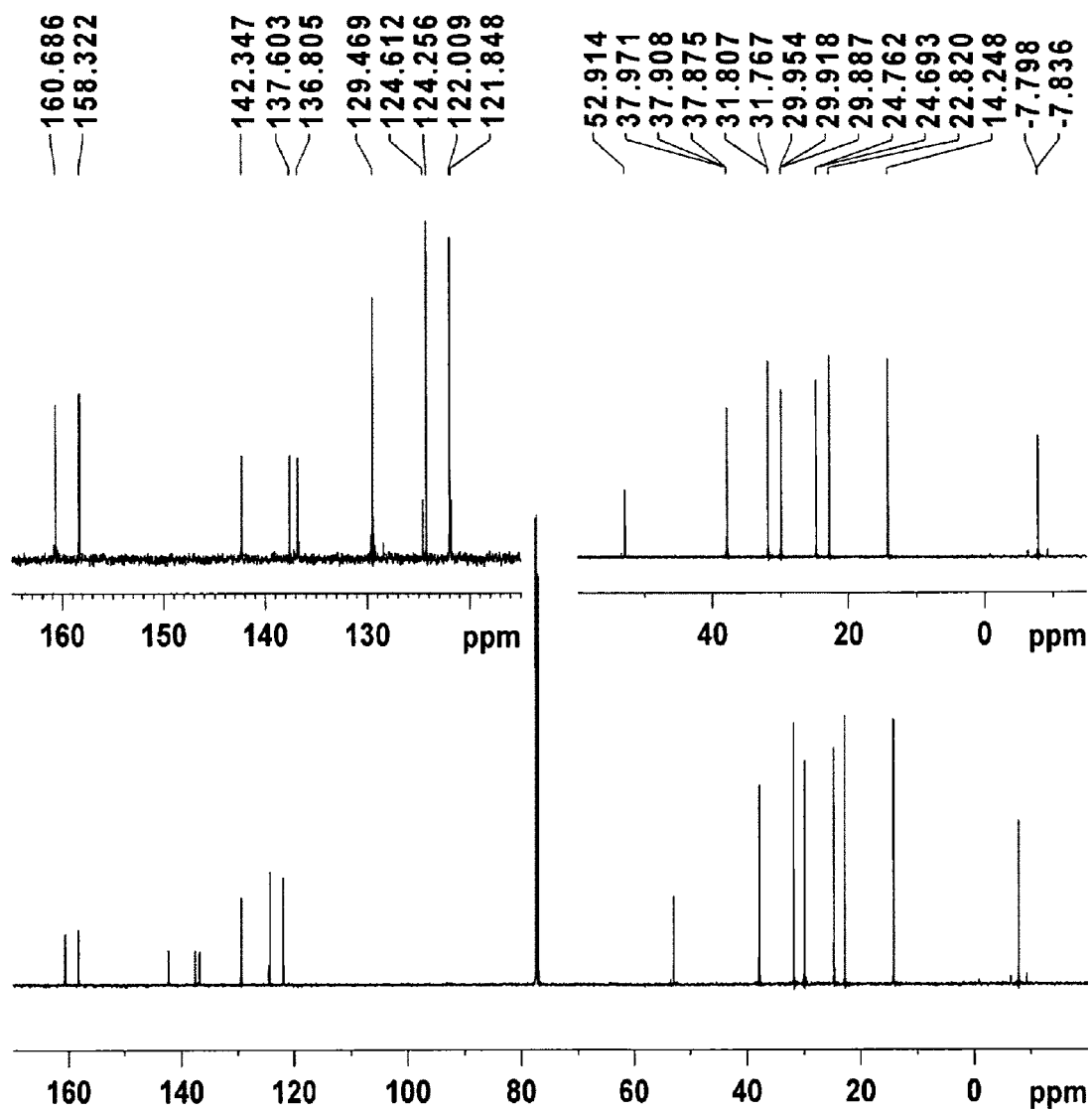

The $^1H$ NMR spectra of $Me_3Sn\text{-}CDT_{C6}$ exhibits 3 resonances in the aromatic region, two doublets each integrating for 1 proton are attributed to the protons in the 2 and 3 position, and a singlet with Sn satellites integrating for 1 proton, attributed to the proton in the 3' position (FIG. 17). The aliphatic region displays typical methyl and methylene resonances from 2-1 ppm for the hexyl substituents and a characteristic singlet with Sn satellites at 1 ppm integrating for 9 protons for the tin methyl groups. Acceptor A was purchased via a commercial source.

Figure 18:
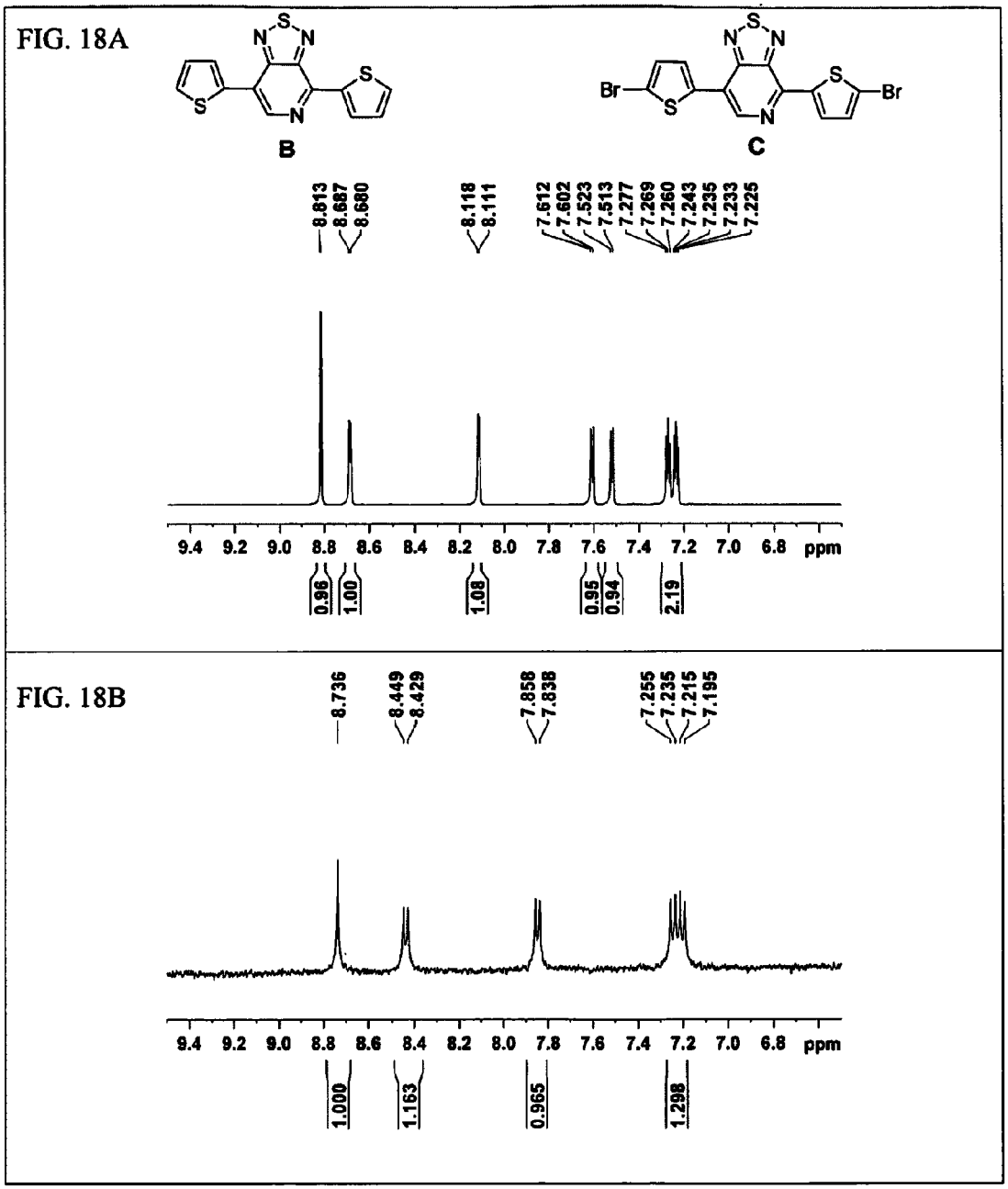
FIGS. 18A and 18B are $^1H$ NMR spectra of precursors B (18A) and C (18B) in $CD_2Cl_2$ at 300K.

Again referring to Scheme 2, the acceptor B was synthesized via a microwave Stille cross-coupling between 4,7-dibromo-pyridal[2,1,3]thiadiazole (A) and 2 equivalents of 2-(tributylstannyl)thiophene, in toluene at 170° C. for 36 minutes using $Pd(Ph_3)_4$ as the catalysts. Upon silica purification and precipitation, B was obtained as a red solid in 94% yield. The $^1H$ NMR spectrum of B (FIG. 18A) exhibits 7 in-equivalent aromatic proton resonances, consistent with the asymmetric nature of the molecule due to the nitrogen atom in the conjugated backbone. Acceptor B is soluble in most polar media. In o-dichlorobenzene, B has a maximum absorption and emission at 470 nm and 607 nm, respectively. Dibromination of B with >2 equivalents N-bromosuccinimide (NBS) proceeded cleanly in a dimethylformamide/chloroform (1:2) mixture over 72 hours at room temperature (use of 2 or less equivalents of NBS without chloroform yields primarily monobrominated species).

Acceptor C was purified by flash chromatography and obtained as a dark red solid in 79% yield. C is considerably less soluble than B in polar media. The $^1H$ NMR spectrum of C (FIG. 18B) shows only 5 aromatic proton resonances, 4 doublets and a singlet each integrating for one proton, consistent with bromination in the 5 and 5' positions.

Figure 19:
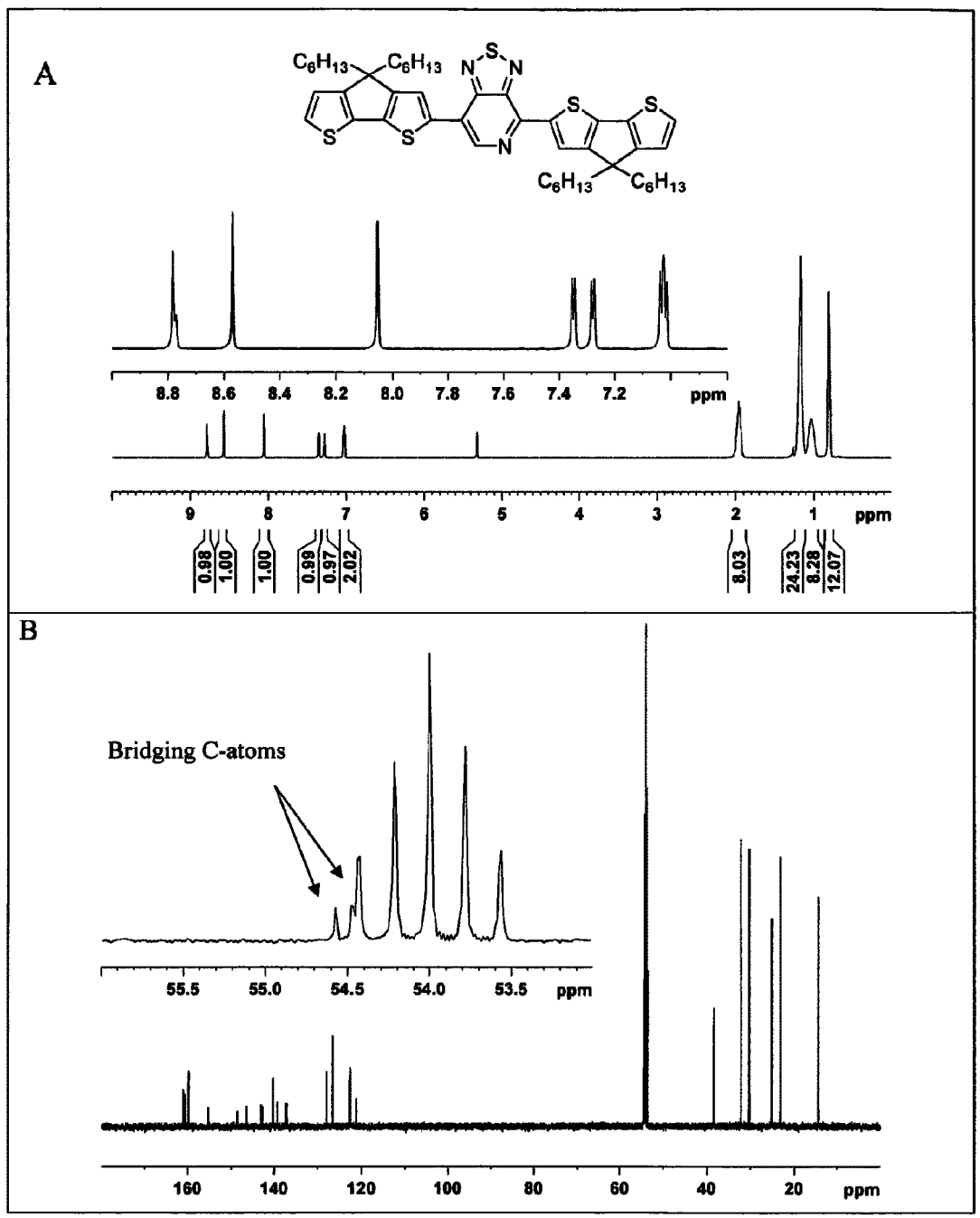
FIGS. 19A and 19B are $^1H$ (19A) and $^{13}C$ (19B) NMR spectra of G1 at 300K in $CD_2Cl_2$. The aromatic region of $^1H$ NMR spectra exhibits 7 in-equivalent aromatic proton resonances. Two in-equivalent thiophene bridging carbons atoms are observed in $^{13}C$ NMR spectra.
Figure 20:
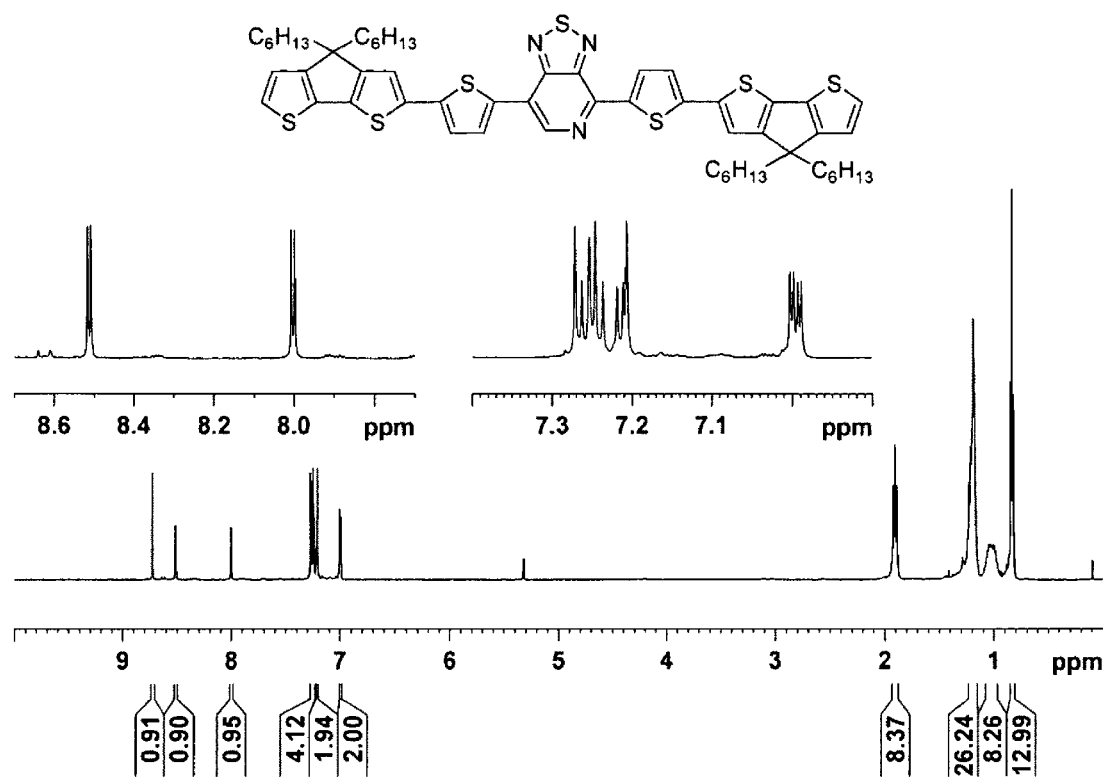
FIG. 20 is a panel of $^1H$ NMR spectra of G2 at 300K in $CD_2Cl_2$. The aromatic region of $^1H$ NMR spectra exhibits eleven in-equivalent aromatic proton resonances.

Oligomers G1 and G2 were synthesized via reaction of 2 equivalents of $Me_3Sn\text{-}CDT_{C6}$ with 1 equivalent of B or C, respectively (Scheme 2). Upon purification by flash chromatography and precipitation from methanol, G1 and G2, were obtained as purple solids in 72 and 77% yields, respectively. Both oligomers exhibit high solubility in most organic solvents, due to the presence of 4 hexyl chains in each molecule G1 and G2 were characterized by elemental analysis, multinuclear NMR, absorption, emission, and mass spectroscopy (FIGS. 19 and 20). In addition to four aliphatic resonances due to the hexyl side chains, G1 exhibits seven aromatic resonances in the $^1H$ NMR spectrum, consistent with the asymmetric structure (FIG. 19A). The asymmetry is also observed in the $^{13}C$ NMR, where two in-equivalent bridging carbon atoms are identified (FIG. 19B). Therefore it is clear that the pyridine nitrogen atom has a significant electronic impact on the conjugated structure. While oligomer G2 has an asymmetric structure, several of the aromatic thiophene protons have overlapping resonances in the $^1H$ NMR spectrum (FIG. 20), thus indicating a diminished electronic impact of the pyridine nitrogen on the π-conjugated structure further away from the PT core.

In conjunction with oligomers G1 and G2, three new polymeric derivatives were synthesized based on acceptors B and C and the CDT donor unit. The polymers have the following structures:

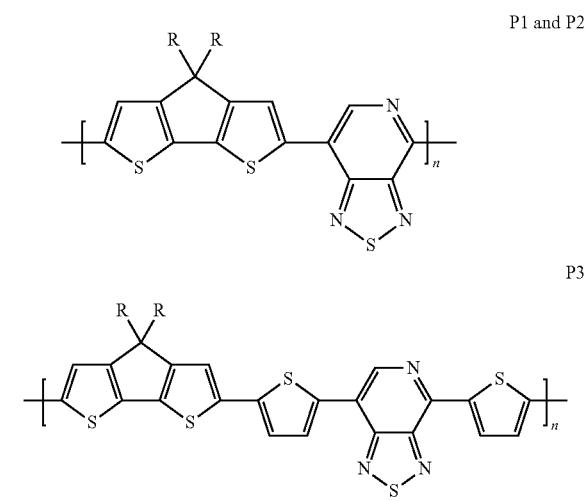

where, R is dodecil in P1, and R is 2-ethylhexyl in P2 and P3.

Figure 16:
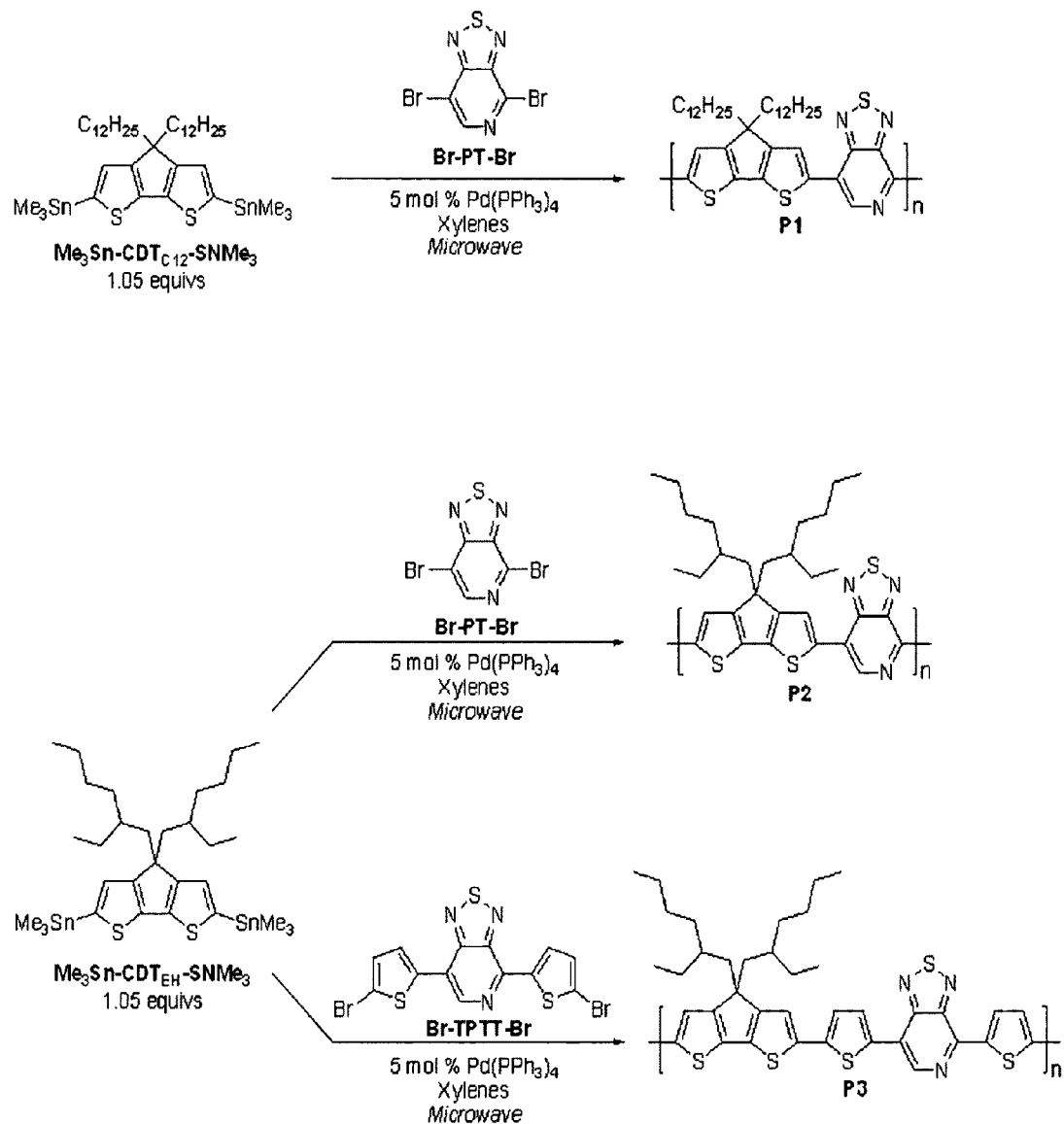
FIG. 16 is a diagram of Scheme 4, showing the synthesis of polymers P1, P2 and P3.
Figure 21:
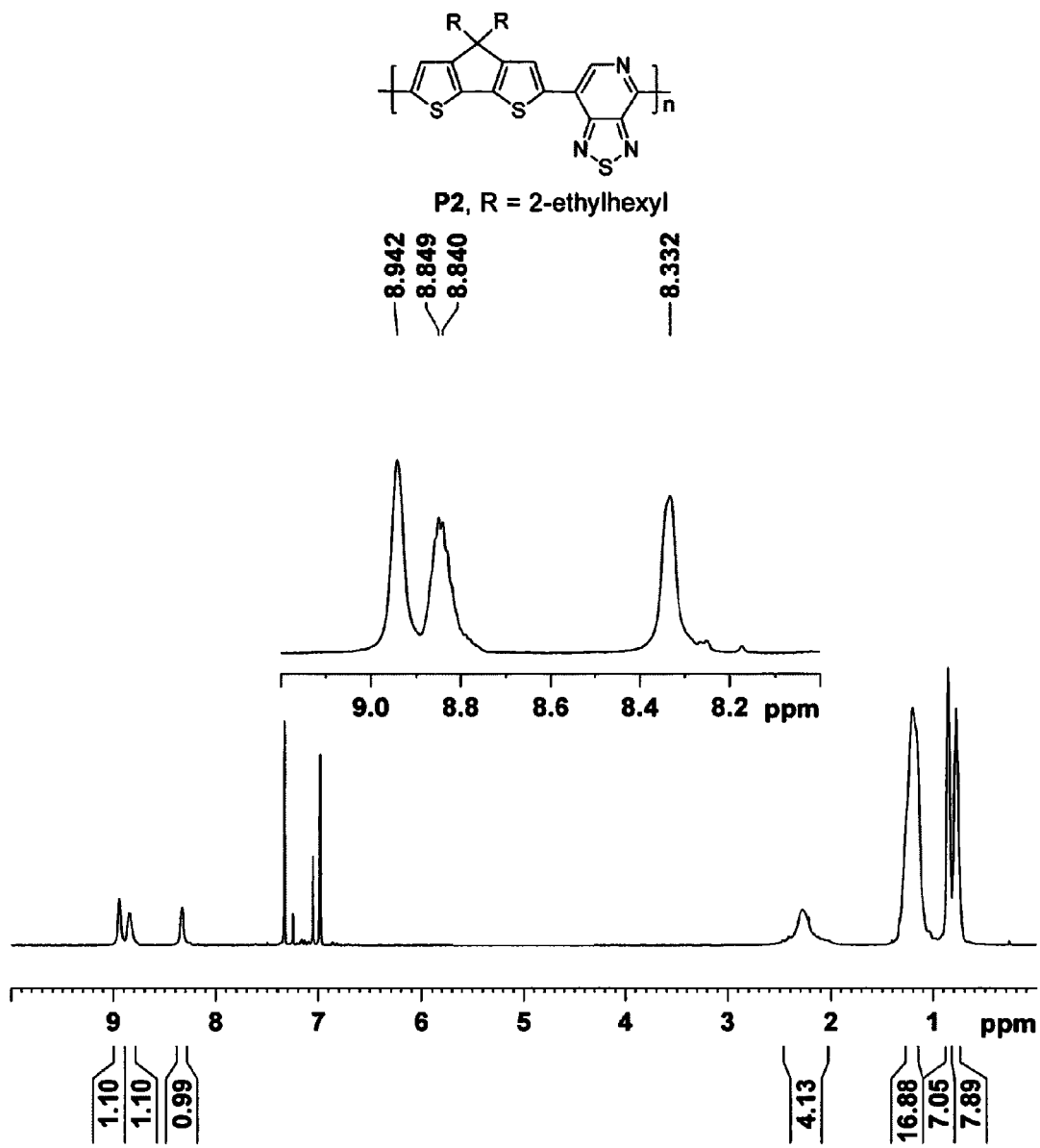
FIG. 21 is a panel of $^1H$ NMR spectra of polymer P2 at 300K in $C_6D_5Br$. The aromatic region of $^1H$ NMR spectra exhibits three aromatic proton resonances.
Figure 22:
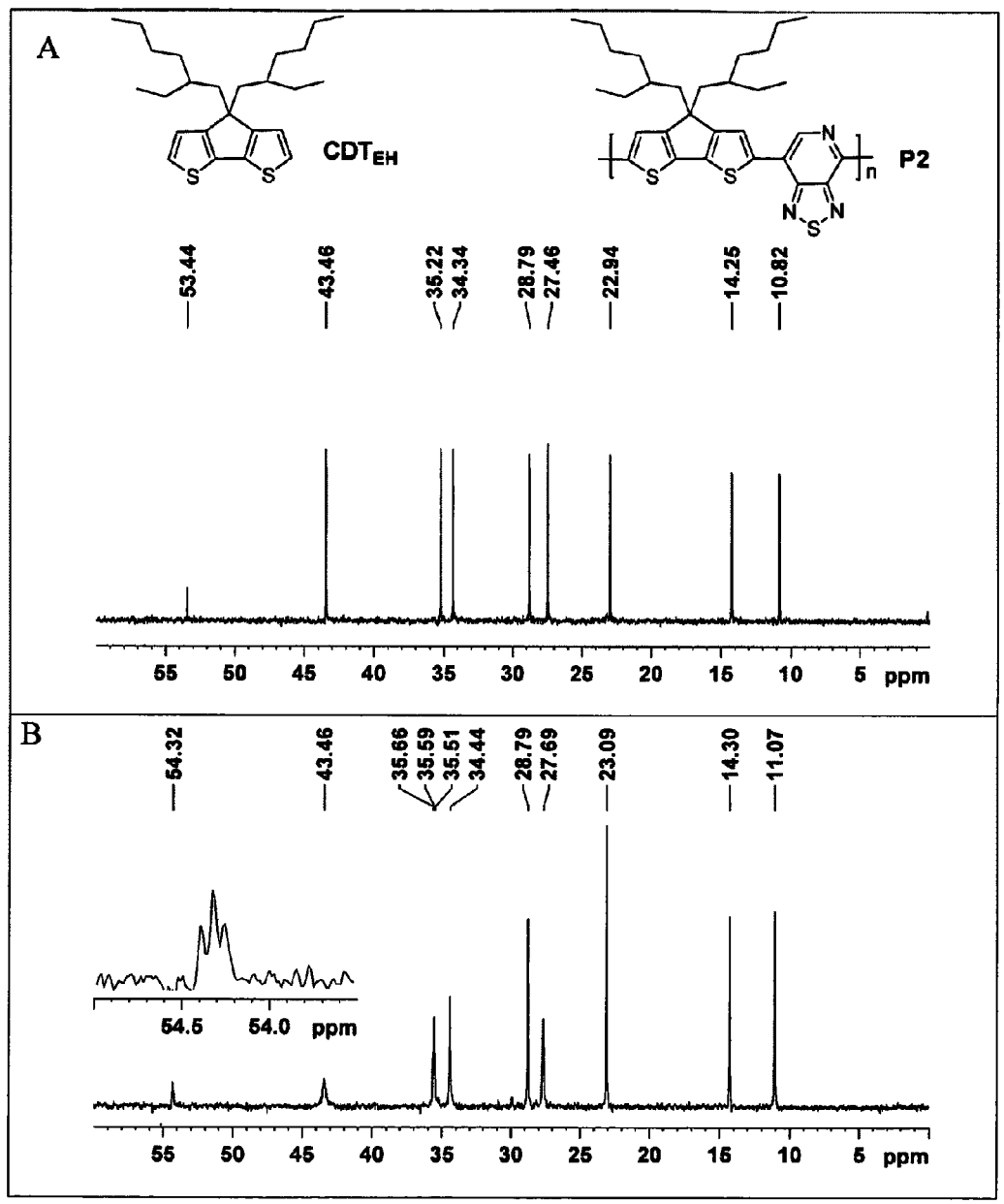
FIGS. 22A and 22B are aliphatic regions of the $^{13}C$ NMR spectra of polymer P2 (22B) and $CDT_{EH}$ (22A) at 300K in $C_6D_5Br$ and $CD_2Cl_2$, respectively. The resonances from 45 to 10 ppm are due to the methyl and methylene protons of the alkyl side chains. The resonances at 55 ppm are due to the bridging carbon atom.

Polymers P1, P2, and P3 were synthesized via a microwave assisted Stille polymerization procedure (FIG. 16, Scheme 4). Polymer P1 incorporates linear dodecil side chains on the CDT unit, while polymers P2 and P3 incorporate branched 2-ethylhexyl side chains on CDT unit. While both dodecil and 2-ethylhexyl side chains are known to give D-A copolymers good solubility in organic solvents, varying the steric bulk of the solubilizing side chains can have the effect of altering intermolecular interactions, and thus influence the long range packing and electronic coupling between polymer chains. After polymerization each polymer was dissolved in hot 1,2-dichlorbenzene, precipitated in methanol, and collected by centrifugation. Subsequent washing in a Soxhlet apparatus with methanol, hexanes, and acetone, followed by drying under high vacuum gave the desired polymers in greater than 75% yield. All polymers show good solubility in chlorobenzene and 1,2-dichlorobenzene (~10 mg per mL). The average number molecular weights of each polymer were determined by gel permutation chromatography (GPC) at 150° C. in 1,2,5-trichlorobenzene, and were found to be 20, 16, 18 kg $mol^{-1}$ for P1, P2, and P3, respectively. The polydispersity index (PDI) of each polymer was approximately 2. The $^1H$ and $^{13}C$ NMR spectra of P2 are shown in FIGS. 21 and 22. All polymers were examined by differential scanning calorimetry (DSC) and showed no transitions from −30 to 250° C., typical behavior for D-A polymers of this type.

Optical Properties

Figure 10A:
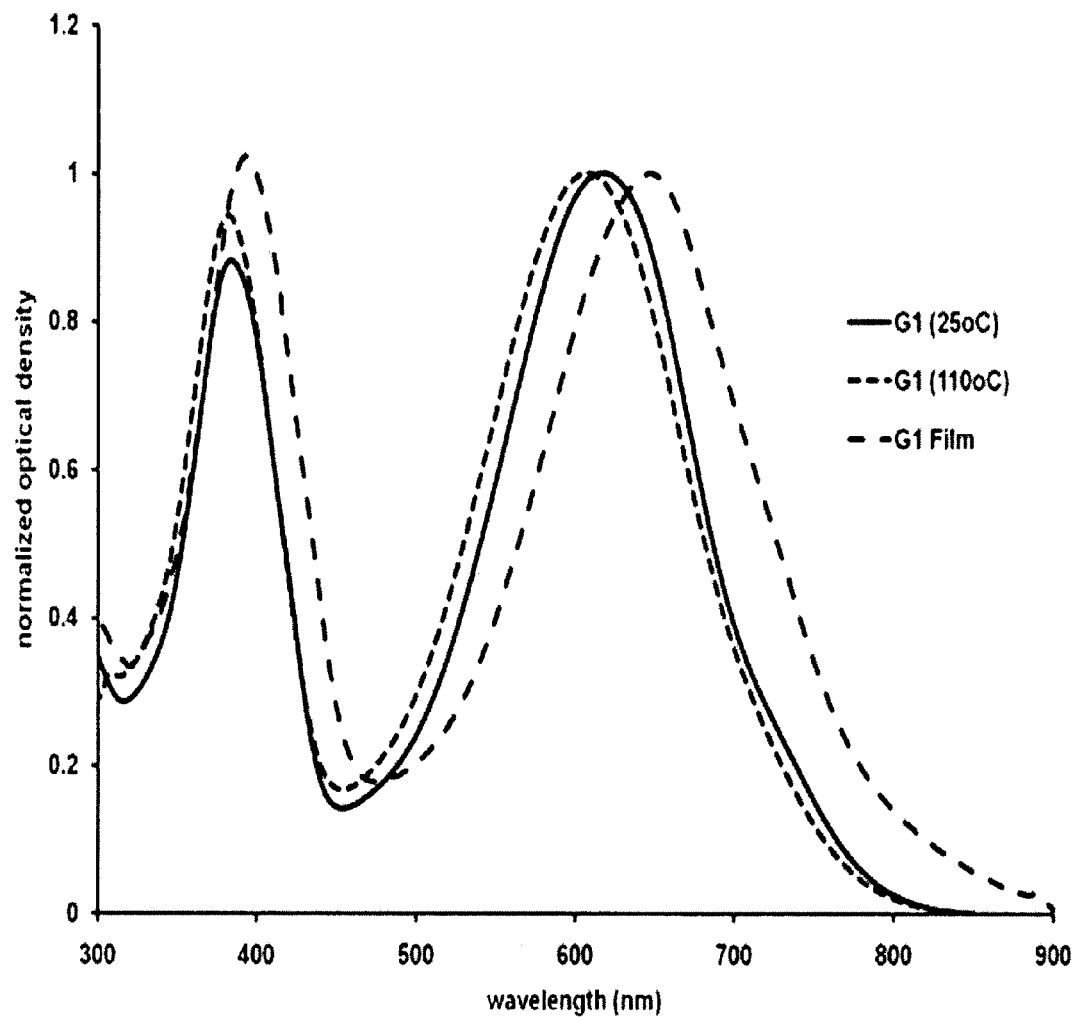
FIGS. 10A and 10B are plots of peak normalized absorption spectra for oligomers G1 (10B) and G2 (10A). Solution spectra at 25° C. (solid line) and 110° C. (small dashed line) are recorded in 1,2-dichlorobenzene. Film spectra (large dashed line) are obtained at 25° C.
Figure 10B:
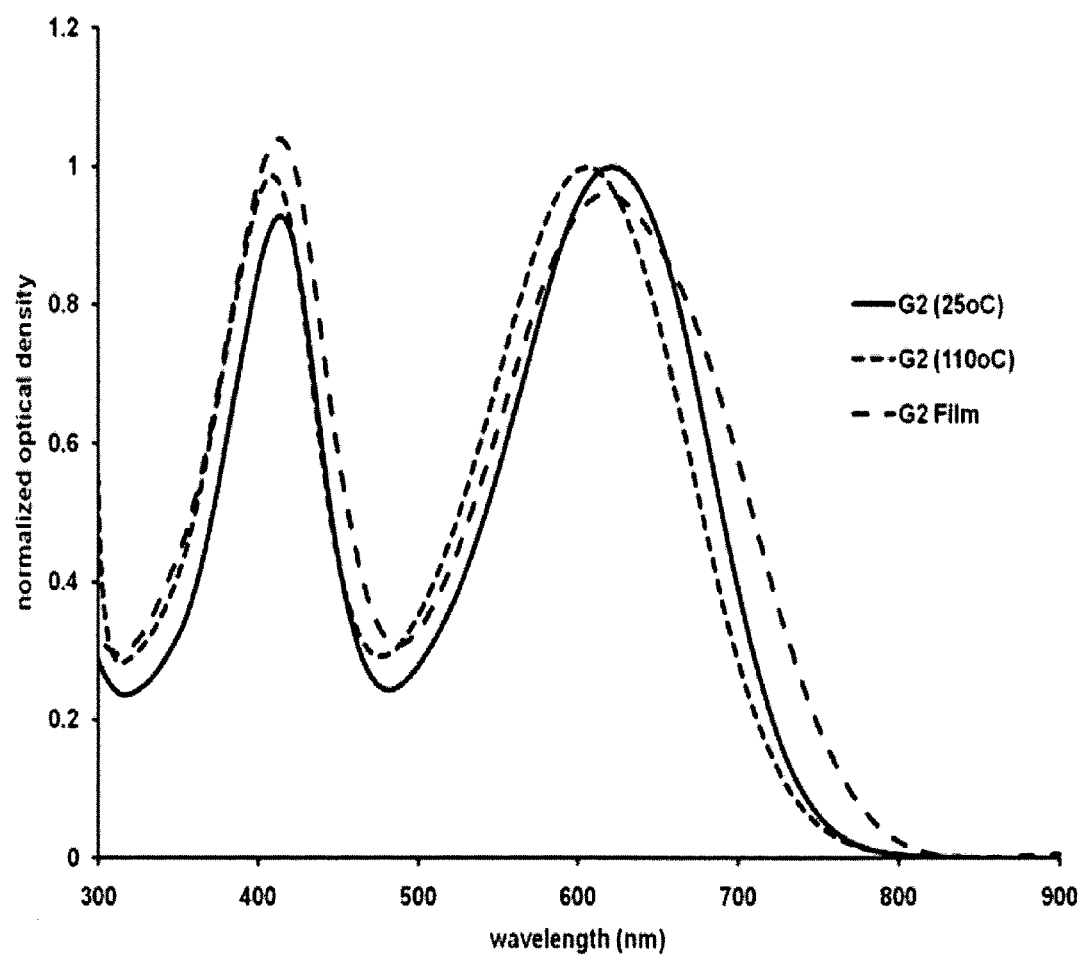

The normalized UV-vis-NIR absorption spectra of oligomers G1 and G2 are shown in FIG. 10 with all relevant data summarized in Table 2.

TABLE 2

Optical Data

| Compound | $\lambda_{max}$ (nm)* ($\epsilon_{max}$ [M$^{-1}$cm$^{-1}$]) | $\lambda_{onset}$ (nm)* | $\lambda_{max}$ (nm)** | $\lambda_{onset}$ (nm)** | Bandgap [eV] |
|---|---|---|---|---|---|
| G1 | 618 (35440) | 766 | 646 | 790 | 1.57 |
|    | 386 (30670) |     | 390 |     |      |
| G2 | 626 (37500) | 742 | 626 | 768 | 1.61 |
|    | 418 (30520) |     | 416 |     |      |
| P1 | 830 (29410)* | 1100 | 880 | 1130 | 1.10 |
|    | 435 (10420)* |      | 440 |      |      |
| P2 | 805 (44980)* | 890 | 830 | 944 | 1.31 |
|    | 420 (15410)* |     | 412 |     |      |
| P3 | 680 (38120)* | 855 | 690 | 875 | 1.42 |
|    | 450 (22450)* |     | 452 |     |      |

$\epsilon$ of polymers determined using molecular weight of repeat unit;
*solution (1,2-dichlorobenzene);
**film (quartz).

Both oligomers exhibit high energy absorption bands attributed to π-π* transitions arising from the CDT unit, and low energy absorption bands attributed to charge transfer between the CDT and PT unit. The absorption maxima ($\lambda_{max}$) of the low energy transitions for G1 and G2 occur at 618 and 626 nm in 1,2-dichlorobenzene at 25° C., respectively. Heating solutions of G1 or G2 in 1,2-dichlorobenzene to 110° C. has little effect on the resulting absorption spectra. Transitioning from solution to film, $\lambda_{max}$ of G1 is red shifted 28 nm while that of G2 remains unchanged. Comparing the changes in absorption onset from solution to film, the spectra of G1 and G2 are red-shifted 26 and 28 nm, respectively, suggesting similar packing effects in both oligomers. The optical bandgap of G1 and G2 were estimated to be 1.57 and 1.61 eV, respectively. The higher bandgap for G2 is likely a result of the thiophene spacers in-between the CDT and PT units destabilizing the LUMO and thus increasing the bandgap. Oligomer G1 has a much smaller band gap that the corresponding benzothiadiazole (BT) containing analogues (1.87-1.95 eV) (35) but is comparable to D-A-D oligomers based upon the thenopyrazine acceptor unit (1.55-1.55 eV) (35), thus confirming the high electron affinity of the PT unit.

Figure 11A:
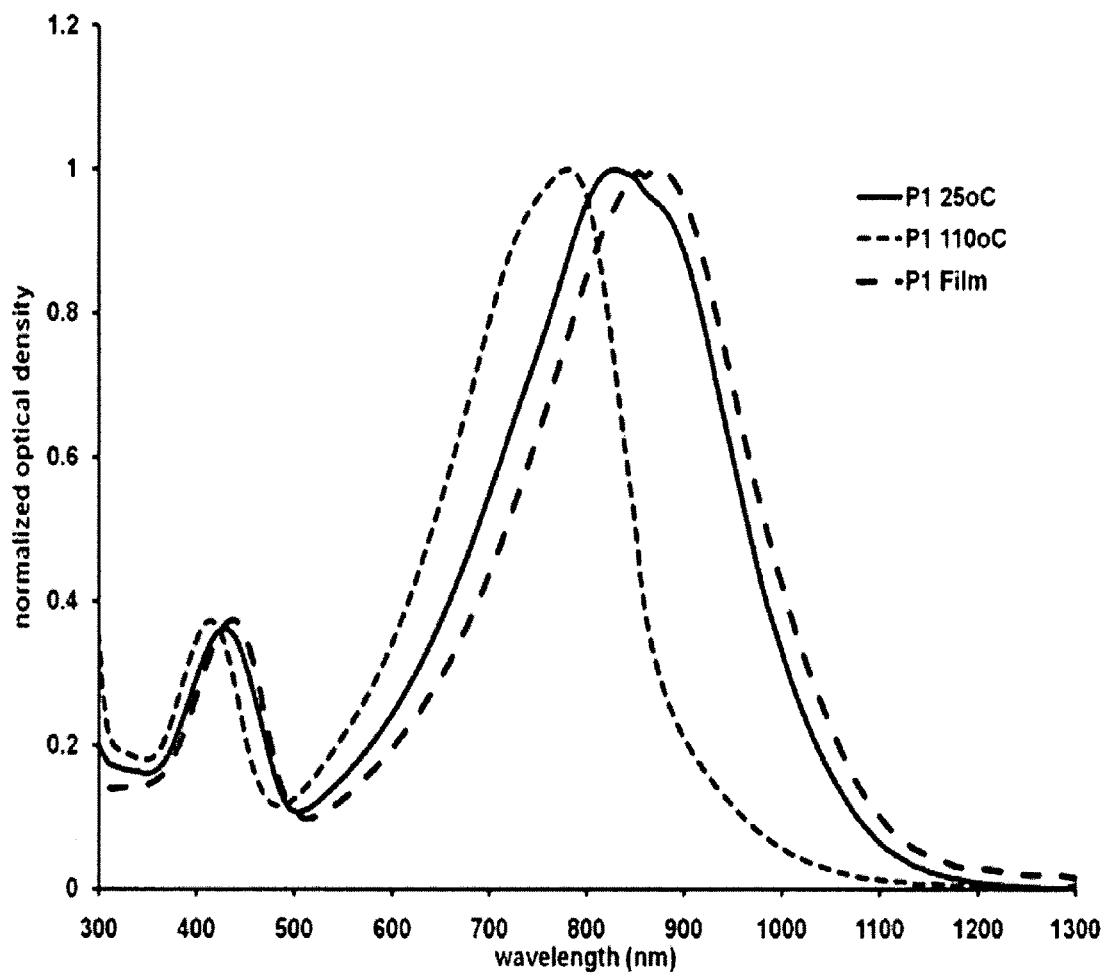
FIGS. 11A, 11B and 11C are plots of peak normalized absorption spectra for polymers P1 (11A), P2 (11B), P3 (11C). Solution spectra at 25° C. (solid line) and 110° C. (small dashed line) are recorded in 1,2-dichlorobenzene. Film spectra (large dashed line) are obtained at 25° C.
Figure 11B:
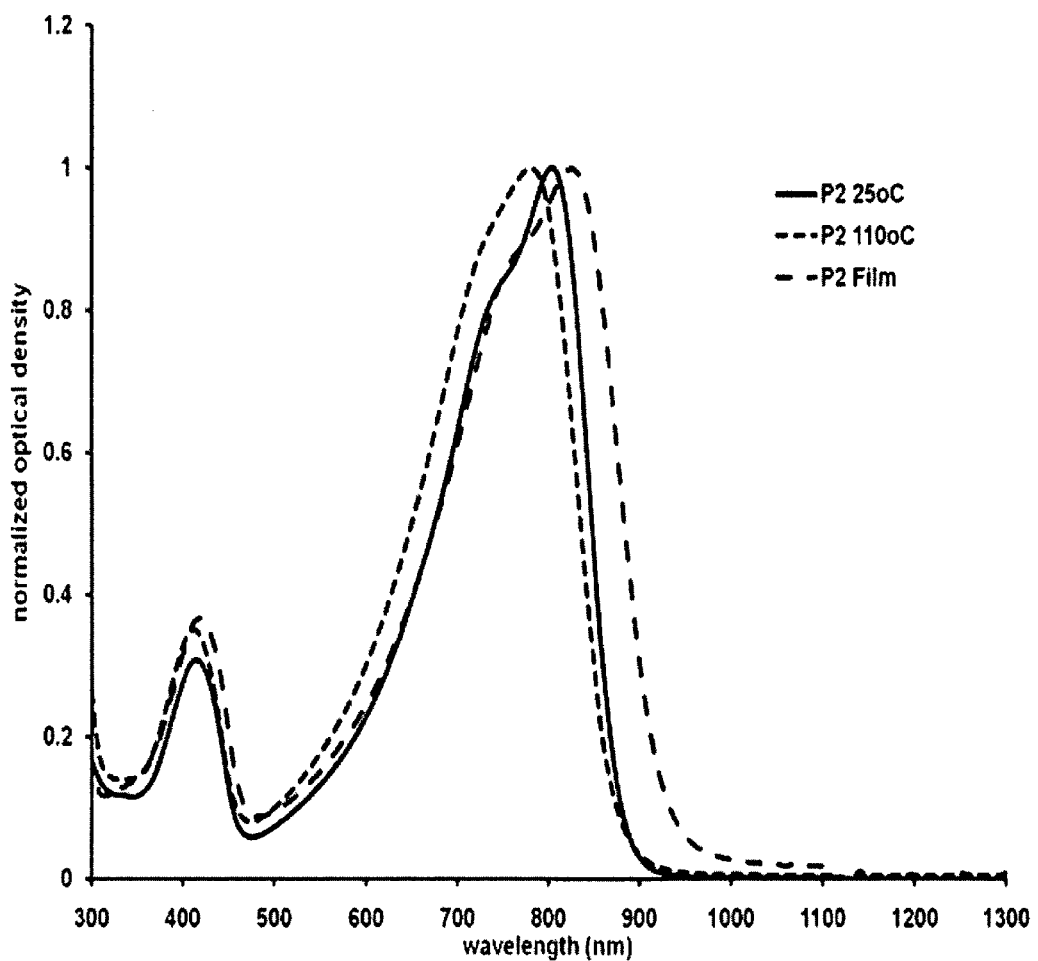
Figure 11C:
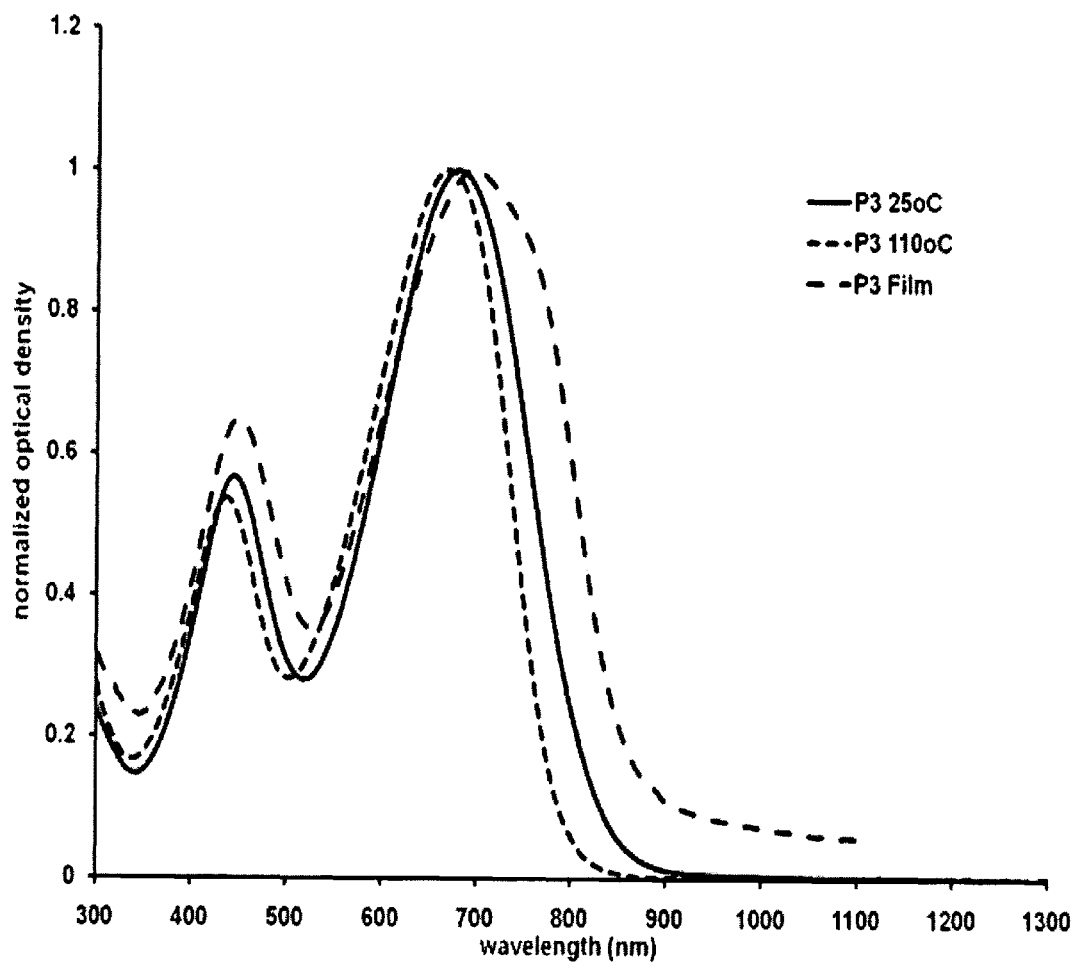

The absorption spectra of polymers P1, P2, P3 in solution at 25° C. and 110° C. and as thin films cast from chlorobenzene are shown in FIG. 11. The $\lambda_{max}$ of polymers P1, P2 and P3, in 1,2-dichlorobenzene solution at 25° C. are 830, 805, and 680, respectively. P1 absorbs light over the entire visible region and well into the NIR (NIR=wavelength of 800-2500 nm) with the onset of absorption estimated at 1100 in solution at 25° C. While P2 also exhibits a broad absorption spectrum, the estimated absorption onset in solution (890 nm) is considerably blue-shifted of P1. The observation is attributed to aggregation of the polymer chains. For P1, the linear dodecil side chains allow for tighter packing of the polymers chains, and thus greater electronic coupling between chains resulting in a narrowing of the optical bandgap. P2 incorporates bulkier 2-ethylhexyl substituents which limit the extent of polymer aggregation. Upon heating 1,2-dichlorobenzene solutions of P1 and P2 to 110° C., polymer aggregation is broken up allowing the polymer backbone structure to dominate the absorption characteristics, and thus both P1 and P2 exhibit very similar optical spectra. The absorption onset for P1 is blue-shifted approximately 260 nm upon heating while the absorption onset of P2 is only blue-shifted 5 nm, thus emphasizing the large effect linear verse branch alkyl sides chains has on polymer aggregation. Cooling to room temperature over several hours results in reformation of the aggregated species. For both P1 and P2, the transition from solution to thin film results in a slight red-shift of both $\lambda_{max}$ and $\lambda_{onset}$, again a result of greater inter-chain polymer interaction. P3 is the furthest blue-shifted polymer with an estimated absorption onset of 855 nm in 1,2-dichlorobenzene solution at 25° C. P3 incorporates 2-ethylhexyl side chains and thus only weak aggregates in solution. Closer stacking of the polymer chains is observed in thin film of P3 where the absorption onset is red-sifted by 20 nm from solution, and an aggregate peak emerges at approximately 800 nm. Additionally the absorption band at approximately 450 nm has a higher optical density that those observed in P1 and P2. This is likely a result of greater p-p* interactions resulting from the inclusion of two additional thiophene rings. The optical bandgaps of P1, P2, and P3 were estimated to be 1.10, 1.31, and 1.42, respectively.

Electrochemical Redox Properties

Figure 25A:
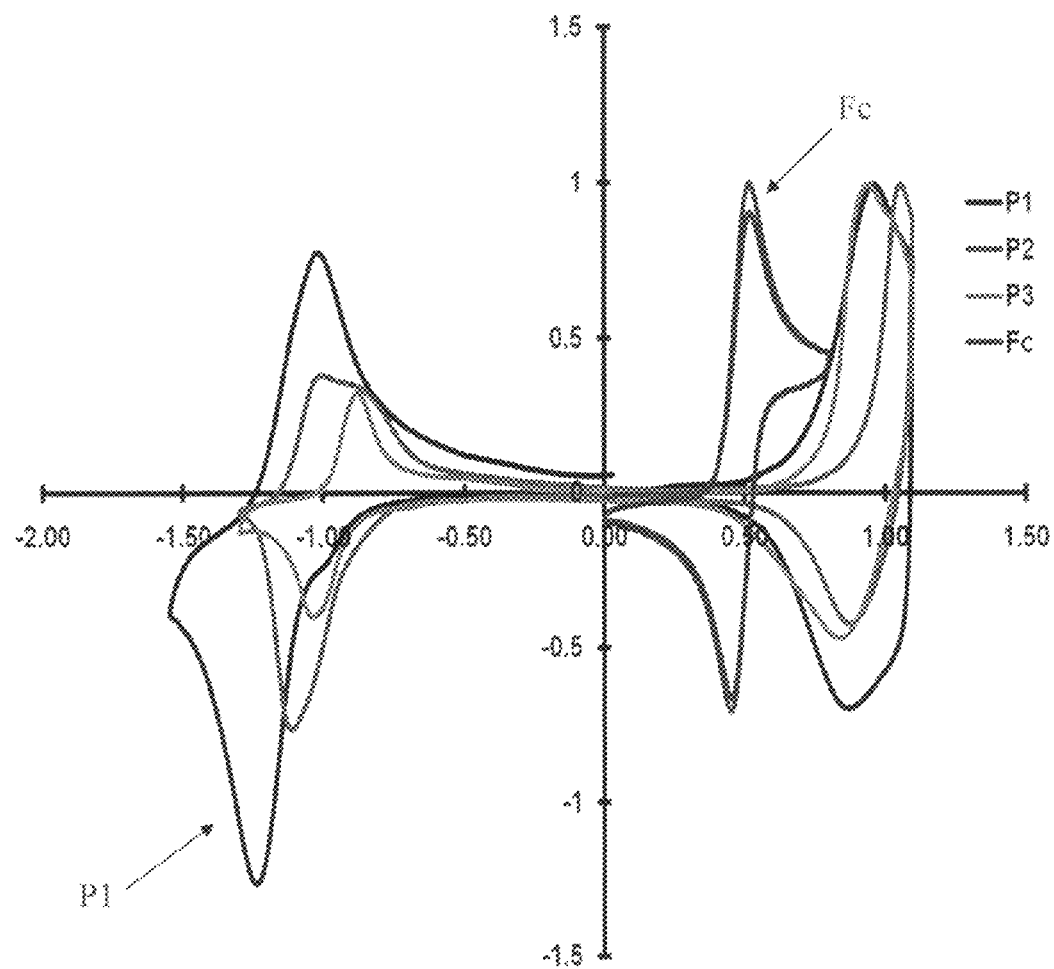
FIGS. 25A, 25B and 25C are cyclic voltamagrams for polymers P1, P2, and P3.
Figure 25B:
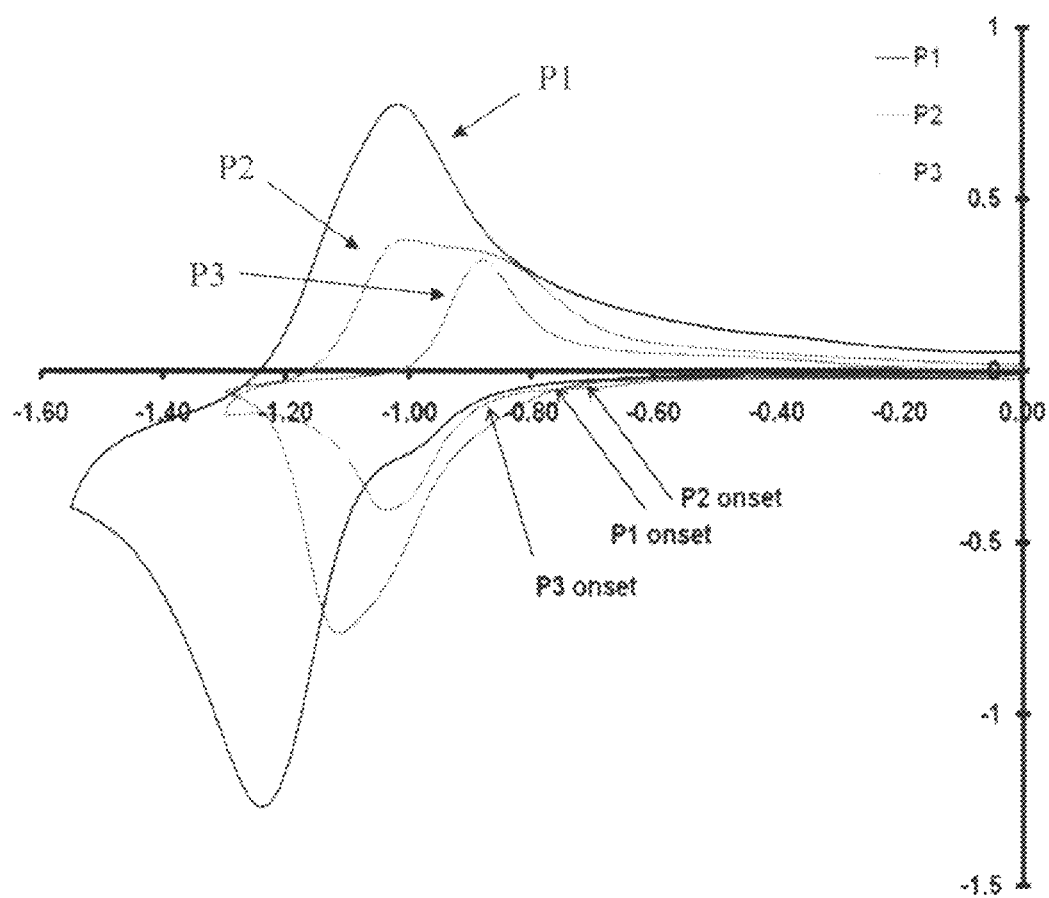
Figure 25C:
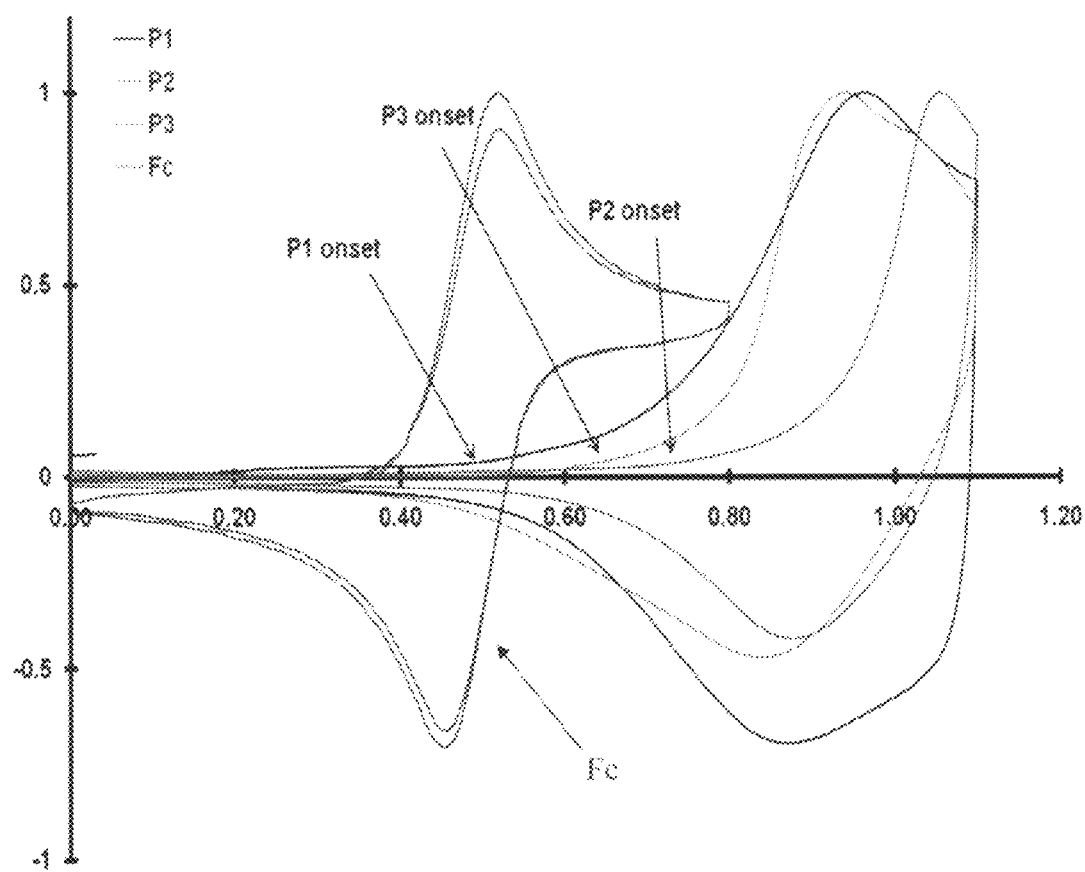
Figure 26:
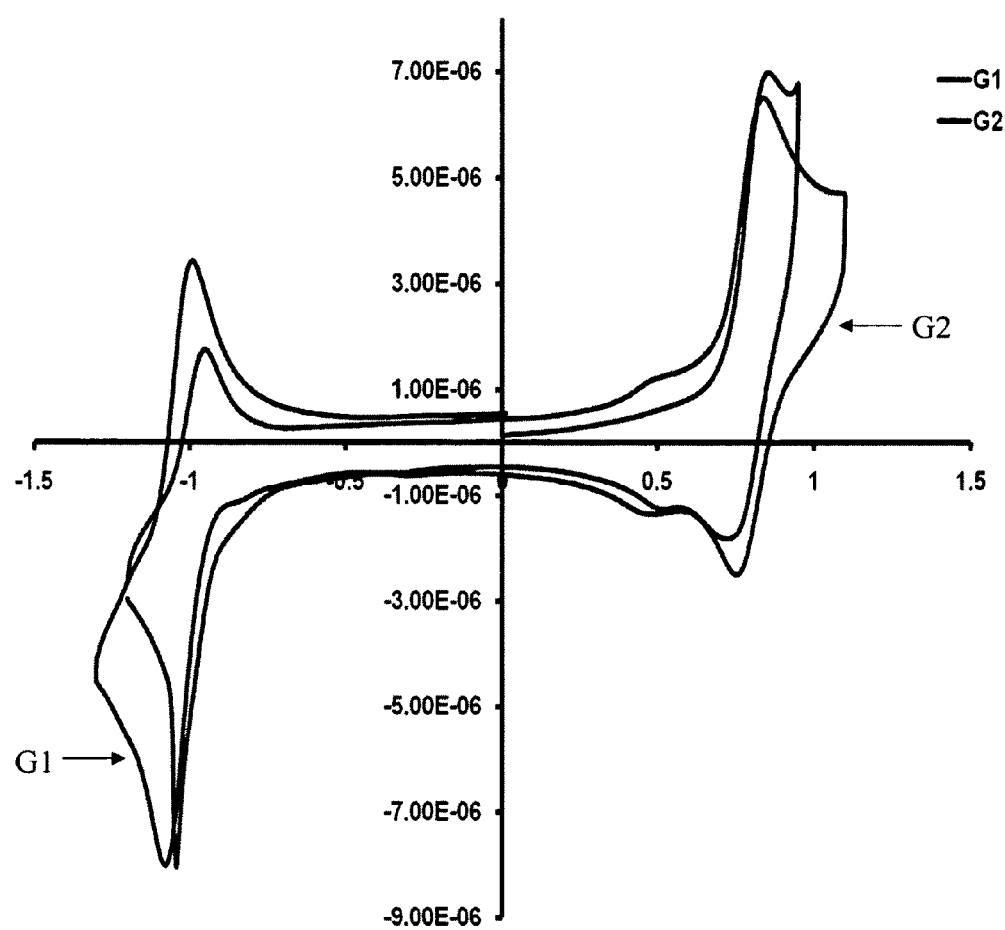
FIG. 26 is a plot of cyclic voltamagrams for oligomers G1 and G2.

The redox properties of the oligomers and polymers were investigated by cyclic voltammetry (CV) in solution and as thin films, respectively (FIGS. 25 and 26). All materials exhibit reversible reduction and oxidation process. The HOMO and LUMO energy levels were estimated using the onset of oxidation and reduction, respectively, while the electrochemical band gap $E_g$ was taken as the difference between the frontier orbital energy levels (Table 3).

TABLE 3

Cyclic voltammetry

| Materials | $E_{onset}^a$ (V) | $E_{1/2}^b$ (V) | HOMO (eV) | $E_{onset}^c$ (V) | $E_{1/2}^d$ (V) | LUMO (eV) | $E_g^e$ (eV) |
|---|---|---|---|---|---|---|---|
| P1 | 0.48 | 0.90 | −4.80 | −0.78 | −1.10 | −3.54 | 1.26 |
| P2 | 0.72 | 0.94 | −5.04 | −0.70 | −1.06 | −3.62 | 1.42 |
| P3 | 0.62 | 0.86 | −4.94 | −0.86 | −0.96 | −3.46 | 1.48 |
| G1 | 0.66 | 0.75 | −4.98 | −0.86 | −1.03 | −3.46 | 1.52 |
| G2 | 0.67 | 0.74 | −4.99 | −0.78 | −0.98 | −3.54 | 1.45 |

$^a$The oxidation onset potential of material;
$^b$the oxidation redox potential $E_{1/2} = (E_{pa} + E_{pc})/2$;
$^c$the reduction onset potential of material;
$^d$the reduction redox potential $E_{1/2} = (E_{pa} + E_{pc})/2$;
$^e$the band gap was calculated using the onset of the oxidation and reduction potential;
E(HOMO) = −($E_{ox}$ + 4.32)[eV];
E(LUMO) = −($E_{red}$ + 4.32)[eV];
HOMO of $F_c^+/F_c$ taken to be 4.8 eV;
$E_{1/2}$ of $F_c^+/F_c$ determined to be 0.48 V.

G1 and G2 have HOMO levels at approximately −4.9 eV and LUMO levels at approximately −3.5 eV making them potential candidates for donor materials in organic photovoltaic devices utilizing fullerene acceptors. The HOMO of P1 was determined to be −4.8 eV, while the LUMO was determined to be −3.54 eV. For P2, the HOMO is decreased in energy by approximately 0.24 eV to −5.04 eV, while the LUMO is only slightly affected. Transitioning from linear (P1) to branched alkyl side chains (P2) reduces polymer aggregation resulting in a de-stabilization of the polymers HOMO. Compared to P2, the HOMO energy level of P3 is increased by 0.1 eV to −4.94 eV, while the LUMO energy of P3 is increased by 0.16 eV to −3.46 eV. Clearly the incorporation of electron rich thiophene units between the CDT and PT components results in a synergistic stabilization of both the frontier molecular orbitals. Compared to the optical band gaps (Table 2), the electrochemical band gaps are slightly underestimated, although the trends are the same with P1 having the smallest energy and P3 the largest, while G1 and G2 have similar band gaps.

Reactions with $B(C_6F_5)_3$: Synthesis, Optical Properties Oligomer Interactions The borane $B(C_6F_5)_3$ is a strong Lewis acid and is expected to form a donor-acceptor adduct with the PT unit via the pyridine nitrogen, increasing the electron affinity of the PT unit, and thus increase the charge transfer characteristics of the π-conjugated materials. It has been shown that the benzothiadiazole (BT) unit is capable of binding 1 equivalent of $B(C_6F_5)_3$ via the exo-nitrogen in A-D-A type chromophore. Addition of 1 molar equivalent of $B(C_6F_5)_3$ to G1 in 1,2-dichlorobenzene solution resulted in a slight color change from blue to blue-green. Analysis by UV-visible spectroscopy at 25° C. revealed a large red shift in $\lambda_{max}$ (136 nm) and $\lambda_{onset}$ (126 nm) indicating a narrowing of the optical bandgap of G1 upon Lewis acid addition (FIG. 10, and Table 3).

It is presumed that the change in the optical absorption spectrum is due to adduct formation between $B(C_6F_5)_3$ and the PT unit via the pyridine nitrogen as depicted in Scheme 3, as follows:

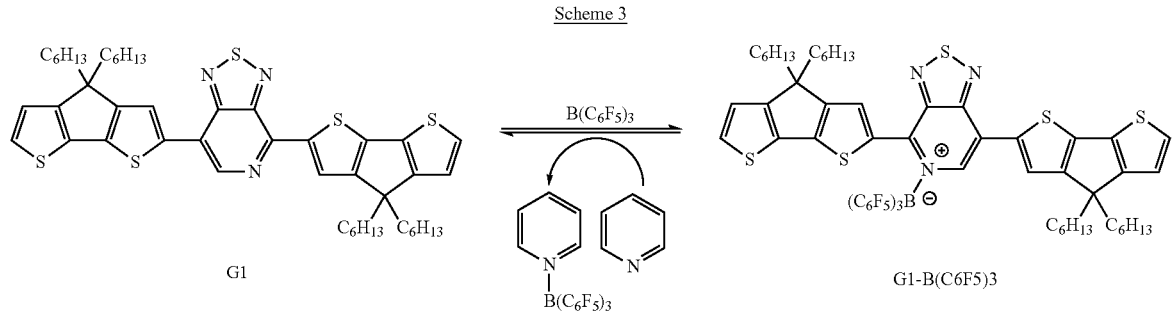

Scheme 3 where the proposed adduct formation between G1 and $B(C_6F_5)_3$ is fully reversible in the presence of a stronger base (e.g., pyridine).

Figure 12A:
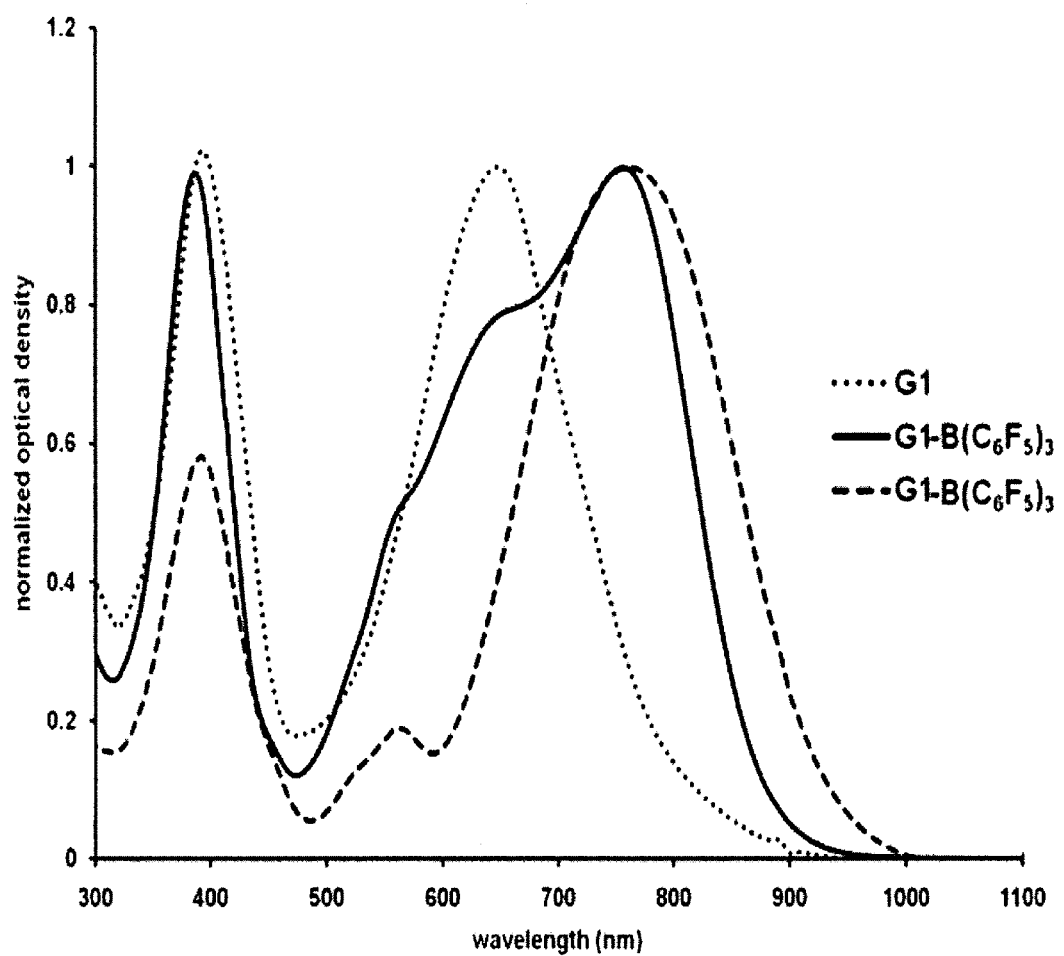
FIGS. 12A and 12B are plots of absorption spectra for G1 as a thin film (dotted line), and G1+1 molar eq. $B(C_6F_5)_3$ in 1,2-dichlorobenzene solution (solid) and as a thin film (dashed) (FIG. 12A); and G2 film (dotted line), and G2+1 molar eq. $B(C_6F_5)_3$ in 1,2-dichlorobenzene solution (solid) and as a thin film (dashed) (FIG. 12B).

Referring to FIG. 12A, the solution absorption spectrum of G1+$B(C_6F_5)_3$ exhibits a shoulder at approximately 615 nm, due to the presence of free G1 in solution. This observation implies that equilibrium exits between free and coordinated oligomer at 25° C. Transitioning from solution to the solid state, equilibrium is driven towards products, and thus an absorption spectrum attributed to G1-$B(C_6F_5)_3$ adduct is only observed. The onset of film absorption (950 nm) extends into the NIR and thus the G1-$B(C_6F_5)_3$ adduct can be considered a narrow bandgap ($E_g$=1.31 eV) material. The process of red-shifting the optical absorption spectrum of G1 with $B(C_6F_5)_3$ is fully reversible. Upon addition of the stronger Lewis base pyridine, the borane is quenched, regenerating oligomer G1 and the pyridine-$B(C_6F_5)_3$ adduct. Separation was achieved by flash column chromatography with hexanes.

Figure 12B:
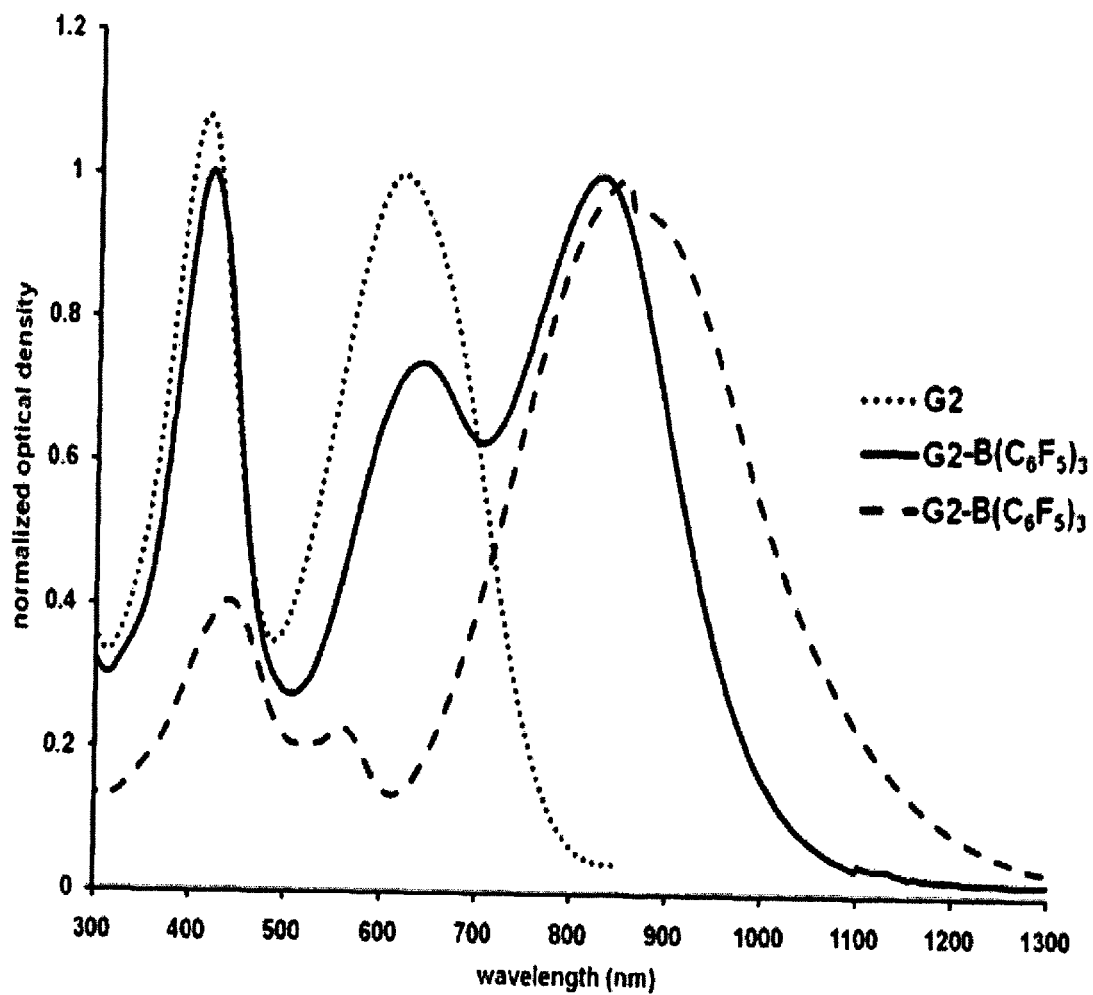

In an analogous fashion to G1, the oligomer G2 was subjected to the addition of 1 molar equivalent of $B(C_6F_5)_3$. The resulting solution and film absorption spectra are shown in FIG. 12B. A substantial red shift of 194 nm and 280 nm for $\lambda_{max}$ and $\lambda_{onset}$, respectively, was observed in solution. Again, in solution, equilibrium exists between free and bound borane and upon transitioning to the solid state, only the adduct between G2 and $B(C_6F_5)_3$ is observed. The optical bandgap of the adduct G2-$B(C_6F_5)_3$ was determined to be 1.08 eV.

Figure 23:
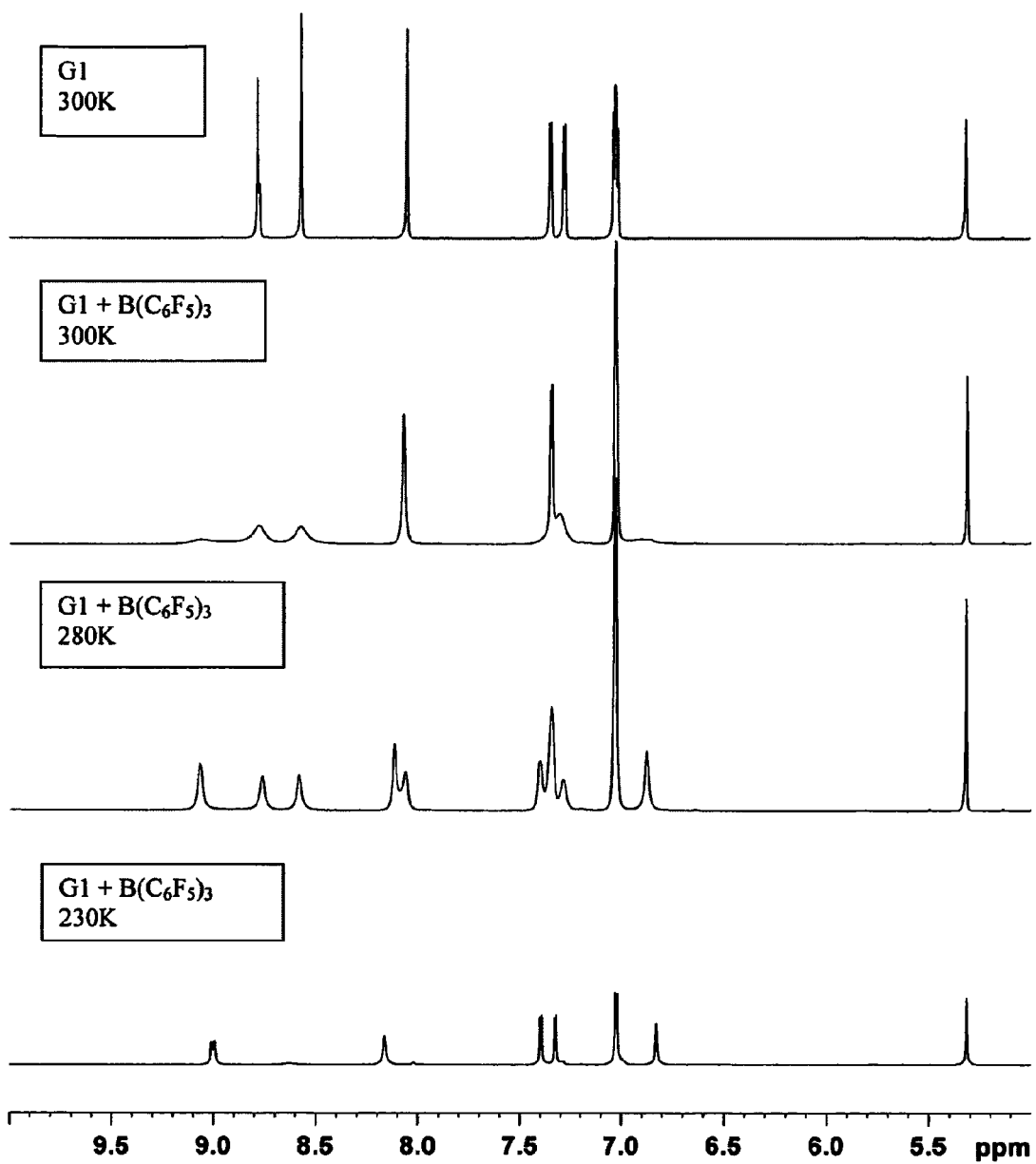
FIG. 23 is a panel of spectra showing the aromatic region of the $^1H$ NMR spectra of G1 at 300K (top), G1+$B(C_6F_5)_3$ at 300K (middle top), G1+$B(C_6F_5)_3$ at 280K (middle bottom), and G1+$B(C_6F_5)_3$ at 230K (bottom). All spectra are recorded in $CD_2Cl_2$ (5.32 ppm). Upon addition of $B(C_6F_5)_3$, the aromatic resonances of G1 are broadened due to rapid exchange of bound and unbound Lewis acid. Upon cooling to 280K, resonances for G1 and G1-$(B(C_6F_5)_3$ are observed. Further cooling to 230K drives the equilibrium fully towards adduct formation and only resonances for G1-$(B(C_6F_5)_3$ are observed.
Figure 24:
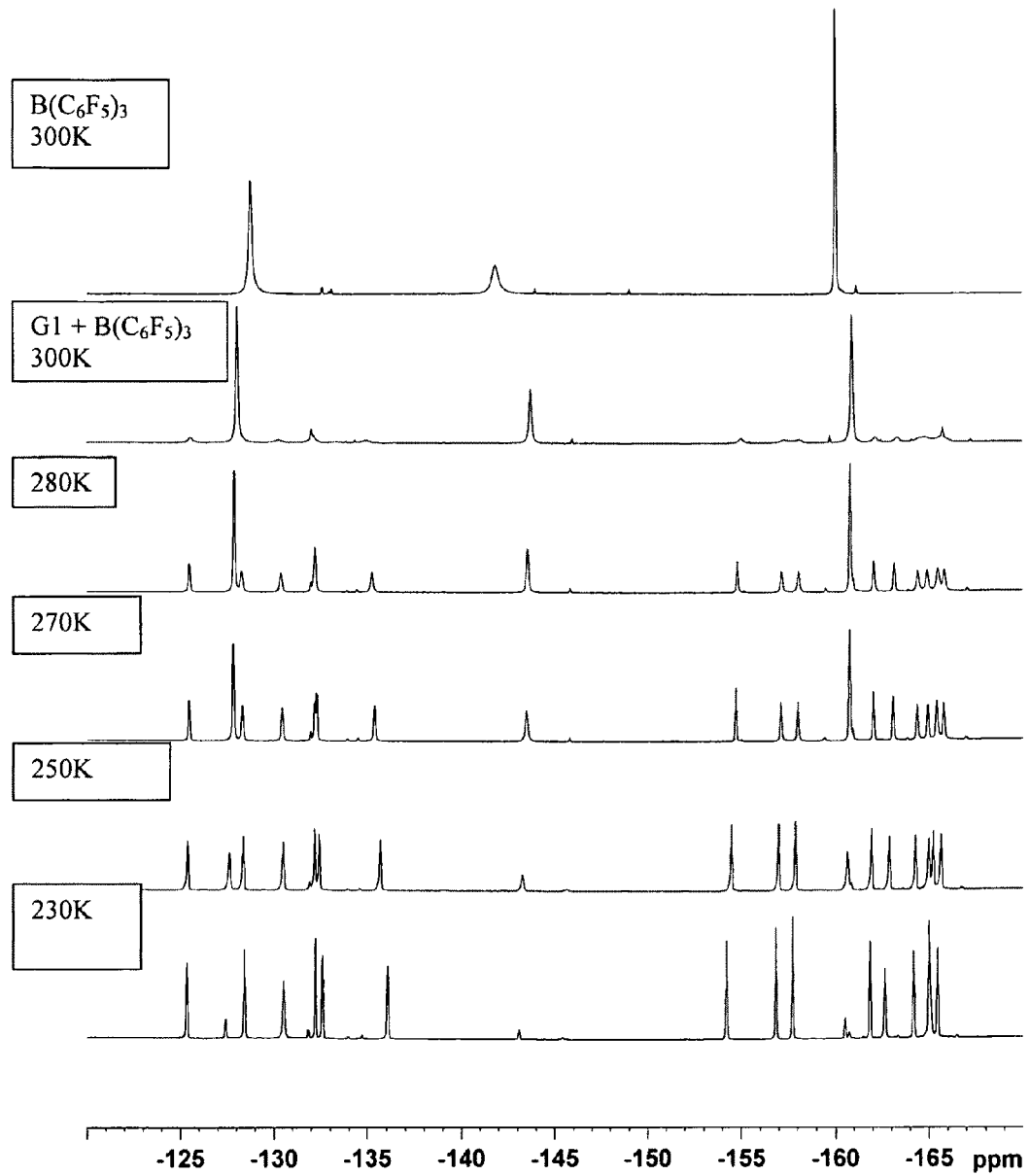
FIG. 24 is a panel of spectra showing stacked plots. The top plot shows the $^{19}F$ NMR spectrum of the Lewis acid $B(C_6F_5)_3$ in $CD_2Cl_2$ at 300K. The $2^{nd}$ to $5^{th}$ spectra (from the top) of the stacked plot show the variable temperature $^{19}F$ NMR spectra of G1 plus one equivalent of the Lewis acid $B(C_6F_5)_3$. All spectra recorded in $CD_2Cl_2$. Upon cooling the reaction mixture from 300K to 230K, adduct formation is observed as indicated by the disappearance of the resonances for free $B(C_6F_5)_3$ and the appearance of fifteen in-equivalent fluorine resonances for four coordinate borane with restricted motion.

The nature of adduct formation between oligomers G1, G2, and the Lewis acid $B(C_6F_5)_3$ was investigated by multinuclear NMR spectroscopy (FIG. 23). The $^1$H NMR spectrum of a equal molar $CH_2Cl_2$ solution of G1 and $B(C_6F_5)_3$ revealed significant broadening of the aromatic proton resonances at 300K. This observation indicates that equilibrium exists between free and Lewis acid bound G1. Upon cooling to 280K the aromatic resonances sharpen, revealing resonances attributed to both G1 and the Lewis adduct G1-B$(C_6F_5)_3$. Further cooling to 230K shifts the equilibrium toward adduct formation and thus only signals attributed to G1-$B(C_6F_5)_3$ are observed. The equilibrium constant at 280K was determined to be 0.15. Referring to FIG. 24, the $^{19}$F NMR spectrum at 300K shows 3 major resonances at −128.2, −143.8, and −160.9, for the ortho, meta, and para resonances of free $B(C_6F_5)_3$, respectively, consistent with an equilibrium mixture that favors uncomplexed materials. Upon cooling to 230K, the three ortho, meta, and para resonances of free $B(C_6F_5)_3$ disappear, and 15 new resonances from −125 to −166 ppm are observed which are attributed to 15 in-equivalent fluorine atoms of $B(C_6F_5)_3$. This observation is indicative of Lewis adduct formation between G1 and $B(C_6F_5)_3$. Steric interaction between the $C_6F_5$ rings and either the hexyl alkyl chains or the thiophene rings restricts rotation about the B—N and B—C bonds, thus rendering all 15 fluorine atoms in-equivalent. Again, addition of an equal molar amount of pyridine to this solution results in regeneration of G1 and the pyridine-$B(C_6F_5)_3$ adduct. A similar equilibrium was observed by $^1$H and $^{19}$F NMR spectroscopy for an equal molar $CH_2Cl_2$ solution of G2 and $B(C_6F_5)_3$. Here, the equilibrium constant at 280K was determined to be 0.44. The stronger affinity for G2 to bind $B(C_6F_5)_3$ is likely attributed to less steric interaction between $B(C_6F_5)_3$ and the hexyl side chains on the cyclopentadithiophene units of G2, due to the thiophene spacers.

Figure 28:
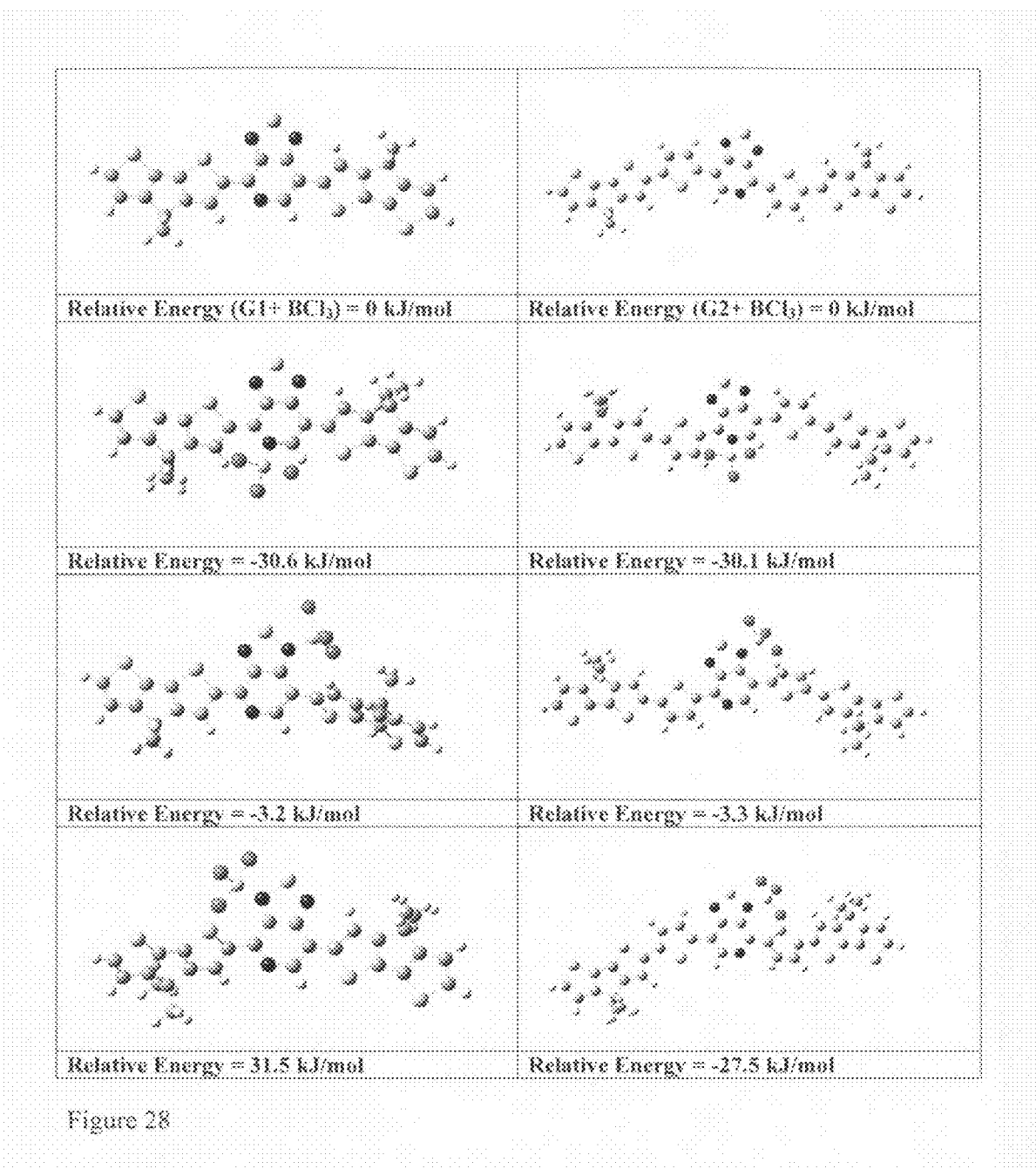
FIG. 28 is a panel of ground state geometry optimizations of G1 (left) and G2 (right) and their corresponding adduct with $BCl_3$. Methyl groups are used in place of hexylside chains on carbon, while chlorine atoms are used in place of $C_6F_5$ aryl rings on boron. Optimized structures are calculated using DFT at the B3LYP/6-31G(d,p) level of theory.
Figure 29:
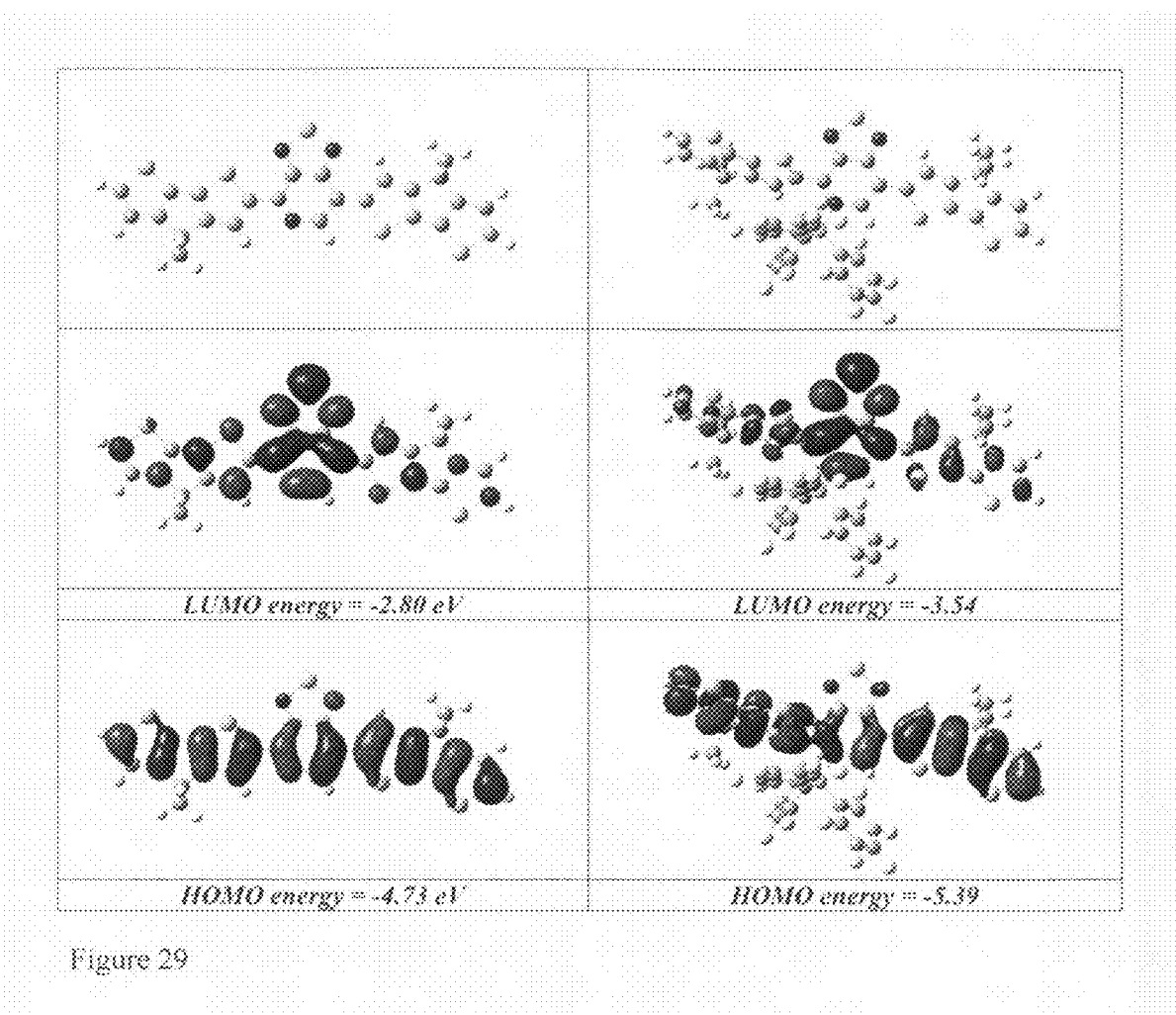
FIG. 29 is a panel of ground state geometry optimizations of G1 (left) and G1-$B(C_6F_5)_3$ (right). Methyl groups are used in place of hexylside chains on carbon. Optimized structures are calculated using DFT at the B3LYP/6-31G(d,p) level of theory.
Figure 30:
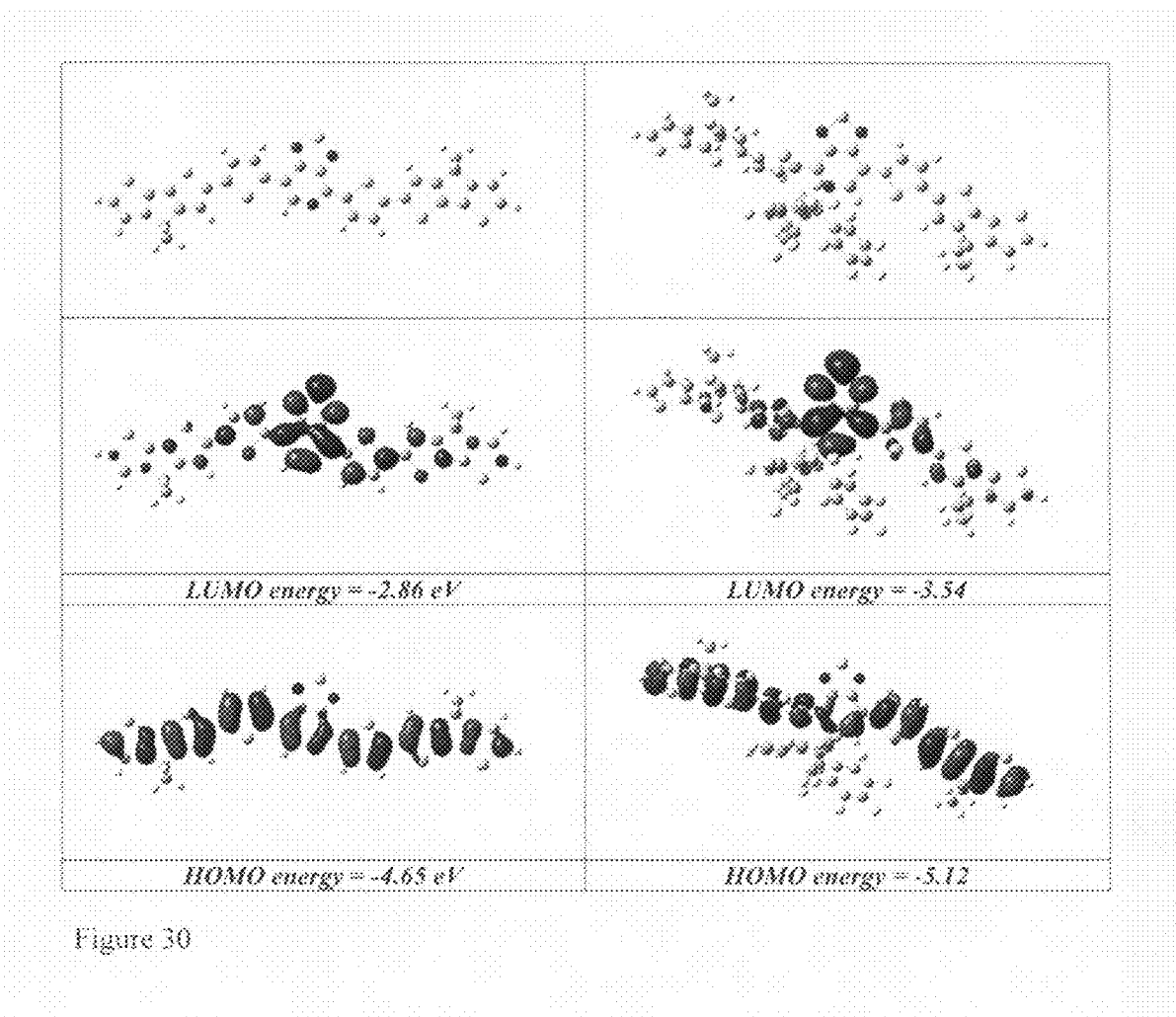
FIG. 30 is a panel of ground state geometry optimizations of G2 (left) and G2-$B(C_6F_5)_3$ (right). Methyl groups were used in replace of hexylside chains on carbon. Optimized structures are calculated using DFT at the B3LYP/6-31G(d,p) level of theory.
Figure 31:
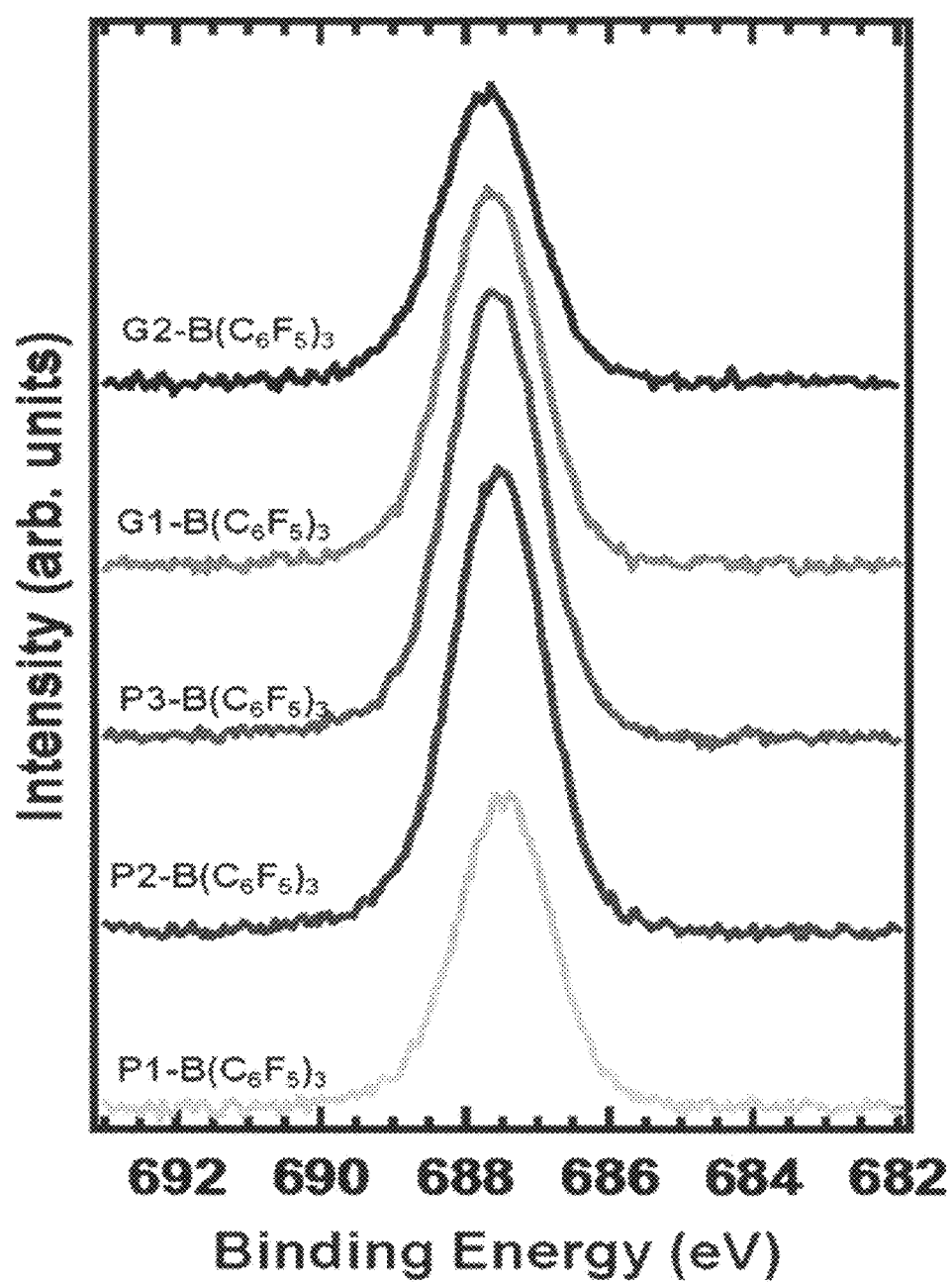
FIG. 31 is a panel of spectra showing data for fluorine (1 s) obtained from X-ray photoelectron spectroscopy (XPS).
Figure 32A:
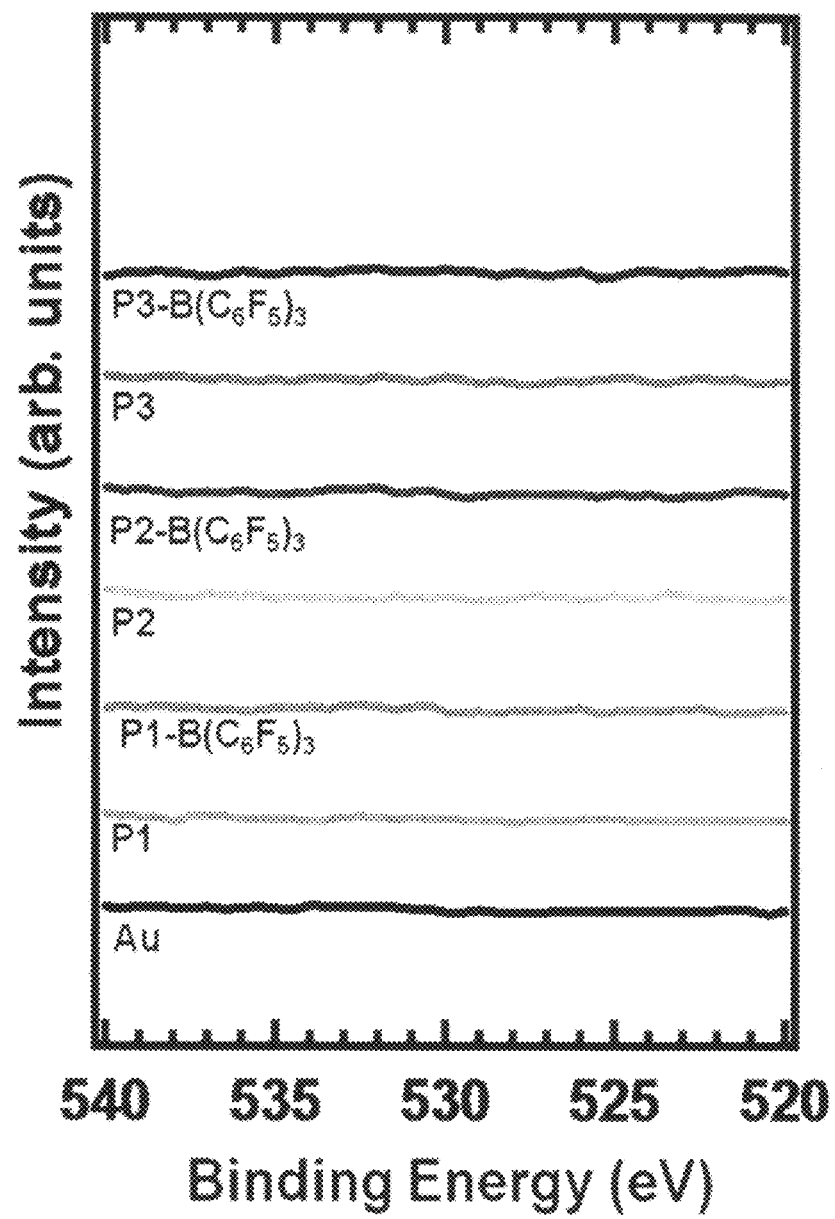
FIGS. 32A and 32B are panels of spectra showing data for oxygen (1 s) obtained from XPS for polymers (32A) and oligomers (32B) and their corresponding Lewis acid adducts.
Figure 32B:
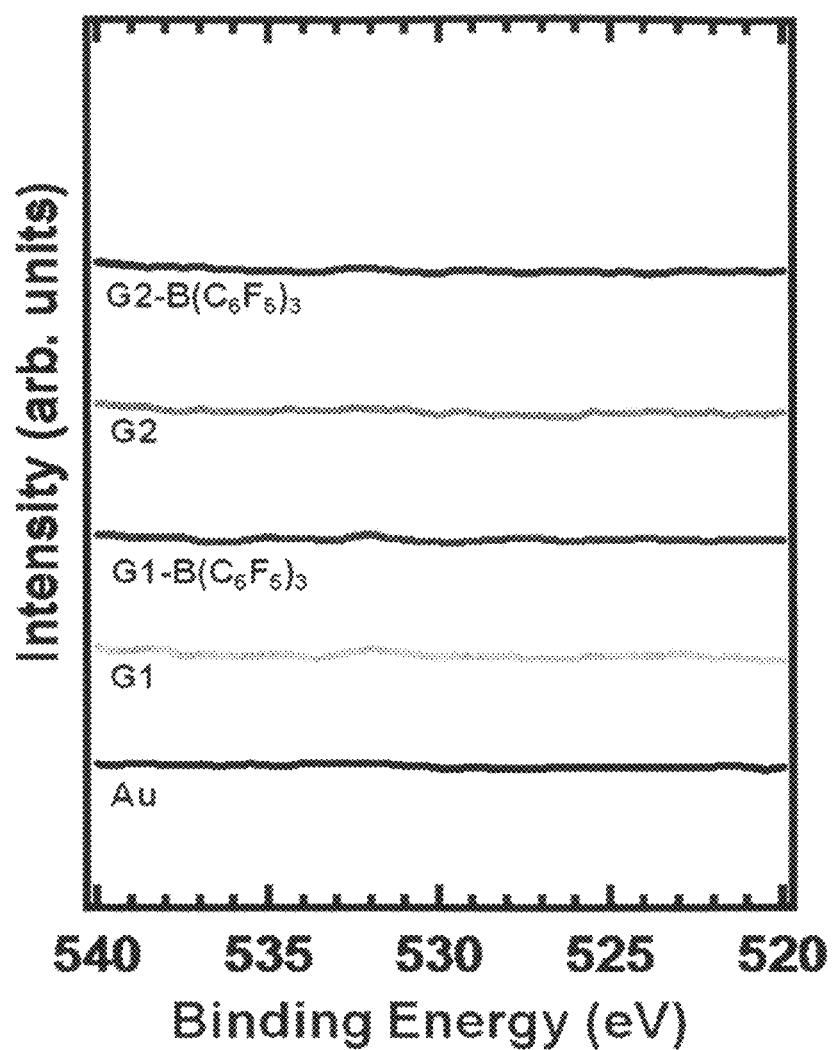

To confirm that $B(C_6F_5)_3$ binds to the pyridine nitrogen of G1 and G2, preliminary DFT calculations were performed (FIGS. 30, 31 and 32). Structures of G1 and G2 were optimized at the B3LYP/6-31G** level of theory replacing the hexyl chains with methyl groups (FIGS. 29 and 30). Using the same theory, structures of G1 and G2 with the Lewis acid $BCl_3$ bound to either imine nitrogen or the pyridine nitrogen of the PT unit were optimized (FIG. 28). BCl$_3$ was used in place of B(C$_6$F$_5$)$_3$ to save on computational resources. Energies determined from the optimized structures show that adduct formation at the pyridine nitrogen is more favorable by a minimum of 27 kJ/mol over adduct formation at an imine nitrogen.

Polymer Interactions

Figure 13A:
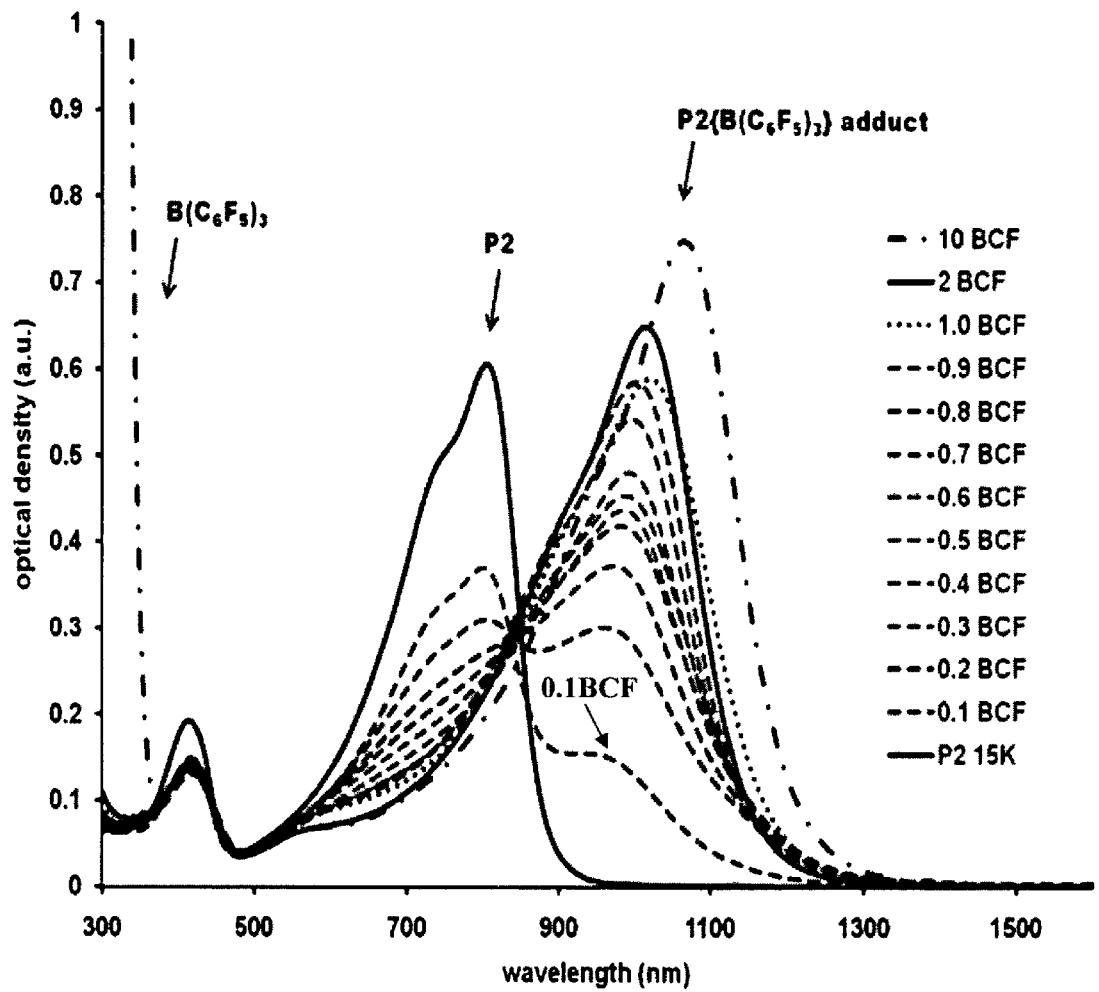
FIGS. 13A and 13B are plots of absorption spectra of P2 plus varying equivalents by weight of $B(C_6F_5)_3$ (BCF) in o-dichlorobenzene at 25° C. under an atmosphere of $N_2$ (FIG. 13A), and normalized absorption spectra of P2 as a thin film (dotted line) P2-$B(C_6F_5)_3$ in o-dichlorobenzene (solid) and P2-$B(C_6F_5)_3$ in as a thin film (dashed) (FIG. 13B).
Figure 13B:
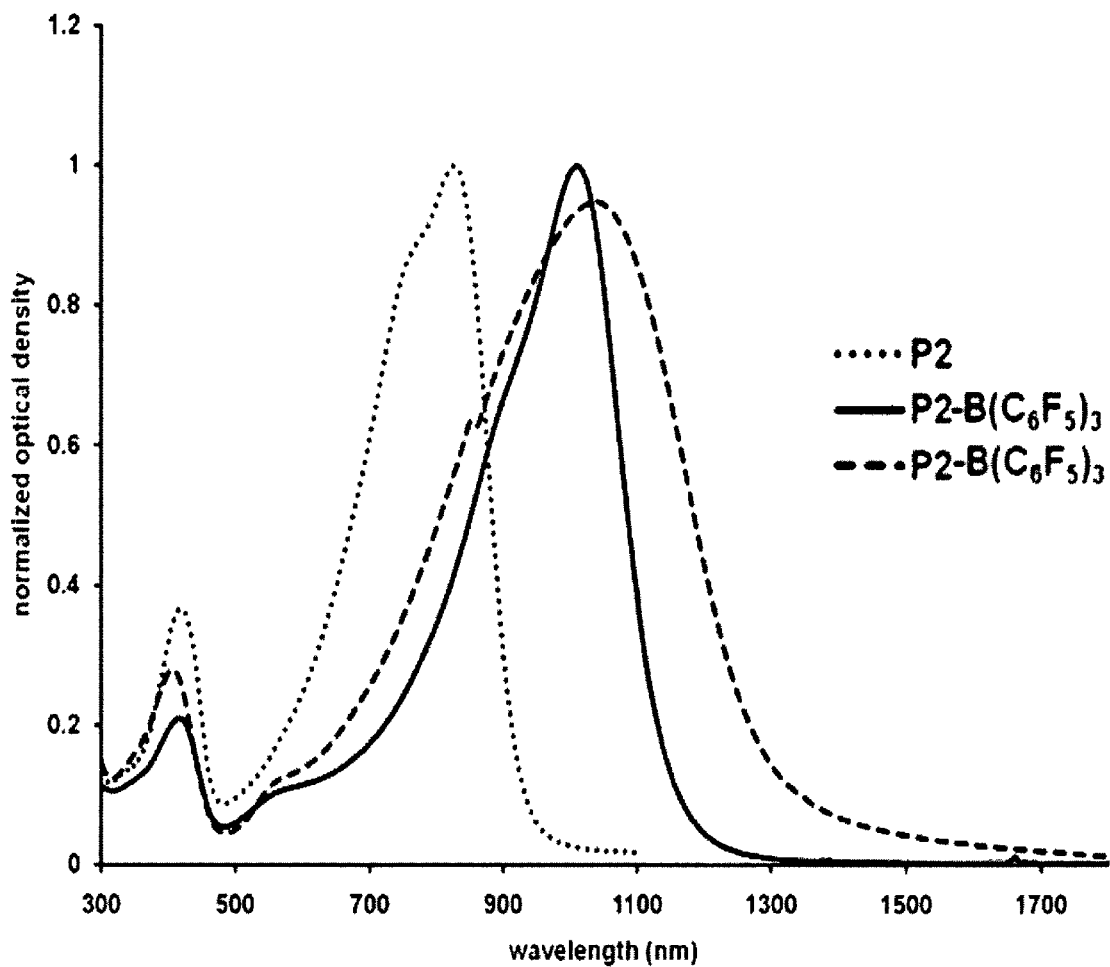

The interaction of polymers P1, P2, and P3 with the Lewis acid B(C$_6$F$_5$)$_3$ was then investigated. In o-dichlorobenzene solution, P2 was subjected to the addition of varying equivalents (by weight) of B(C$_6$F$_5$)$_3$ and the absorption spectra measured (FIG. 13). Upon addition of 0.1 equivalents by weight of B(C$_6$F$_5$)$_3$, the absorption peak at ~805 nm decreases while a new red-shifted absorption peak appears at ~980 nm. Addition of 0.4 weight equivalents of B(C$_6$F$_5$)$_3$ resulted in almost complete disappearance of the absorption band for P2, and an increase in the strength of the absorption peak at ~980 nm. Based upon the Lewis adduct formation observed with G1 and G2, the new absorption band in the NIR region of the absorption spectrum is attributed to the Lewis adduct between P2 and B(C$_6$F$_5$)$_3$, where the borane forms a dative interaction with the pyridine nitrogen of the PT acceptor unit. Further addition of B(C$_6$F$_5$)$_3$, up to 10 equivalents by weight results in a progressive red shift of $\lambda_{max}$ (980 to 1000 nm) while the onset of absorption remains constant. This observation can be attributed to an equilibrium existing between free and Lewis acid bound P2. Increasing the concentration of B(C$_6$F$_5$)$_3$ in solution shifts the equilibrium in favor of adduct formation Transitioning from solution to thin film, a red shift of 52 nm and 128 nm was observed for $\lambda_{max}$ and $\lambda_{onset}$ (FIG. 13, Table 4), a likely result of closer inter-polymer chain interactions and stronger B—N adduct formation.

TABLE 4

Optical data for B(C$_6$F$_5$)$_3$

| Compound* | $\lambda_{max}$ (nm)* | $\lambda_{onset}$ (nm)* | $\lambda_{max}$ (nm)** | $\lambda_{onset}$ (nm)** | Bandgap [eV] |
|---|---|---|---|---|---|
| G1-B(C$_6$F$_5$)$_3$ | 752 562, 640, 384 | 892 | 764 558, 386 | 950 | 1.31 |
| G2-B(C$_6$F$_5$)$_3$ | 820 632, 416 | 1022 | 868 568, 444 | 1152 | 1.08 |
| P1-B(C$_6$F$_5$)$_3$ | 1030 412 | 1232 | 1080 410 | 1300 | 0.95 |
| P2-B(C$_6$F$_5$)$_3$ | 998 440 | 1162 | 1050 410 | 1290 | 0.96 |
| P3-B(C$_6$F$_5$)$_3$ | 986 450 | 1236 | 1090, 480 | 1395 | 0.89 |

*Solution (1,2-dichlorobenzene);
**film (quartz).

Figure 27A:
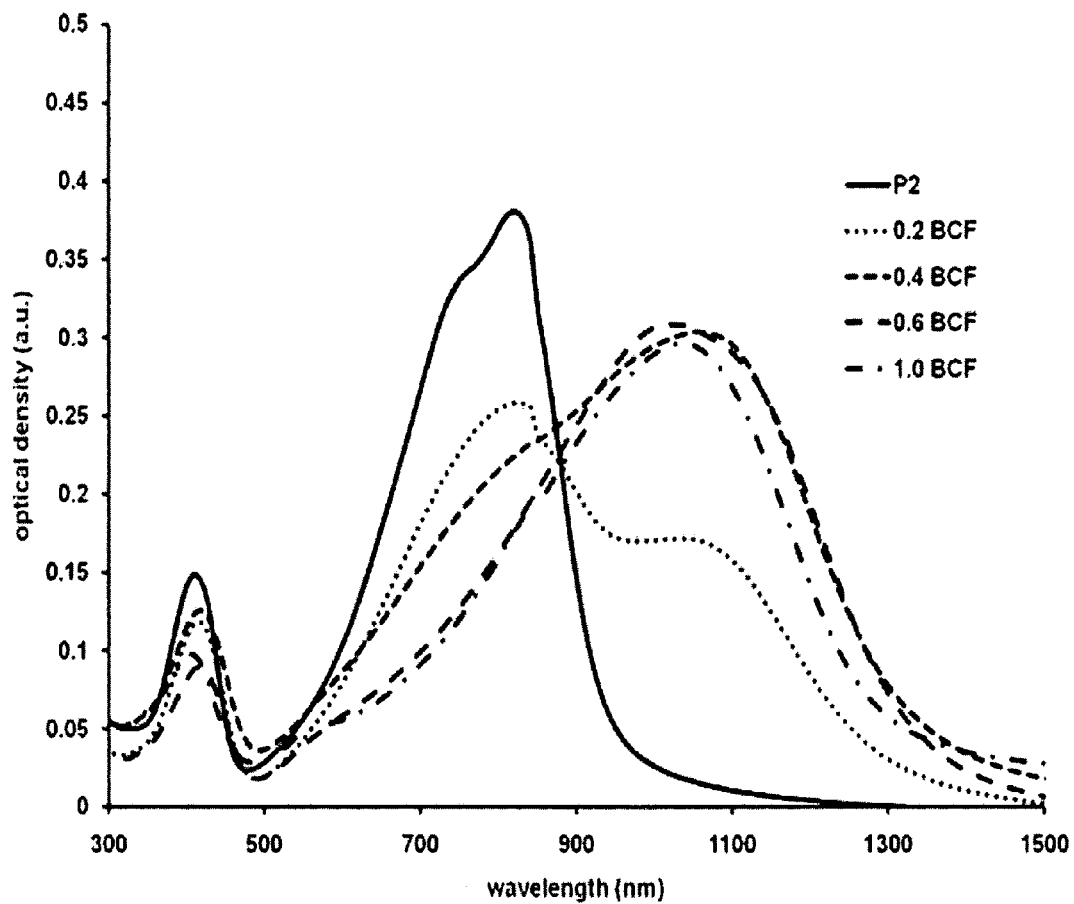
FIG. 27A is a plot of absorption spectra of P2 plus varying equivalents (0, 0.2, 0.4, 0.6, 1) by weight of $B(C_6F_5)_3$ (BCF) as thin films on quartz cast from chlorobenzene at 1500 rpm under an $N_2$ atmosphere.
Figure 27B:
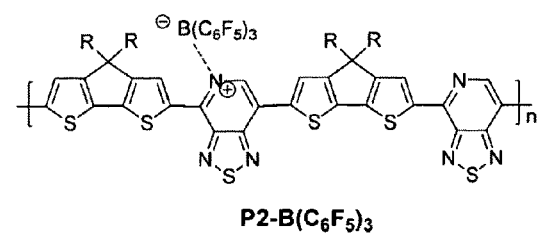
FIG. 27B is a proposed structure of adduct between P2 and $B(C_6F_5)_3$.

Remarkably, upon the addition of B(C$_6$F$_5$)$_3$ to P2, a red-shift in the thin film absorption onset of ~340 nm can be achieved. Although not wishing to be bound by any theory, the current thinking is that the upon coordination of B(C$_6$F$_5$)$_3$ to the pyridine nitrogen of the PT acceptor unit, a significant amount of electron density is removed from the π-system, increasing the electron affinity of the acceptor unit, thus narrowing the optical band gap. Based upon solution (FIG. 13) and thin film (FIG. 27A) absorption spectra of P2 plus B(C$_6$F$_5$)$_3$, it appears that upon addition of ~0.5 equivalents by weight of B(C$_6$F$_5$)$_3$ to P2, complete formation of the adduct P2-B(C$_6$F$_5$)$_3$ is achieved. The calculated molecular weight of the repeat unit of P2 is 538 g mol$^{-1}$ while that of B(C$_6$F$_5$)$_3$ is 512 g mol$^{-1}$, therefore it is assumed that every second PT unit is coordinated to one B(C$_6$F$_5$)$_3$ molecule (FIG. 27B).

Figure 14A:
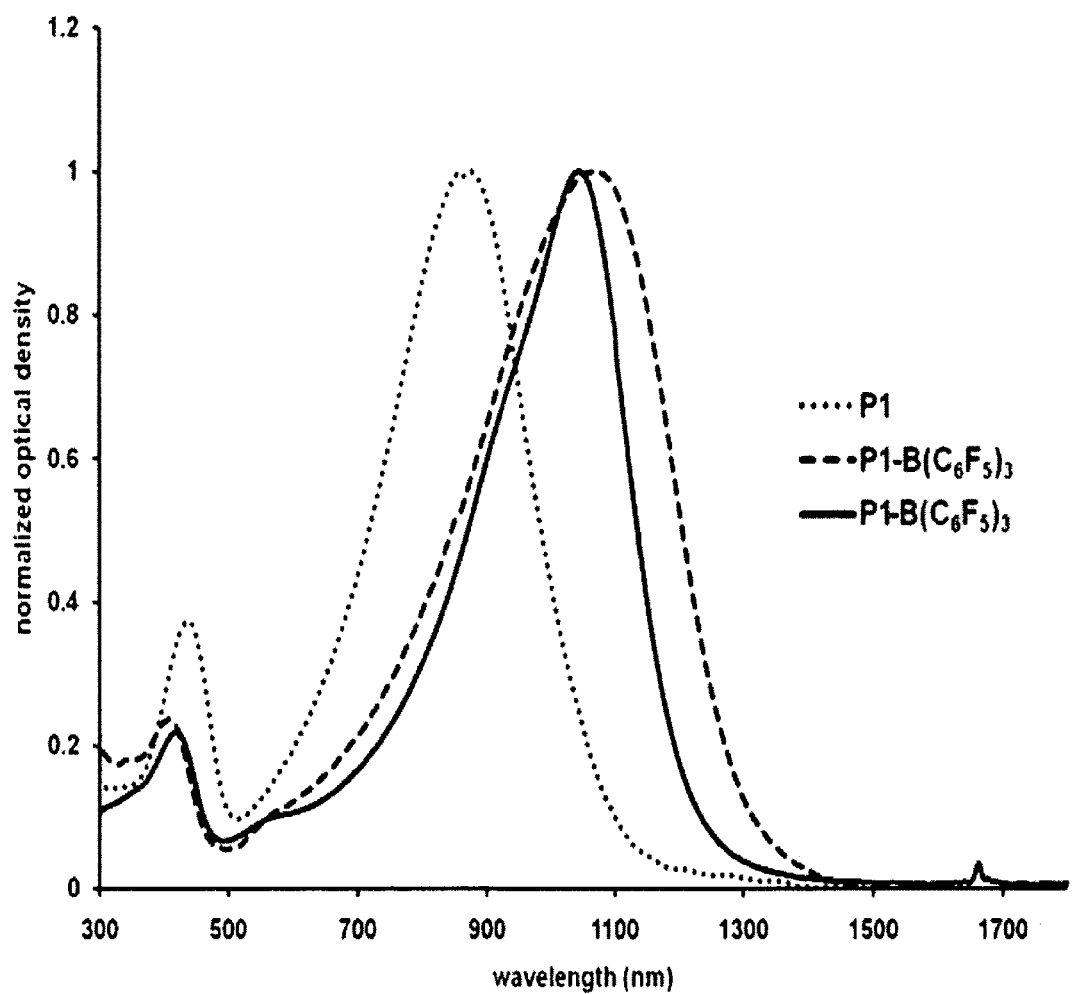
FIGS. 14A and 14B are plots of normalized absorption spectra of P1 as a thin film (dotted line), P1-$B(C_6F_5)_3$ in o-dichlorobenzene (solid), and P2-$B(C_6F_5)_3$ as a thin film (dashed) (14A), and normalized absorption spectra of P3 as a thin film (dotted line), P3-$B(C_6F_5)_3$ in o-dichlorobenzene (solid), and P3-$B(C_6F_5)_3$ as a thin film (dashed) (FIG. 14B).
Figure 14B:
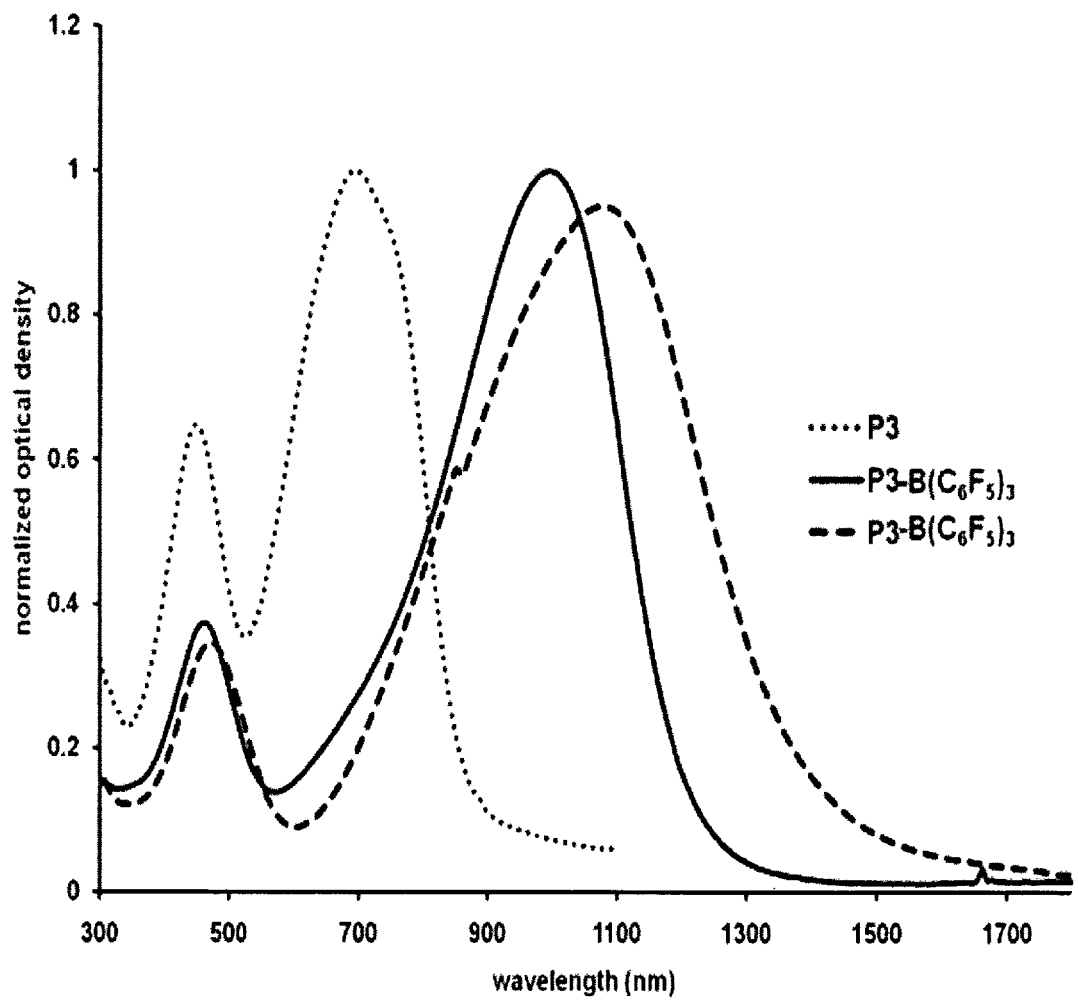

In a similar fashion to P2, the polymer-B(C$_6$F$_5$)$_3$ adducts P1-B(C$_6$F$_5$)$_3$ and P3-B(C$_6$F$_5$)$_3$ are readily obtained upon addition of Lewis acid to polymer solutions. Their absorption spectra in solution and as thin films are shown in FIG. 14, while their optical data are summarized in Table 4. Both Lewis acid adducts of P1 and P3 have significant absorption into the NIR-region with absorption onsets in the solid state of 1300 and 1395, respectively. Comparing P1-B(C$_6$F$_5$)$_3$ and P2-B(C$_6$F$_5$)$_3$, it is noted that they have very similar absorption spectra and optical band gaps, 0.95 and 0.96 eV, respectively. Considering that both of these materials have the same backbone structure and only differ in alkyl sides-chains, it is likely that coordination of B(C$_6$F$_5$)$_3$ reduces inter-chain aggregation and negates side chain effects observed in the neat polymers. The adduct P3-B(C$_6$F$_5$)$_3$ has the smallest optical band gap, which is attributed to a stronger B—N interaction as a result of reduced side chain-B(C$_6$F$_5$)$_3$ interaction due to the presence of the additional thiophene spacers. It should be mentioned that for each polymer, the addition of B(C$_6$F$_5$)$_3$ only affects the low energy charge transfer energy band, while the high energy band at ~400-450 nm remains unchanged. Addition of a stronger base (i.e., pyridine or PPh$_3$) results in B(C$_6$F$_5$)$_3$ abstraction and regeneration of the parent polymer. All of the Lewis adducts are stable indefinably in solution or as thin films under an inert atmosphere of N$_2$ or Ar. Upon expose to moisture, the materials slowly hydrolyze to give the corresponding pyridium borate salts.

Determination of HOMO Energy Level Via UPS and DFT Calculations

To gain insight into the narrowing of the optical band gap of oligomers G1, G2 and polymers P1, P2, and P3 upon interaction with B(C$_6$F$_5$)$_3$, HOMO energy levels of each material as thin films was estimated using ultraviolet photoelectron spectroscopy. In addition, for oligomers G1 and G2, preliminary DFT calculations were carried out. All data is listed in Table 5.

TABLE 5

HOMO-LUMO Energy Levels obtained via UPS/absorption onset

| Compound | HOMO (eV)* | LUMO (eV)** | $E_g$ (optical)*** | HOMO (eV) | LUMO (eV) | $E_g$ (calc) |
|---|---|---|---|---|---|---|
| G1 | −4.86 | −3.29 | 1.57 | −4.73 | −2.80 | 1.93 |
| G1-B(C$_6$F$_5$)$_3$ | −5.37 | −4.06 | 1.31 | −5.39 | −3.54 | 1.85 |
| G2 | −4.79 | −3.18 | 1.61 | −4.65 | −2.86 | 1.79 |
| G2-B(C$_6$F$_5$)$_3$ | −5.08 | −4.00 | 1.08 | −5.12 | −3.54 | 1.58 |
| P1 | −4.66 | −3.56 | 1.10 | | | |
| P1-B(C$_6$F$_5$)$_3$ | −5.22 | −4.27 | 0.95 | | | |
| P2 | −5.01 | −3.70 | 1.31 | | | |
| P2-B(C$_6$F$_5$)$_3$ | −5.24 | −4.28 | 0.96 | | | |
| P3 | −4.91 | −3.49 | 1.42 | | | |
| P3-B(C$_6$F$_5$)$_3$ | −5.23 | −4.34 | 0.89 | | | |

*Obtained from UPS measurements;
**estimated from HOMO and optical band gap;
***determined from onset of absorption.

The HOMO levels determined via UPS compare to those obtained by CV within ~0.1 eV. Interaction of the oligomers and/or polymers with B(C$_6$F$_5$)$_3$ results in a synergetic lowering of both the HOMO and LUMO energy levels, with the LUMO exhibiting the greatest change resulting in the narrowing of the band gap. These data imply that coordination of B(C$_6$F$_5$)$_3$ to the PT acceptor unit, not only removes electron density away from this unit, but also the entire π-conjugated system. Quite remarkably, for each material, the HOMO is lowered in energy by ~0.2 to 0.5 eV. This observation is intriguing as decreasing the energy of the HOMO level in light-harvesting materials is an effective way to increase the open circuit voltage in bulk-hetero junction (BHJ) organic photovoltaic devices. Comparing P1 to P2 adduct formation results in a decrease in the HOMO energy levels by 0.56 and −0.23 eV, respectively. The larger change for P1 can be attributed to the break-up of significant inter-chain interactions observed for P1 (linear side chains) verse P2 (branched side chains) by coordination of the Lewis acid. The HOMO level of P3 is lowered by −0.32 eV upon interaction with $B(C_6F_5)_3$. The larger shift compared to that of P2 is attributed to stronger Lewis adduct formation between pyridine N and B. Comparing G1 to G2, adduct formation results in a decrease in the HOMO energy levels by 0.51 and 0.29 eV, respectively. These changes in absolute energies are confirmed by DFT calculations at the B3LYP/6-31G(d,p) level of theory.

The experimental setup for UPS requires that the thin film samples be subject to high vacuum for 12 hours. Because free $B(C_6F_5)_3$ readily sublimes under vacuum, XPS measurements were performed to confirm that the Lewis acid remained in the sample. As seen in FIG. 31, signals attributed to fluorine atoms were observed confirming the presence of $B(C_6F_5)_3$. Additionally, as mentioned above, the adducts between the oligomers/polymers and $B(C_6F_5)_3$ are prone to hydrolysis, therefore the thin films were examined for the presence of oxygen. As detailed in FIG. 32, no signal for oxygen was detected.

SCLC Device Performance

The parent oligomers and polymers are fully π-conjugated materials with the ability to act as semi-conductors and transport charge. The impact of Lewis acid coordination on the hole transport properties of G1, G2, P1, P2, and P3 were examined using the space charge limited model. Devices were fabricated by spinning coating an appropriate oligomer or polymer solution onto a PEDOT:PSS coated ITO substrate followed by evaporation of aluminium. The hole transport mobility of G1 and G2 was determined to be $3(2)\times10^{-5}$ and $4(3)\times10^{-5}$ cm$^2$/Vs, respectively (Table 6).

TABLE 6

Charge (Hole) Mobility

| Compound | Hole mobility (cm$^2$/Vs) | Compound | Hole mobility (cm$^2$/Vs) |
|---|---|---|---|
| G1 | $3 \pm 2 \times 10^{-5}$ | P1 | $4 \pm 2 \times 10^{-6}$ |
| G1-B(C$_6$F$_5$)$_3$ | $1 \pm 1 \times 10^{-5}$ | P1-B(C$_6$F$_5$)$_3$ | $8 \pm 3 \times 10^{-6}$ |
| G2 | $4 \pm 3 \times 10^{-5}$ | P2 | $4 \pm 1 \times 10^{-5}$ |
| G2-B(C$_6$F$_5$)$_3$ | $5 \pm 3 \times 10^{-5}$ | P2-B(C$_6$F$_5$)$_3$ | $2 \pm 0.3 \times 10^{-4}$ |
| | | P3 | $1 \pm 0.7 \times 10^{-5}$ |
| | | P3-B(C$_6$F$_5$)$_3$ | $7 \pm 0.6 \times 10^{-5}$ |

Addition of $B(C_6F_5)_3$ resulted in minimal impact on the ability of the oligomers to transport holes, with G1-$B(C_6F_5)_3$ and G2-$B(C_6F_5)_3$ having a mobility of $1(1)\times10^{-5}$ and $5(3)\times10^{-5}$ cm$^2$/Vs, respectively. Polymers P1, P2, and P3 exhibit hole transport mobility of $4(2)\times10^{-6}$, $4(1)\times10^{-5}$ cm$^2$/Vs and $1(1)\times10^{-5}$ cm$^2$/Vs, respectively. The lower mobility compared to related 2,1,3-benzothiadiazole (BT) derivatives can be attributed to the regio-random nature of the polymers which likely results in reduced long-range order necessary for efficient charge transport. Upon interaction with $B(C_6F_5)_3$, the hole transport properties of P1 and P3 remain largely un-affected. Interestingly, the mobility of P2-$B(C_6F_5)_3$ is an order of magnitude larger than for P2. It is assumed that upon addition of $B(C_6F_5)_3$, there is a slight increase in intermolecular ordering of the polymer chains, possibly due to $C_6F_5$-arene interactions and/or dipole-dipole interactions.

Figure 15:
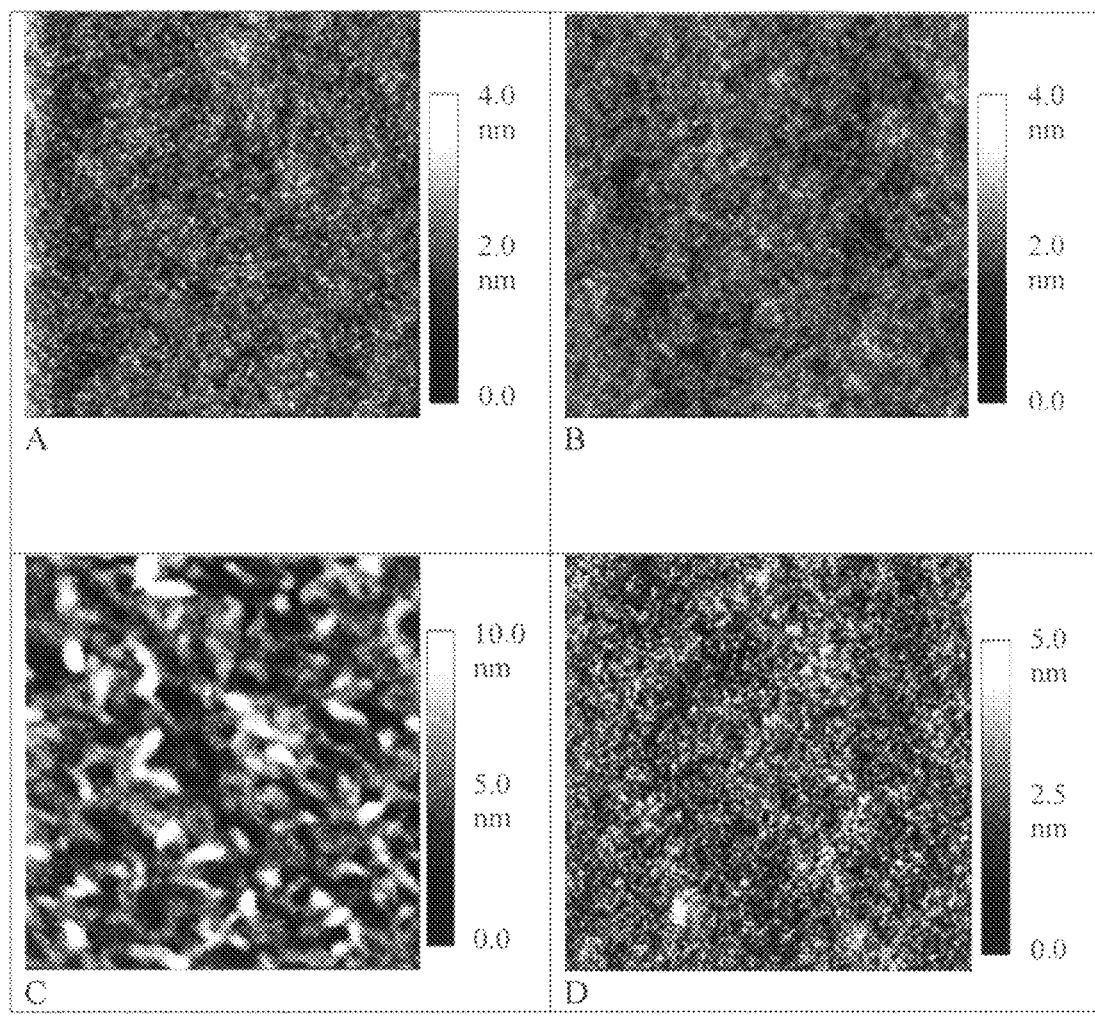
FIGS. 15A, 15B, 15C and 15D are panels of AFM images (2 micron) of G1 (RMS=0.39 nm) (15A), G1-LA (RMS=0.35 nm) (15B), P2 (RMS=1.77 nm) (15C), and P2-LA (RMS=0.69 nm) (15D).

AFM measurements of the devices for G1, P2 and their $B(C_6F_5)_3$ adducts (FIG. 15) revealed that Lewis acid addition results in more uniform films. Because the films remained amorphous, no XRD data could be obtained. $B(C_6F_5)_3$ coordination to the PT unit of this series of oligomers and polymers can cause a narrowing of the optical band gap while retaining the ability of these materials to act as semiconductors.

In conclusion, the synthesis and characterization of a series of novel donor-acceptor oligomers and polymers relevant to the filed of organic semi-conductors are provided. These materials incorporated cyclopentadithiophene as donor unit and pyridalthiadiazole as the acceptor unit. The PT moiety is an exceptional acceptor unit with a high electron affinity giving rise to polymers band gaps approaching 1.26 eV. The pyridine renders these materials capable of binding Lewis acids. Through selective binding of the strong Lewis acid $B(C_6F_5)_3$, new NIR-absorbing materials are readily obtained. This method for altering the band gap of π-conjugated materials may be applied in the field of organic electronics to change the optical, electronic, and morphological behavior of organic materials.

Example 4

Supporting Information for Example 3

General Data: Preparations were carried out on a bench top or under an atmosphere of dry, $O_2$-free $N_2$ employing both Schlenk line techniques and an Vacuum Atmospheres inert atmosphere glove box. Solvents (pentane, toluene, THF, xylenes) were dried over sodium/benzophenone, distilled under vacuum, and stored over molecular sieves (4 Å). Solvents (methylene chloride, chloroform, 1,2-dichlorobenzene (oDCB)) were dried over calcium hydride, distilled under vacuum, and stored over molecular sieves (4 Å). Molecular sieves (4 Å) were purchased from Aldrich Chemical Company and dried at 140° C. under vacuum for 24 hours prior to use. Deuterated solvents were dried over $CaH_2$ ($CD_2Cl_2$, $CDCl_3$, $C_6D_5Br$) or sodium/benzophenone ($C_6D_6$) and vacuum distilled prior to use. All reactants and reagents are commercially available and used as received unless otherwise noted.

Materials: Compound 4H-cyclopenta[2,1-b:3,4-b'] dithiophene (CDT) was purchased from AstarPharma while 4,7-dibromo-pyridal[2,1,3]thiadiazole (PTBr$_2$) was purchased from WUXI Chemical and purified by flash chromatography (10% Et$_3$N in CHCl$_3$) and recrystallization (EtOH) prior to use. Compounds 4,4-bis(2-ethylhexyl)-2,6-bis(trimethylstannyl)-4H-cyclopenta[2,1-b:3,4-b']dithiophene (Me$_3$Sn-CDT$_{EH}$-SnMe$_3$) (25) and 4,4-bis(n-dodecyl)-2,6-bis (trimethylstannyl)-4H-cyclopenta[2,1-b:3,4-b']dithiophene (Me$_3$Sn-CDT$_{C12}$-SnMe$_3$) (26) were prepared by literature methods. Compound 4,4-Bis(n-hexyl)-4H-cyclopenta[2,1-b:3,4-b']dithiophene (CDT$_{C6}$) (27), 4,7-dithienyl[1,2,5]thiadiazolo[3,4-c]pyridine (Th-PT-Th) (28), and 4,7-bis(5-bromo-2-thienyl)[1,2,5]thiadiazolo[3,4-c]pyridine (BrTh-PT-ThBr) (28), were prepared by methods similar to those reported in the literature. $B(C_6F_5)_3$ was purified by treatment with neat Et$_3$SiH, extraction with boiling toluene, and sublimation at 120° C. under vacuum. It is imperative that all Lewis acids be handled using strict anhydrous conditions.

GPC: Gel permeation chromatography (150° C. in 1,2,4-trichlorobenzene) was performed on a Polymer Laboratories PL220 instrument.

NMR: $^1$H, $^{13}$C, $^{11}$B, and $^{19}$F nuclear magnetic resonance (NMR) spectroscopy spectra were recorded on a Bruker Avance-500 MHz spectrometer at 25° C. unless otherwise noted. $^1$H and $^{13}$C NMR spectra are referenced to SiMe$_4$ using the residual solvent peak impurity of the given solvent. $^{11}$B and $^{19}$F NMR experiments were referenced to $BF_3(OEt_2)$, and $CFCl_3$, respectively. Chemical shifts are reported in ppm and coupling constants in Hz as absolute values. DEPT, $^{1}H$-$^{1}H$, and $^{1}H/^{13}C$ correlation experiments were completed for assignment of the carbon atoms.

UV-vis: UV-visible spectroscopy were recorded using wither a Beckman Coulter DU 800 series or Perkin Elmer Lambda 750 spectrophotometer at room temperature unless otherwise noted. All solution UV-vis experiments were run under an $N_2$ atmosphere in teflon capped 1 mm quartz cuvettes using 1,2 dichlorobenzene as the solvent. All oligomer solutions were prepared with a concentration of $4 \times 10^{-4}$ M. All polymer solutions were prepared with a concentration of 0.25 mg per mL in 1,2-dichlorobenzene. Oligomer films were prepared by spin casting the appropriate solution (15 mg/mL in toluene) onto a 15 mm×15 mm×2 mm quartz substrate at 1000 rpm under an atmosphere of $N_2$. Polymer films were prepared by spin casting the appropriate solution (10 mg/mL in chlorobenzene) onto a 15 mm×15 mm×2 mm quartz substrate at 2000 rpm under an atmosphere of $N_2$. Solution combinations of oligomers and $B(C_6F_5)_3$ were prepared by adding an appropriate amount of 0.01 M Lewis acid solution in 1,2-dichlorobenzene to a 0.1 mL aliquot of a 0.01 M dichlorobenzene solution of oligomer and diluting to 2.65 mL to give a solution with a final concentration of 0.000378 M wrt oligomer. For thin films, 1 molar equivalent of $B(C_6F_5)_3$ in 0.5 mL toluene was added to 0.5 mL of a 2% toluene solution of oligomer in a vial and sealed with a teflon cap. The solution was stirred at room temperature for 1 hour before spin casting thin films on quartz at 1000 rpm. Polymer and $B(C_6F_5)_3$ solution mixtures and thin films were prepared in an analogous fashion to the oligomers using 1,2-dichlorobenzene and chlorobenzene as the solvents, respectively.

CHN: Combustion analyses were performed by the MSI analytical lab at the University of California, Santa Barbara.

Electrochemistry: All electrochemical measurements were performed using CHI instrument model 730B in a standard three-electrode, one compartment configuration equipped with Ag/AgCl electrode, Pt wire and Glassy carbon electrode (dia. 3 mm), as the pseudo reference, counter electrode and working electrode respectively. Glassy carbon electrodes were polished with alumina. The cyclic voltammetry (CV) experiments were performed in anhydrous acetonitrile (AcCN) or dichloromethane (DCM) solution with 0.1 M tetrabutylammonium hexafluorophosphate ($TBAPF_6$) as the supporting electrolyte at scan rate 100 mV/s unless otherwise stated. All electrochemical solutions were purged with dry $Ar_2$ for 15 minutes at least to deoxygenate the system. Under these conditions, a $Fc/Fc^+$ standard was calibrated, to be 0.40 V. A mixture of polymer in dry $CHCl_3$ (~3 mg/mL) was used for preparation films at room temperature. Films were prepared by drop-cast onto Glassy carbon electrode for CV measurement. In solution, monomer concentration was about $\sim 10^{-3}$ M.

XPS and UPS: For XPS and UPS (ultraviolet photoelectron spectroscopy) experiments, a Au film 75 nm thick was deposited on a precleaned Si substrate with a thin native oxide. Polymer and oligomer solutions (0.25% chlorobenzene) were then spin-coated at 2000 and 4000 rpm atop a Au film. The total time of spin coating was kept at 60 s for all samples. Film fabrication was done in a $N_2$-atmosphere globe box. To minimize possible influence by exposure to air, the films were then transferred from the $N_2$-atmosphere dry box to the analysis chamber inside an air-free holder. Subsequently, all samples were kept inside a high vacuum chamber overnight, to remove solvent. The XPS and UPS analysis chamber was equipped with a hemispherical electron-energy analyzer (Kratos Ultra Spectrometer), and was maintained at 1.33_10_7 Pa. The XPS was measured using monochromatized Al Ka (hv¼1486.6 eV) excitation, while UPS measurements were carried out using the He I (hv¼21.2 eV) source. The electron energy analyzer was operated at constant pass energy of 20 eV (for XPS) and 10 eV (for UPS). During UPS measurements, a sample bias of 9 V was used in order to separate the sample and the secondary edge for the analyzer. In order to confirm reproducibility of XPS and UPS spectra, these measurements were repeated twice on two sets of samples.

Calculations: All calculations were performed using the Gaussian 03 program (33). Optimized gas-phase structures were obtained using the density functional theory (DFT) method B3LYP (34) in conjunction with 6-31G(d,p) basis set, i.e., B3LYP/6-31G(d,p). California NanoSystems Institute at UCSB is acknowledged for computational resources.

Device fabrication: Hole only diodes were fabricated using the architectures: ITO/PEDOT:PSS/polymer or oligomer/Au for holes. Corning 1737 glass patterned with 140 nm of indium-tin-oxide (ITO) substrates were scrubbed with detergent and sonicated in DI water (3×, 10 min), acetone (1×, 30 min), and isopropyl alcohol (1×, 60 min). The substrates were then dried over nitrogen and placed in a 120° C. oven over night. Prior to use, the substrates were treated by UV-ozone for 60 min. Solutions of G1 and G2 in toluene (2% w/V) were prepared under nitrogen. Solutions of G1-$B(C_6F_5)_3$ and G2-$B(C_6F_5)_3$ in toluene (1:1 by mole, 2% w/V) were prepared under nitrogen. Solutions of P1, P2, and P3 in chlorobenzene (1% w/V) were prepared under nitrogen. Solutions of P1-$B(C_6F_5)_3$, P2-$B(C_6F_5)_3$, P3-$B(C_6F_5)_3$ in chlorobenzene (1:1 by weight, 1% w/V) were prepared under nitrogen. The polymer solutions were stirred and heated at 60° C. overnight. For hole-only diodes, a ~55 nm thick layer of poly(3,4-ethylenedioxythiophene):polystyrene sulfonic acid (PEDOT:PSS, Baytron P 4083, H.C. Starck Inc.) was spun cast onto cleaned ITO at 5000 rpm for 60 s in air and annealed at 140° C. for 45 min. The polymer or oligomer solutions, passed through a Whatman 1 μm PTFE membrane filter, was spun cast onto the PEDOT:PSS layer at 800 rpm for 60 s. An 85 nm layer of Au was thermally evaporated as electrode. I-V curves for the devices were obtained using a Keithley 4200 Semiconductor Characterization System under Nitrogen. Mobilities were extracted by fitting the current density-voltage curves using the Mott-Gurney relationship (space charge limited current). $J=(9/8) \epsilon\epsilon_0 \mu_{SCLC}(V^2/L^3)$. Where, J is the current density, $\epsilon_0$ is the vacuum permittivity, $\mu_{SCLC}$ is the charge carrier mobility, V is the potential across the device and L is the thickness of the organic film. Film thicknesses were measured using an AMBIOS Technology XP-100 profilometer. Average film thicknesses are as follows: G1=90 nm, G2=80 nm, P1=92 nm, P2=99 nm, P3=67 nm, G1-$B(C_6F_5)_3$=117 nm, G2-$B(C_6F_5)_3$=94 nm, P2-$B(C_6F_5)_3$=110 nm, P2-$B(C_6F_5)_3$=142 nm, P3-$B(C_6F_5)_3$=101 nm.

Film Characterization: AFM images were obtained in tapping mode using a Multimode microscope with a Nanoscope IIIa controller (Veeco) operated in Nitrogen glovebox with silicon probes having resonant frequency of ~75 kHz and spring constant of 1-5 N/m (Budget Sensors).

Syntheses

Synthesis of 4,4-Dihexyl-cyclopenta[2,1-b:3,4-b']dithiophene ($CDT_{C6}$): To a solution of 4H-Cyclopenta[2,1-b:3,4-b']dithiophene (CDT) (1.63 g, 9.14 mmol) in dimethyl sulfoxide (50 mL) was added hexyl bromide (3.1 g, 18.9 mmol) and a catalytic amount of potassium iodide (50 mg). The mixture was purged with argon for 10 minutes followed by the slow addition of solid potassium hydroxide (2 g). The now dark green mixture was stirred in the dark at room temperature for 72 hours. The mixture was then poured into de-ionized water (150 mL) and the organic phase extracted with diethyl ether (4×100 mL). The organic phases were collected and washed with brine (100 mL) and a saturated ammonium chloride solution (100 mL). The organic phase was dried over magnesium sulphate, filtered, and concentrated to give the crude product as yellow oil. Purification via flash chromatography with hexanes (monitored at 254 nm, collected at 320 nm) and drying under high vacuum for 48 hours gave pure product as colorless oil. Yield 2.8 g (88%). $^1$H NMR (500 MHz, CDCl$_3$): δ=7.15 (d, 2H, $^3J_{H-H}$=5 Hz), 6.94 (d, 2H, $^3J_{H-H}$=5 Hz), 1.84 (m, 4H, C—CH$_2$), 1.19 (m, 12H, alkyl-CH$_2$), 0.95 (m, 4H, alkyl-CH$_2$), 0.82 (m, 6H, alkyl-CH$_3$).

Synthesis of 5-(trimethylstannyl)-4,4-bis(hexyl)-4H-cyclopenta[2,1-b;3,4-b']dithiophene (Me$_3$Sn-CDT$_{C6}$): A dry three-neck round bottom flask was equipped with a Schlenk adapter, dropping funnel, and rubber septum. Under argon, compound CDT$_{C6}$ (2.80, 8.07 mmol) was dissolved in dry THF (200 mL) and cooled −78° C. using a dry ice/acetone cold bath. A solution of t-butyllithium (1.7 M pentane, 5.22 mL, 8.87 mmol) diluted with dry pentane (30 mL) was then added dropwise over 20 minutes via a dropping funnel. The dropping funnel was rinsed with dry pentane (30 mL) to ensure all lithium reagent was transferred to the reaction vessel. The reaction was stirred at −78° C. under argon for 2 hours. A solution of trimethyltin chloride (1.93 g, 9.68 mmol) in dry pentane (30 mL) was then added dropwise over 5 minutes via a dropping funnel. The dropping funnel was rinsed with dry pentane (30 mL) to ensure all tin reagent was transferred to the reaction vessel. The reaction was stirred at −78° C. under argon for 1 hour and subsequently warmed to room temperature and stirred for a further 3 hours. The mixture was then poured into de-ionized water (300 mL) and the organic phase extracted with hexanes (3×100 mL). The organic phases were collected and washed with de-ionized water (5×100 mL), dried over magnesium sulphate, filtered, and concentrated to give the product as yellow oil. Yield 4.05 g (98%). $^1$H NMR (500 MHz, CDCl$_3$): δ=7.12 (d, 1H, $^3J_{H-H}$=5 Hz), 6.96 (s, 1H), 6.93 (d, 1H, $^3J_{H-H}$=5 Hz), 1.82 (m, 4H, C—CH$_2$), 1.21 (m, 4H, alkyl-CH$_2$), 1.16 (m, 8H, alkyl-CH$_2$), 1.00 (m, 4H, alkyl-CH$_2$), 0.83 (t, 6H, $^3J_{H-H}$=7 Hz, alkyl-CH$_3$), 0.40 (s, d, 9H, $^2J_{H-Sn}$=57 Hz, Sn—CH$_3$). $^{13}$C NMR (500 MHz, CDCl$_3$): δ=160.69, 158.32, 142.35, 137.60, 136.80, 129.47, 124.26, 122.01 (aromatic C), 52.91 (quaternary, bridged C), 37.87, 31.81, 29.95, 24.72, 22.82 (CH$_2$), 14.25 (CH$_3$), 7.84 (s, d, $^1J_{C-Sn}$=362 Hz, Sn—CH$_3$). $^{119}$Sn NMR (500 MHz, CDCl$_3$): δ=−26.7.

Synthesis of 4,7-dithienyl[1,2,5]thiadiazolo[3,4-c]pyridine (Th-PT-Th): A 5 mL microwave tube was charged with 4,7-dibromo-pyridal[2,1,3]thiadiazole (PTBr$_2$, 0.556 g, 1.885 mmol), 2-(tributylstannyl)thiophene (Bu$_3$Sn—Th, 1.477 g, 3.957 mmol), Pd(PPh$_3$)$_4$ (0.020 g, 0.018 mmol), toluene (3 mL), and sealed with a teflon cap. The reaction mixture was heated to 120° C. for 3 minutes, 140° C. for 3 minutes, and 170° C. for 36 minutes, using a Biotage microwave reactor. Upon cooling, the residue was passed through a short silica plug eluting with methylene chloride (200 mL). All volatiles were removed in vacuo to give the crude product as a red solid. The solid was slurried in MeOH (100 mL), sonicated for 10 minutes, and filtered. The solid was washed with copious amounts of MeOH and then dried under vacuum for 24 hours. The product was collected as a bright red solid. Recovered yield: 535 mg (94%). $^1$H NMR (CD$_2$Cl$_2$): δ 8.81 (s, 1H, PT-CH), 8.68 (d, $^3J_{H-H}$=4 Hz, 1H, Th'—CH), 8.11 (d, $^3J_{H-H}$=4 Hz, 1H, Th—CH), 7.61 (d, $^3J_{H-H}$=5 Hz, 1H, Th'—CH), 7.51 (d, $^3J_{H-H}$=5 Hz, 1H, Th—CH), 7.27 (dd, $^3J_{H-H}$=4 Hz, $^3J_{H-H}$=4 Hz 1H, Th'—CH), 7.23 (dd, $^3J_{H-H}$=4 Hz, $^3H_{H-H}$=4 Hz 1H, Th—CH), $^{13}$C{$^1$H} NMR (CD$_2$Cl$_2$): 155.50, 148.62, 146.91, 142.53 (s, quaternary), 141.28 (s, PT-CH), 137.18 (s, quaternary), 131.97 (s, Th'—CH), 131.00 (s, Th'—CH), 129.40 (s, Th—CH), 128.61 (s, Th—CH), 128.38 (s, Th'—CH), 127.88 (s, Th—CH), 121.00 (s, quaternary). Anal. Calcd. for C$_{13}$H$_7$N$_3$S$_3$: C, 51.80; H, 2.34; N, 13.94. Found: C, 51.8; H, 2.40; N, 13.7%. UV-vis: (o-DCB) λ$_{max}$=302, 470 nm, λ$_{onset}$=550 nm, ϵ=22150 cm$^{-1}$M$^{-1}$. PL: (o-DCB) λ$_{max}$=607 nm. HRMS (EI) m/z, calcd for C$_{13}$H$_7$N$_3$S$_3$ (M$^+$): 300.98; found: 301.

Synthesis of 4,7-bis(5-bromo-2-thienyl)[1,2,5]thiadiazolo[3,4-c]pyridine (Br—Th-PT-Th—Br): A 250 mL round bottom flask was charged with 4,7-dithienyl[1,2,5]thiadiazolo[3,4-c]pyridine (Th-PT-Th, 0.500 g, 1.662 mmol), n-bromosuccinimide (NBS, 0.700 mg, 3.932 mmol), N-N-dimethyl formamide (50 mL), chloroform (100 mL), and capped with a rubber septum. The reaction mixture was stirred for 72 hours in the dark. The reaction mixture was precipitated into MeOH (400 mL) and stirred for 1 hour. The precipitate was collected via filtration and washed with copious amounts of MeOH and dried under vacuum for 12 hours. Crude product was purified via flash chromatography (hexanes/methylene chloride) to give pure product as a red solid. Recovered yield: 600 mg (79%). $^1$H NMR (CD$_2$Cl$_2$): δ 8.80 (s, 1H, PT-CH), 8.45 (d, $^3J_{H-H}$=5 Hz, Th'—CH), 7.87 (d, $^3J_{H-H}$=5 Hz, 1H, BrTh—CH), 7.29 (d, $^3J_{H-H}$=5 Hz, Th'—CH), 7.22 (d, $^3J_{H-H}$=5 Hz, Th—CH). Anal. Calcd. for C$_{13}$H$_5$Br$_2$N$_3$S$_3$: C, 34.00; H, 1.10; N, 9.15. Found: C, 33.6; H, 1.13; N, 8.86%. HRMS (EI) m/z, calcd for C$_{13}$H$_5$Br$_2$N$_3$S$_3$ (M$^+$): 456.8; found: 457.

Synthesis of {Bis(4,4-bis(hexyl)-4H-cyclopenta[2,1-b;3,4-b']dithiophene)}-4,7-pyridal[2,1,3]thiadiazole (CDT-PT-CDT): A 5 mL microwave tube was charged with 4,7-dibromo-pyridal[2,1,3]thiadiazole (PTBr$_2$, 0.250 g, 0.848 mmol), 5-(trimethylstannyl)-4,4-bis(hexyl)-4H-cyclopenta[2,1-b;3,4-b']dithiophene (Me$_3$Sn-CDT, 0.873 g, 1.714 mmol), Pd(PPh$_3$)$_4$ (0.010 g, 0.009 mmol), toluene (3 mL), and sealed with a teflon cap. The reaction mixture was heated to 120° C. for 3 minutes, 140° C. for 3 minutes, and 170° C. for 36 minutes, using a Biotage microwave reactor. Upon cooling, the residue was passed through a short silica plug eluting with methylene chloride (100 mL). All volatiles were removed in vacuo to give the crude product as a blue residue. To the residue was added MeOH (100 mL), the mixture sonicated for 10 minutes, and the MeOH decanted off. The crude product was then subjected to flash chromatography on a silica gel column using a hexane/CH$_2$Cl$_2$ gradient. The first fraction was combined and all solvent was removed in vacuo to give a blue film. MeOH was added (150 mL), the mixture sonicated for 10 minutes, filtered and dried under vacuum for 12 hours to give the product as a blue solid. Recovered yield: 503 mg (72%). $^1$H NMR (CD$_2$Cl$_2$): δ 8.78 (s, 1H, Th—CH), 8.57 (s, 1H, Th'—CH), 8.05 (s, 1H, PT-CH), 7.35 (d, $^3J_{H-H}$=5 Hz, 1H, Th'—CH), 7.28 (d, $^3J_{H-H}$=5 Hz, 1H, Th—CH), 7.04 (d, $^3J_{H-H}$=6 Hz, 1H, Th'—CH), 7.01 (d, $^3J_{H-H}$=6 Hz, 1H, Th—CH), 1.96 (m, 8H, C—CH$_2$), 1.17 (m, 24H, alkyl-CH$_2$), 1.03 (m, 8H, alkyl-CH$_2$), 0.86 (m, 12H, alkyl-CH$_3$). $^{13}$C{$^1$H} NMR (CD$_2$Cl$_2$): 161.11, 160.64, 159.81, 155.21, 148.59, 146.41, 143.06, 142.79 (s, quaternary), 140.32 (s, PT-CH), 139.33, 137.50, 137.19, 137.03 (s, quaternary), 127.97 (s, Th'—CH), 126.65 (s, Th'—CH), 126.63 (s, Th—CH), 122.63 (s, Th—CH), 122.50 (s, Th'—CH), 122.43 (s, Th—CH), 122.20, 121.07 (s, quaternary), 54.57 (s, quaternary, bridged C'), 54.47 (s, quaternary, bridged C), 38.43 (m, C—CH$_2$), 32.22 (s, alkyl-CH$_2$), 30.28 (s, alkyl-CH$_2$), 25.17 (s, alkyl- $CH_2$), 23.18 (s, alkyl-$CH_2$), 14.37 (s, alkyl-$CH_3$). Anal. Calcd. for $C_{47}H_{59}N_3S_5$: C, 68.32; H, 7.20; N, 5.09. Found: C, 68.10; H, 7.25; N, 5.13%. UV-vis: (o-DCB) $\lambda_{max}$=386, 618 nm, $\lambda_{onset}$=766 nm, $\epsilon$=35440 $cm^{-1}M^{-1}$. PL: (o-DCB, e600 nm) $\lambda_{max}$=745 nm. MS (FAB) m/z, calcd for $C_{47}H_{59}N_3S_5$ ($M^+$): 825.33; found: 825.

Synthesis of Bis{2-thienyl-(4,4-bis(hexyl)-4H-cyclopenta[2,1-b;3,4-b']dithiophene)}-4,7-pyridal[2,1,3]thiadiazole (CDT-Th-PT-Th-CDT): A 5 mL microwave tube was charged with 4,7-bis(5-bromo-2-thienyl)[1,2,5]thiadiazolo[3,4-c]pyridine (Br—Th-PT-Th—Br, 0.287 g, 0.628 mmol), 5-(trimethylstannyl)-4,4-bis(hexyl)-4H-cyclopenta[2,1-b;3,4-b']dithiophene ($Me_3$Sn-CDT, 0.670 g, 1.316 mmol), $Pd(PPh_3)_4$ (0.020 g, 0.018 mmol), toluene (3 mL), and sealed with a teflon cap. The reaction mixture was heated to 120° C. for 3 minutes, 140° C. for 3 minutes, and 170° C. for 36 minutes, using a Biotage microwave reactor. Upon cooling, the residue was passed through a short silica plug eluting with methylene chloride (400 mL). All volatiles were removed in vacuo to give the crude product as a blue-green residue. To the residue was added MeOH (300 mL), the mixture sonicated for 10 minutes, and the MeOH decanted off. The crude product was then subjected to flash chromatography on a silica gel column using a hexane/$CH_2Cl_2$ gradient. The first fraction was combined and all solvent was removed in vacuo to give a blue-green film. MeOH was added (300 mL), the mixture sonicated for 10 minutes, filtered and dried under vacuum for 12 hours to give the product as a purple solid. Recovered yield: 480 mg (77%). $^1$H NMR ($CD_2Cl_2$): δ 8.78 (s, 1H, PT-CH), 8.58 (d, $^3J_{H-H}$=4 Hz, 1H, Th'—CH), 8.06 (d, $^3J_{H-H}$=4 Hz, 1H, Th—CH), 7.31 (d, $^3J_{H-H}$=4 Hz, 1H, Th'—CH), 7.29 (s, 1H, CDT'-CH), 7.27 (m, 2H, CDT'-CH, CDT-CH) 7.24 (d, $^3J_{H-H}$=4 Hz, 1H, Th—CH), 7.22 (s, 1H, CDT-CR), 7.00 (m, 2H, CDT'-CH, CDT-CH), 1.92 (m, 8H, C—$CH_2$), 1.20 (m, 24H, alkyl-$CH_2$), 1.05 (m, 8H, alkyl-$CH_2$), 0.82 (m, 12H, alkyl-$CH_3$). $^{13}C\{^1H\}$ NMR ($CD_2Cl_2$): 159.77, 159.95, 159.60, 159.22, 155.23, 148.66, 145.94, 143.99 (s, quaternary), 140.89 (s, PT-CH), 140.83, 140.15, 138.01, 137.21, 137.13, 136.77, 136.70, 135.24 (s, quaternary), 133.47 (s, Th'—CH), 129.21 (s, Th—CH), 126.56 (s, CDT'-CH), 126.19 (s, CDT-CH), 124.73 (s, Th'—CH), 124.01 (s, Th—CH), 122.38 (m, CDT'-CH, CDT-CH), 120.38 (s, quaternary), 120.28 (s, CDT'-CH), 119.62 (s, CDT-CH), 54.55 (s, quaternary, bridged C'), 54.42 (s, quaternary, bridged C), 38.38 (m, C—$CH_2$), 32.23 (s, alkyl-$CH_2$), 30.30 (s, alkyl-$CH_2$), 25.13 (s, alkyl-$CH_2$), 23.21 (s, alkyl-$CH_2$), 14.41 (s, alkyl-$CH_3$). Anal. Calcd. for $C_{55}H_{63}N_3S_7$: C, 66.69; H, 6.41; N, 4.24. Found: C, 66.0; H, 6.11; N, 4.60%. UV-vis: (o-DCB) $\lambda_{max}$=418, 626 nm, $\lambda_{onset}$=768 nm, s=37500 $cm^{-1}$ $M^{-1}$. PL: (o-DCB, e600 nm) $\lambda_{max}$=798 nm. MS (FAB) m/z, calcd for $C_{55}H_{63}N_3S_7$ ($M^+$): 989.31; found: 990.

Synthesis of {Bis(4,4-bis(hexyl)-4H-cyclopenta[2,1-b:3,4-b']dithiophene)}-4,7-benzo[2,1,3]thiadiazole (CDT-BT-CDT): A 5 mL microwave tube was charged with 4,7-dibromo-benzo[2,1,3]thiadiazole ($BTBr_2$, 0.161 g, 0.548 mmol), 5-(trimethylstannyl)-4,4-bis(hexyl)-4H-cyclopenta[2,1-b;3,4-b']dithiophene ($Me_3$Sn-CDT, 0.557 g, 1.09 mmol), $Pd(PPh_3)_4$ (0.010 g, 0.009 mmol), toluene (3 mL), and sealed with a teflon cap. The reaction mixture was heated to 120° C. for 3 minutes, 140° C. for 3 minutes, and 170° C. for 36 minutes, using a Biotage microwave reactor. Upon cooling, the residue was passed through a short silica plug eluting with methylene chloride (100 mL). All volatiles were removed in vacuo to give the crude product as a purple residue. To the residue was added MeOH (100 mL), the mixture sonicated for 10 minutes, and the MeOH decanted off. The crude product was then subjected to flash chromatography on a silica gel column using a hexane/$CH_2Cl_2$ gradient. The first fraction was combined and all solvent was removed in vacuo to give a purple film. MeOH was added (150 mL), the mixture sonicated for 10 minutes, filtered and dried under vacuum for 12 hours to give the product as a purple solid. Recovered yield: 345 mg (77%). NMR ($CD_2Cl_2$): δ 8.05 (s, 2H, benzothiadiazole-CH), 7.87 (s, 2H, thiophene-CH), 7.27 (d, $^3J_{H-H}$=5 Hz, 2H, thiophene-CH), 7.06 (d, $^3J_{H-H}$=5 Hz, 2H, thiophene-CH), 1.95 (m, 8H, $CH_2$), 1.23-1.13 (m, 24H, $CH_2$), 1.08-1.99 (m, 8H, $CH_2$), 0.81 (t, 12H, $^3J_{H-H}$=7 Hz, $CH_3$). $^{13}C\{^1H\}$NMR ($CD_2Cl_2$): 159.65, 159.54, 152.97, 140.05, 139.09, 137.10, 126.40 (s, quaternary), 126.34 (s, thiophene-CH), 124.76 (s, benzothiadiazole-CH), 122.42 (s, thiophene-CH), 122.36 (s, thiophene-CH), 38.39 (s, C—$CH_2$), 32.16 (s, alkyl-$CH_2$), 30.24 (s, alkyl-$CH_2$), 25.11 (s, alkyl-$CH_2$), 23.10 (s, alkyl-$CH_2$), 14.35 (s, alkyl-$CH_3$). Anal. Calcd. for $C_{47}H_{59}N_3S_5$: C, 69.85; H, 7.33; N, 3.39. Found: C, 69.7; H, 7.21; N, 3.58%. UV-vis: ($CHCl_3$) $\lambda_{max}$=378, 568 nm, $\lambda_{onset}$=664 nm, c=27790 $cm^{-1}M^{-1}$. Optical bandgap=1.87 eV. HRMS (FAB) m/z, calcd for $C_{47}H_{59}N_3S_5$ ($M^+$): 824.34; found: 824.

Polymer Synthesis General: The polymers were prepared following a previously reported microwave assisted polymerization technique involving stoichiometric adjustment to optimize molecular weights. The stoichiometric adjustment procedure is used to compensate for possible impurities in the distannane monomers as a result of them being viscous oils that are difficult to purify. It was determined for both distannane monomers 1 and 2 that an apparent excess of 5 mol % should be used in polymerizations. Monomer loadings were such that the theoretical yield of copolymer would be ~250 mg. The two monomers were carefully weighed within a tenth of an mg and added to a 2-5 mL microwave tube. The tube was transferred into a glovebox where $Pd(PPh_3)_4$ (~5 mol % relative to Br) and 2 mL of Xylenes were added. The tube was sealed, removed from the glovebox and subjected to the following reaction conditions in a microwave reactor: 100° C. for 1 min, 150° C. for 1 min and 200° C. for 20 min. After this time the reaction was allowed to cool leaving a viscous liquid containing some solid material. The mixture was dissolved in hot 1,2-dichlorobenzene, then precipitated into methanol and collected via centrifugation. The residual solid was loaded into a cellulose extraction thimble and washed successively with methanol (4 hrs), hexanes (4 hrs), and acetone (2 hrs). The remaining polymer was dried on a high vacuum line overnight.

Poly[(4,4-didodecylcyclopenta-[2,1-b:3,4-b']dithiophene)-2,6-diyl-alt-([1,2,5]thiadiazolo[3,4-c]pyridine)-4,7-diyl] (P1): 345.2 mg (0.411 mmol) of $Me_3$Sn-$CDT_{C12}$-$SnMe_3$, 115.4 mg (0.391 mmol) of Br-PT-Br and 12 mg of $Pd(PPh_3)_4$ were added to the microwave tube and subject to the procedure outline above. Yield: 212 mg (84%). $M_n$=20 kg/mol, PDI=2.0. Anal. Calcd. for $C_{40}H_{59}N_3S_3$: C, 70.85; H, 8.77; N, 6.20. Found: C, 68.8; H, 8.34; N, 6.29. $^1$H NMR (o-$C_6D_4Cl_2$, 400K): δ 8.8 (s, 1H, CH), 8.65 (s, 1H, CH), 8.0 (s, 1H, CH), 1.8 (br m, 4H, $CH_2$), 1.3-1.1 (br m, 40H, $CH_2$), 0.9 (br m, 6H, $CH_3$).

Poly[(4,4-bis(2-ethylhexyl)cyclopenta-[2,1-b:3,4-b']dithiophene)-2,6-diyl-alt-([1,2,5]thiadiazolo[3,4-c]pyridine)-4,7-diyl] (P2): 357.0 mg (0.490 mmol) of $Me_3$Sn-$CDT_{EH}$-$SnMe_3$, 137.7 mg (0.467 mmol) of Br-PT-Br and 15 mg of $Pd(PPh_3)_4$ were added to the microwave tube and subjected to the procedure outlined above. Batch 1: Yield: 188 mg (75%), $M_n$=16 kg/mol, PDI=2.0. Anal. Calcd. for $C_{32}H_{43}N_3S_3$: C, 67.92; H, 7.66; N, 7.43. Found: C, 65.4; H, 6.63; N, 7.58. $^1$H NMR ($C_6D_5$Br): δ 8.94 (s, 1H, CH), 8.85 (s, 1H, CH), 8.33 (s, 1H, CH), 2.28 (br m, 4H), 1.19 (br m, 16H), 0.84 (br m, 7H), 0.77 (br m, 7H). $^{13}C\{^1H\}$ NMR ($C_6D_5Br$) partial: 154.7, 148.3, 128.4, 54.4, 43.5, 35.6, 34.5, 28.8, 27.7, 23.1, 14.3, 11.1. Batch 2: $M_n$=30 kg/mol, PDI=2.0.

Poly[(4,4-bis(2-ethylhexyl)cyclopenta-[2,1-b:3,4-b'] dithiophene)-2,6-diyl-alt-(4',7'-bis(2-thienyl)-[1,2,5]thiadiazolo[3,4-c]pyridine)-5,5-diyl] (P3): 273.1 mg (0.375 mmol) of $Me_3Sn$-$CDT_{EH}$-$SnMe_3$, 164.0 mg (0.357 mmol) of Br—Th-PT-Th—Br and 10 mg of $Pd(PPh_3)_4$ were added to the microwave tube and subject to the procedure outline above. Yield: 220 mg (88%). $M_n$=18 kg/mol, PDI=2.0. Anal. Calcd. for $C_{40}H_{47}N_3S_5$: C, 65.80; H, 6.49; N, 5.76. Found: C, 63.8; H, 5.77; N, 5.77. NMR (o-$C_6D_4Cl_2$, 400K): δ 8.62 (s, 1H, CH), 8.45 (s, 1H, CH), 7.96 (s, 1H, CH), 7.32 (s, 2H, CH), 7.27 (s, 2H, CH), 2.01 (br m, 4H), 1.10 (br m, 17H), 0.75 (br m, 13H).

General Procedure for BCF Reactions

NMR Characterization of CDT-PT-CDT-($B(C_6F_5)_3$): A glass NMR tube was charged with $B(C_6F_5)_3$ (0.012 g, 0.023 mmol), CDT-PT-CDT (0.020 g, 0.023 mmol) and $CD_2Cl_2$ (0.75 mL). The resulting blue-green solution was vigorously shaken for 5 minutes and the product analyzed via NMR spectroscopy. Spectra at 300K broadened due to equilibrium between free and bound $B(C_6F_5)_3$, Keq=0.15. $^1H$ NMR ($CD_2Cl_2$, 300K): δ 8.82 (br, 1H, CH), 8.56 (br, 1H, CH), 8.82 (br, 1H, CH), 8.07 (s, 1H, CH), 7.36 (d, 1H, $^3J_{H-H}$=7 Hz, CH), 7.30 (br, 1H, CH), 7.05 (d, 1H, $^3J_{H-H}$=5 Hz, CH), 7.03 (d, 1H, $^3J_{H-H}$=5 Hz, CH), 1.97 (m, 8H, C—$CH_2$), 1.21 (m, 24H, alkyl-$CH_2$), 1.07 (m, 8H, alkyl-$CH_2$), 0.83 (m, 12H, alkyl-$CH_3$). $^{19}F$ NMR ($CD_2Cl_2$, 300K): δ −128.2 (br s, 6F, ortho-$C_6F_5$), −143.8 (br s, 6F, para-$C_6F_5$), −160.9 (br s, 6F, meta-$C_6F_5$). $^1H$ NMR ($CD_2Cl_2$, 230K): δ 9.00 (m, 1H, PT-CH), 8.17 (s, 1H, Th—CH), 7.40 (d, $^3J_{H-H}$=5 Hz, 1H, Th—CH), 7.33 (d, $^3J_{H-H}$=5 Hz, 1H, Th—CH), 7.02 (m, 2H, Th—CH), 6.83 (s, 1H, Th—CH), 1.89 (m, 4H, C—$CH_2$), 1.73 (m, 2H, C—$CH_2$), 1.48 (m, 2H, C—$CH_2$), 1.23-0.94 (m, 32H, alkyl-$CH_2$), 0.82 (m, 6H, alkyl-$CH_3$). 0.76 (m, 6H, alkyl-$CH_3$). $^{13}C\{^1H\}$ NMR ($CD_2Cl_2$, 230K): 161.1, 160.8, 157.7, 154.5, 153.0 (s, quaternary), 148.8 (dm, CF), 147.6 (s, quaternary), 146.8 (dm, CF), 142.8, 142.5 (s, quaternary), 136.6 (CH), 135.5, 134.2, 133.8 (s, quaternary), 128.9, 128.5, 127.8, 126.4 (CH), 124.5, 122.3 (s, quaternary), 122.0 (CH), 53.9 (s, quaternary, bridged C), 53.3 (s, quaternary, bridged C), 37.7, 37.6, 35.9, 35.8, 31.9, 31.83, 31.81, 31.4, 29.84, 29.82, 29.79, 24.9, 24.63, 24.56, 24.50, 23.1, 22.90, 22.88, 14.21, 14.19, 14.18, 14.16 (s, alkyl $CH_2$ and $CH_3$). $^{11}B\{^1H\}$ NMR ($CD_2Cl_2$, 230K): 6-4 (bs). $^{19}F$ NMR ($CD_2Cl_2$, 230K): δ −125.35 (m, 1F, ortho-$C_6F_5$), −128.43 (m, 1F, $^3J_{F-F}$=22 Hz, ortho-$C_6F_5$), −130.53 (m, 1F, ortho-$C_6F_5$), −132.20 (m, 1F, $^3J_{F-F}$=22 Hz, ortho-$C_6F_5$), −134.62 (m, 1F, $^3J_{F-F}$=22 Hz, ortho-$C_6F_5$), −136.07 (m, 1F, ortho-$C_6F_5$), −154.23 (m, 1F, $^3J_{F-F}$=24 Hz, para-$C_6F_5$), −156.83 (m, 1F, $^3J_{F-F}$=24 Hz, para-$C_6F_5$), −157.73 (m, 1F, $^3J_{F-F}$=24 Hz, para-$C_6F_5$), −161.83 (m, 1F, $^3J_{F-F}$=22 Hz, meta-$C_6F_5$), −162.63 (m, 1F, meta-$C_6F_5$), −164.17 (m, 1F, $^3J_{F-F}$=22 Hz, meta-$C_6F_5$), −164.98 (m, 2F, meta-$C_6F_5$), −165.48 (m, 1F, $^3J_{F-F}$=24 Hz, meta-$C_6F_5$).

NMR Characterization of CDT-Th-PT-Th-CDT-($B(C_6F_5)_3$): A glass NMR tube was charged with $B(C_6F_5)_3$ (0.012 g, 0.023 mmol), CDT-PT-CDT (0.025 g, 0.023 mmol) and $CD_2Cl_2$ (0.75 mL). The resulting green-blue solution was vigorously shaken for 5 minutes and the product analyzed via NMR spectroscopy. Spectra at 300K broadened due to equilibrium between free and bound $B(C_6F_5)_3$, Keq=0.44. $^1H$ NMR ($CD_2Cl_2$, 230K): δ 9.05 (m, 1H, PT-CH), 7.88 (s, 1H, Th—CH), 7.29 (m, 1H, Th—CH), 7.27 (m, 1H, Th—CH), 7.25 (m, 1H, Th—CH), 7.23 (s, 1H, Th—CH), 7.00 (d, 1H, $^3J_{H-H}$=5 Hz, Th—CH), 6.98 (d, 1H, $^3J_{H-H}$=5 Hz, Th—CH), 6.96 (d, 1H, $^3J_{H-H}$=5 Hz, Th—CH), 6.94 (s, 1H, Th—CH), 6.83 (br s, 1H, Th—CH), 1.84 (m, 8H, C—$CH_2$), 1.18-1.04 (m, 24H, alkyl-$CH_2$), 0.95-0.81 (m, 8H, alkyl-$CH_3$). 0.76 (m, 12H, alkyl-$CH_3$). $^{11}B\{^1H\}$ NMR ($CD_2Cl_2$, 230K): δ −5 (bs), $^{19}F$ NMR ($CD_2Cl_2$, 230K): δ −125.49 (m, 1F, ortho-$C_6F_5$), −128.79 (br s, 1F, ortho-$C_6F_5$), −130.24 (m, 1F, ortho-$C_6F_5$), −132.24 (m, 2F, ortho-$C_6F_5$), −136.67 (br s, 1F, ortho-$C_6F_5$), −154.46 (m, 1F, para-$C_6F_5$), −157.08 (m, 1F, para-$C_6F_5$), −157.63 (m, 1F, para-$C_6F_5$), −161.80 (m, 1F, meta-$C_6F_5$), −162.96 (m, 1F, meta-$C_6F_5$), −164.27 (m, 1F, meta-$C_6F_5$), −164.68 (m, 2F, meta-$C_6F_5$), −164.88 (m, 1F, $^3J_{F-F}$=24 Hz, meta-$C_6F_5$).

Attempted NMR Characterization of P2-($B(C_6F_5)_3$): A glass NMR tube was charged with $B(C_6F_5)_3$ (0.010 g), P2 (0.025 g, 0.023 mmol) and $C_6D_5Br$ (1 mL), forming a 2% by weight solution. The resulting green solution was vigorously shaken for 5 minutes and the reaction analyzed via NMR spectroscopy. The $^1H$ NMR spectrum exhibited two significantly broadened aromatic resonances compared to neat P2 solution, while the $^{19}F$ NMR spectrum showed primary resonances attributed to free $B(C_6F_5)_3$. Upon cooling to 260K, the four broad aromatic resonances could be detected in the $^1H$ NMR spectrum, while several new small broad resonances emerged in the $^{19}F$ NMR spectrum. These results indicated that exchange likely exits between free and bound (P2-$B(C_6F_5)_3$ adduct) and $B(C_6F_5)_3$ at room temperature, with the unbound form being significantly favored. Upon cooling adduct formation begins to become favored. Due to the fact that P2 is only soluble in halogenated aromatic solvents that freeze below 250K, further investigation of this process was not undertaken.

Regeneration of oligomers G1 and G2: Recovery of oligomers was identical and thus only the method for one is reported. Solutions of G1-$B(C_6F_5)_3$ were collected into a flask and diluted with excess pyridine to quench all borane. All volatiles were removed in vacuo. The resulting solids were slurred in hexanes and the filtered through celite. The precipitate was discarded and the filtrate loaded onto silica and eluted with hexanes via flash chromatography. The hexane fractions absorbing at 365 nm were collected and reduced to give crude G1. Precipitation in methanol and collection by filtration gave pure G1, as determined by NMR spectroscopy.

Regeneration of polymers: Recovery of polymers were identical and thus only the method for one is reported. Solutions of P1-$B(C_6F_5)_3$ were collected into a flask and diluted with excess pyridine to quench all borane. The solutions were concentrated under vacuum and methanol (~50 mL per ml of polymer solution) was added resulting in precipitation. The precipitate was collected via filtration and washed with copious amounts of methanol, acetone, and hexanes. Upon drying under high vacuum, P1 was obtained as determined by absorption spectroscopy and elemental analysis.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the claims.

REFERENCES

The following publications are all incorporated by reference herein.

1. Roncali, J. *Macromol. Rapid Commun.* 2007, 28, 1761.
2. Gratzel, M. J. Photochem. Photobiol. C Photochem. Rev. 2003, 4, 145.
3. Scharber, M. C.; Wuhlbacher, D.; Koppe, M.; Denk, P.; Waldauf C.; Heeger, A. J.; Brabec, C. L. *Adv. Mat.* 2006, 18, 789.
4. Dennler, G.; Scharber, M. C.; Brabec, C. J. *Adv. Mater* 2009, 21, 1.
5. Hou, J.; Chen, H. Y.; Zhang, S.; Li, G.; Yang, Y. *J. Am. Chem. Soc.* 2008, 130, 16144.

6. Peet, J.; Kim, Y.; Coates, N. E.; Ma, W. L.; Moses, D.; Heeger, A. J.; Bazan, G. C. *Nat. Mat.* 2007, 6, 497.
7. Kim, J. Y.; Lee, K.; Coates, N. E.; Moses D.; Nguyen, T. Q.; Dante, M.; Heeger, A. J. *Science* 2007, 317, 222.
8. Anant, P.; Lucas, N. T.; Jacob, J. *Org. Lett.* 2008, 10, 5533. (b) Kato, S.; Matsumoto, T.; Shigeiwa, M.; Gorohmaru, H.; Maeda, S.; Ishi-i, T.; Mataka, S. *Chem. Eur. J.* 2006, 12, 2303.
9. Focante, F.; Mercandelli, P.; Sironi, A.; Resconi, L. *Coord. Chem. Rev.* 2006, 250, 170.
10. (a) Fraleoni-Morgera; A.; Giorgini, L.; Zanirato, P. *Dyes and Pigments* 2008, 76, 394-399. (b) Cazenobe, I.; Ledoux, I.; Zyss, J.; Thornton, A.; Bruce, D. W.; Kakkar, A. K.; Lesley, G. M. J.; Woodward, A.; Taylor, N. J.; Marder, T. B. *Chem. Mater.* 1998, 10, 1355. (c) Lopez-Garriga, J. J.; Babcock, G. T.; Harrison, J. F. *J. Am. Chem. Soc.* 1986, 108, 7131.
11. (a) Son, H. J.; Han, W. S.; Chun, J. Y.; Kwon, S, N.; Ko, J.; Kang, S. O. *Organometallics* 2008, 27, 2464. (b) Lee, I. S.; Kwak, Y. W.; Kim, D. H.; Cho, Y.; Ohshita J. J. *Orgmet. Chem.* 2008, 693, 3233. (c) Lee, I. S.; Kim S. J.; Kwak, Y. W.; Choi, M. C.; Park, J. W.; Ha, C. K. J. *Indus. Engn. Chem.* 2008, 14, 344.
12. See Supporting Information (Example 2)
13. (a) Piers, W. E. *Adv. Orgmet. Chem.* 2005, 52, 1. (b) Massey, A. G.; Park, A. J.; Stone, F. G. A. *Proc. Chem. Soc.* 1963, 208.
14. Pearson, R. G. *J. Am. Chem. Soc.,* 1963, 85, 3533.
15. Focante, F.; Camurati, I.; Resconi, L.; Guidotti, S.; Beringhelli, T.; D'Alfonso, G.; Donghi, D.; Maggioni, D.; Mercandelli, P.; Sironi, A. *Inorg. Chem.,* 2006, 45, 1683.
16. Jacobsen, H.; Berke, H.; Döring, S.; Kehr, G.; Erker, G.; Fröhlich, R.; Meyer, O. *Organometallics* 1999, 18, 1724.
17. Apblett, A.; Chivers, T.; Richardson, J. F. *Can. J. Chem.* 1986, 64, 849.
18. Bazan G. C. *J. Org. Chem.* 2007, 72, 8651.
19. Pilgram, K.; Zupan, M.; Skiles, R. J. Heterocyclic Chemistry 1970, 7, 629-633.
20. Lu, G.; Usta, H.; Risko, C.; Wang, L.; Facchetti, A.; Ratner, M. A.; Marks, T. J. J. Am. Chem. Soc. 2008, 130, 7670-7685.
21. Bruker AXS Inc: Madison, Wis., 2001.
22. Bruker AXS Inc.: Madison, Wis., 2003.
23. Sheldrick, G. M.; Bruker AXS Inc.: Madison, Wis., 2000.
24. Spek, A. L. Journal of Applied Crystallography 2003, 36, 7-13.
25. Zhu, Z. et al., *Macromolecules* 40, 1981-1986 (2007).
26. Coffin, R.; Peet, J.; Rogers, J.; Bazan, G. *Nat. Chem.* 2009, 1, 657.
27. Coppo, P.; Cupertino, D. C.; Yeates, S. G.; Turner, M. L. *Macromolecules* 2003, 36, 2705.
28. Blouin, N.; Michaud, A.; Gendron, D.; Wakim, S.; Blair, E.; Neagu-Plesu, R.; Belletete, M.; Durocher, G.; Tao, Y.; Leclerc, M.; *J. Am. Chem. Soc.* 2008, 130, 2, 732.
29. Bruker AXS Inc: Madison, Wis., 2001.
30. Bruker AXS Inc.: Madison, Wis., 2003.
31. Sheldrick, G. M.; Bruker AXS Inc.: Madison, Wis., 2000.
32. Spek, A. L. *Journal of Applied Crystallography* 2003, 36, 7-13.
33. Frisch, M. J.; Trucks, G. W.; Schlegel, H. B., et al., *Gaussian* 03, Gaussian, Inc., Wallingford Conn., 2004.
34. a) Becke, A. D. *J. Chem. Phys.* 1993, 98, 1372; b) Becke, A. D. *J. Chem. Phys.* 1993, 98, 5648; c) Lee, C.; Yang, W.; Parr, R. G. *Phys. Rev. B* 1988, 37, 785.
35. Bram, P. et al., J. Mater. Chem., 2009, 19, 5343-5350.

What is claimed is:

1. An electronic device comprising a Lewis acid adduct, the adduct comprising a Lewis acid and a chemical compound comprising the following structure (I)

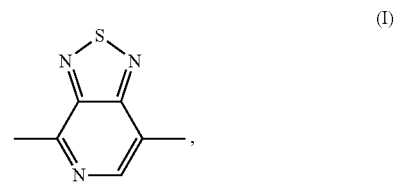

wherein the Lewis acid binds to structure (I).

2. The electronic device of claim 1, further comprising a dithiophene, wherein structure (I) is arranged with the dithiophene according to the following structure (II)

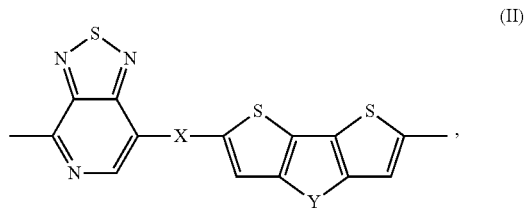

wherein X is nothing or a thiophene ring and Y is =CR$_4$R$_5$ or =SiR$_4$R$_5$, and wherein R$_4$ and R$_5$ are each independently a C$_{1-30}$ alkyl or C$_{5-30}$ aryl.

3. The electronic device of claim 1, wherein the Lewis acid is BR$_3$, AlR$_3$, GaR$_3$, R$_2$BXBR$_2$, R$_2$AlXAlR$_2$ where R=F, Cl, Br, alkyl with C$_n$ (n=1 to 30), aryl with C$_n$ (n=5 to 30), perfluoroalkyl with C$_n$ (n=1 to 30), perfluoroaryl with C$_n$ (n=5 to 30), or any combination thereof, and X=alkyl with C$_n$ (n=1 to 30), aryl with C$_n$ (n=5 to 30), perfluoroalkyl with C$_n$ (n=1 to 30), perfluoroaryl with C$_n$ (n=5 to 30), or any combination thereof.

4. The electronic device of claim 1, wherein the chemical compound is a conjugated oligomer, a conjugated polymer, or a small molecule comprising a conjugated π-electron system.

5. The electronic device of claim 4, wherein the chemical compound is a chromophore.

6. The electronic device of claim 1, wherein the chemical compound is one or any combination of the following:

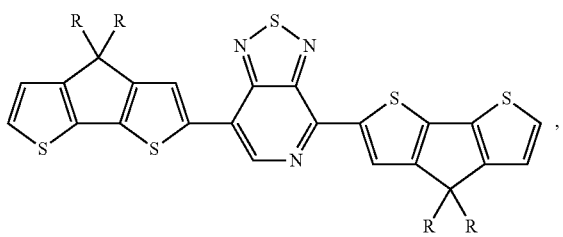

-continued

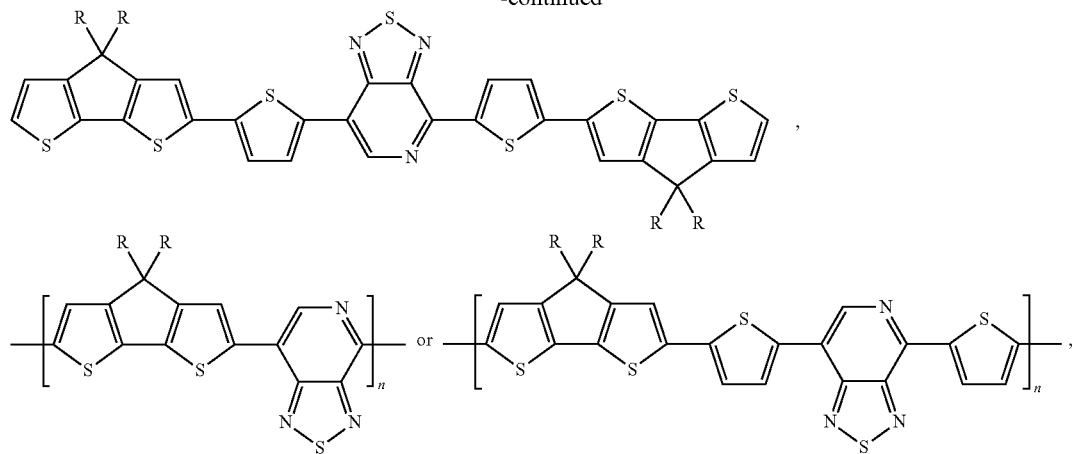

wherein each R is independently a $C_{1-30}$ alkyl or $C_{5-30}$ aryl group, and each n is $\geq 1$.

7. The electronic device of claim 6, wherein the chemical compound is

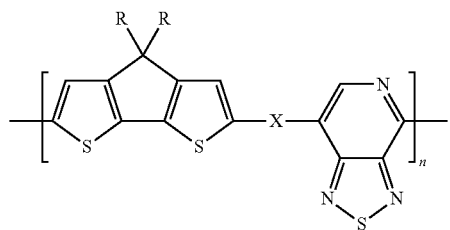

and the Lewis acid is $B(C_6F_5)_3$.

8. The electronic device of claim 1, wherein the device is an optoelectronic device, optoelectronic semiconductor chip, semiconductor thin-film, photovoltaic, semiconducting solar cell or dye-sensitized solar cell.

9. The electronic device of claim 1, wherein the device is a solar cell.

* * * * *